(12) United States Patent
Korman et al.

(10) Patent No.: US 8,263,073 B2
(45) Date of Patent: Sep. 11, 2012

(54) ANTI-CTLA-4 ANTIBODIES WITH REDUCED BLOCKING OF BINDING OF CTLA-4 TO B7 AND USES THEREOF

(75) Inventors: Alan Korman, Piedmont, CA (US);
Edward L. Halk, Sunnyvale, CA (US);
Changyu Wang, Union City, CA (US);
Kent B. Thudium, Oakland, CA (US);
Lan Yang, Morgan Hill, CA (US);
Kristopher Toy, San Jose, CA (US)

(73) Assignee: Medarex, Inc., Princeton, NJ (US)

( * ) Notice: Subject to any disclaimer, the term of this patent is extended or adjusted under 35 U.S.C. 154(b) by 0 days.

(21) Appl. No.: 12/866,149

(22) PCT Filed: Feb. 4, 2009

(86) PCT No.: PCT/US2009/033089
§ 371 (c)(1),
(2), (4) Date: Nov. 22, 2010

(87) PCT Pub. No.: WO2009/100140
PCT Pub. Date: Aug. 13, 2009

(65) Prior Publication Data
US 2011/0081354 A1 Apr. 7, 2011

Related U.S. Application Data

(60) Provisional application No. 61/026,061, filed on Feb. 4, 2008.

(51) Int. Cl.
*A61K 39/395* (2006.01)
(52) U.S. Cl. .................................................. 424/130.1
(58) Field of Classification Search .................... None
See application file for complete search history.

(56) References Cited

U.S. PATENT DOCUMENTS

2002/0086014 A1* 7/2002 Korman et al. ............ 424/144.1

FOREIGN PATENT DOCUMENTS

| WO | WO 00/37504 | 6/2000 |
| WO | WO 01/14424 | 3/2001 |
| WO | WO 02/43478 | 6/2002 |

OTHER PUBLICATIONS

Springer et al., Ann. Rev. Immunol. 5: 223-252 (1987).
Dinarello, New Engl. J. Med. 317: 940-945 (1987).
Sallusto, J. Exp. Med. 179: 1109-1118 (1994).
Weiss, Ann. Rev. Immunol. 4: 593-619 (1986).
Allison, Curr. Opin. Immunol. 6: 414-419 (1994).
McMichael, Ed. Leukocyte Typing III, Oxford Univ. Press, Oxford, N.Y. ((1987).
Aruffo and Seed, Proc. Natl. Acad. Sci. USA 84: 8573-8577 (1987).
Damle et al., J. Immunol 131: 2296-2300 (1983).
Damle et al., Proc. Natl. Acad. Sci. USA 78: 5096-6001 (1981).
Lesslauer et al., Eur. J. Immunol. 16: 1289-1296 (1986).
Brunet et al., Nature 328: 267-270 (1987).
Brunet et al., Immunol. Rev. 103: 21-36 (1988).
Dariavach et al., Eur. J. Immunol. 18: 1901-1905 (1988).
Lafage-Pochitaloff et al., Immunogenetics 31: 198-201 (1990).
Chambers et al., Immunity 7: 885-895 (1997).
Walunas et al., Immunity 1: 405-413 (1994).
Kearney, J. Immunol. 155: 1032-1036 (1995).
Leach, Science 271: 1734-1736 (1996).
Luhder, J. Exp. Med. 187: 427-432 (1998).
Chambers, Curr. Opin. Immunol. 9 :396-404 (1997).
Bluestone, J. Immunol 158: 1989-1993 (1997).
Thompson, Immunity 7 : 445-450 (1997).
Matsui, J. Immunol. 162: 4328-4335 (1999).
Linsley et al., J. Exp. Med. 174: 561-569 (1991).
Freeman et al., Science 262: 909-911 (1993).
Van der Merwe et al., J. Exp. Med. 185: 393-403 (1997).
Keler et al., J. Immunol. 171: 6251-6259 (2003).
Stamper et al., Nature 410: 608-611 (2001).

* cited by examiner

*Primary Examiner* — Ilia Ouspenski
(74) *Attorney, Agent, or Firm* — Paul D. Golian

(57) ABSTRACT

The present invention provides isolated monoclonal antibodies that bind to CTLA-4 and that are capable of increasing the response of T cells to antigenic stimulation in vivo yet the antibodies do not substantially block the binding of CTLA-4 to B7 ligands (e.g., B7-1 and B7-2) in vitro. Thus, the antibodies of the invention demonstrate that is it possible to separate the immunostimulatory function of anti-CTLA-4 antibodies from their ability to block the binding of B7 ligands. Immunoconjugates, bispecific molecules and pharmaceutical compositions comprising the antibodies of the invention are also provided. The invention also provides methods for increasing the response of T cells to antigenic stimulation using the antibodies of the invention, including methods for treating cancer using the antibodies of the invention.

4 Claims, 17 Drawing Sheets

Anti-CTLA-4 1H5 VH

V segment:      4-39
    D segment:      6-13
    J segment:      JH6b

```
           Q   L   Q   L   Q   E   S   G   P   G   L   V   K   P   S   E   T   L
  1        CAG TTG CAG CTG CAG GAG TCG GGC CCA GGA CTG GTG AAG CCT TCG GAG ACC CTG

CDR1
                                                                    ~~~~~~~~~~~~~~~~~~~~~~~
           S   L   T   C   T   V   S   G   G   S   I   S   N   S   N   Y   Y   W
  55       TCC CTC ACC TGC ACT GTC TCT GGT GGC TCC ATC AGC AAT AGT AAT TAC TAC TGG

CDR1                                                             CDR2
           ~~~                                                              ~~~~~~~~~~~
           G   W   I   R   Q   P   P   G   K   E   L   E   W   I   G   S   I   Y
  109      GGC TGG ATC CGC CAG CCC CCA GGG AAG GAA CTG GAG TGG ATT GGG AGT ATC TAT

CDR2
           ~~~~~~~~~~~~~~~~~~~~~~~~~~~~~~~~~~~~~~~~~~~~~~~~~~~~~~~~~~~~~~
           Y   T   G   N   T   Y   Y   N   P   S   L   K   S   R   V   T   V   S
  163      TAT ACT GGG AAC ACC TAC TAC AAC CCG TCC CTC AAG AGT CGA GTC ACC GTG TCC

V   D   T   S   R   N   Q   F   S   L   N   L   N   S   V   I   A   A
  217      GTA GAC ACG TCC AGG AAC CAG TTC TCC CTG AAC CTG AAT TCT GTT ATC GCC GCA

CDR3
                                                                  ~~~~~~~~~~~~~~~~~~~~~~~~~~
           D   T   A   V   Y   S   C   A   R   H   G   F   T   I   S   W   S   L
  271      GAC ACG GCT GTG TAT TCC TGT GCG AGA CAT GGG TTT ACC ATC AGC TGG TCT TTG

CDR3
           ~~~~~~~
           D   V   W   G   Q   G   T   T   V   T   V   S   S
  325      GAC GTC TGG GGC CAA GGG ACC ACG GTC ACC GTC TCC TCA
```

FIGURE 1

Anti-CTLA-4 1H5 VK#1 (predominant chain)

V segment:    L18
J segment:    JK4

```
          A   I   Q   L   T   Q   S   P   S   S   L   S   A   S   V   G   D   R
  1      GCC ATC CAG TTG ACC CAG TCT CCA TCC TCC CTG TCT GCA TCT GTA GGA GAC AGA

CDR1
                               ~~~~~~~~~~~~~~~~~~~~~~~~~~~~~~~~~~~~~~~~~~~
          V   T   I   T   C   R   A   S   Q   G   I   S   S   A   L   A   W   Y
 55      GTC ACC ATC ACT TGC CGG GCA AGT CAG GGC ATT AGC AGT GCT TTA GCC TGG TAT

CDR2
                                                          ~~~~~~~~~~~~~~~~~~~~
          Q   Q   K   P   G   K   A   P   K   L   L   I   Y   D   A   S   S   L
109      CAG CAG AAA CCA GGG AAA GCT CCT AAG CTC CTG ATC TAT GAT GCC TCC AGT TTG

CDR2
         ~~~~~~~
          E   S   G   V   P   S   R   F   S   G   S   G   S   G   T   D   F   T
163      GAA AGT GGG GTC CCA TCA AGG TTC AGC GGC AGT GGA TCT GGG ACA GAT TTC ACT

CDR3
                                                                          ~~~~~~~
          L   T   I   S   S   L   Q   P   E   D   F   A   T   Y   Y   C   Q   Q
217      CTC ACC ATC AGC AGC CTG CAG CCT GAA GAT TTT GCA ACT TAT TAC TGT CAA CAG

CDR3
         ~~~~~~~~~~~~~~~~~~~~~~~~~~~~
          F   N   S   Y   L   L   T   F   G   G   G   T   K   V   E   I   K
271      TTT AAT AGT TAC CTG CTC ACT TTC GGC GGA GGG ACC AAG GTG GAG ATC AAA
```

FIGURE 2A

Anti-CTLA4 1H5 VK#2

V segment:   L15
J segment:   JK3

```
          D   I   Q   M   T   Q   S   P   S   S   L   S   A   S   V   G   D   R
  1       GAC ATC CAG ATG ACC CAG TCT CCA TCC TCA CTG TCT GCA TCT GTA GGA GAC AGA
                                                  CDR1
                                                  ~~~~~~~~~~~~~~~~~~~~~~~~~~~~~~~~~~~
          V   T   I   T   C   R   A   S   Q   G   I   S   S   W   L   A   W   Y
 55       GTC ACC ATC ACT TGT CGG GCG AGT CAG GGT ATT AGC AGC TGG TTA GCC TGG TAT
                                                                        CDR2
                                                                        ~~~~~~~~~~~~~~~~~~
          Q   Q   K   P   E   K   A   P   K   S   L   I   Y   A   A   S   S   L
109       CAG CAG AAA CCA GAG AAA GCC CCT AAG TCC CTG ATC TAT GCT GCA TCC AGT TTG

CDR2
          ~~~~~~~
          Q   S   G   V   P   S   R   F   S   G   S   G   S   G   T   D   F   T
163       CAA AGT GGG GTC CCA TCA AGG TTC AGC GGC AGT GGA TCT GGG ACA GAT TTC ACT
                                                                              CDR3
                                                                              ~~~~~~~
          L   T   I   S   S   L   Q   P   E   D   F   A   T   Y   Y   C   Q   Q
217       CTC ACC ATC AGC AGC CTG CAG CCT GAA GAT TTT GCA ACT TAT TAC TGC CAA CAG

CDR3
                  ~~~~~~~~~~~~~~~~~~~~~~~~~~~~~~~
          Y   N   S   Y   P   L   F   T   F   G   P   G   T   K   V   D   I   K
271       TAT AAT AGT TAC CCT TTA TTC ACT TTC GGC CCT GGG ACC AAA GTG GAT ATC AAA
```

FIGURE 2B

Anti-CTLA4 1H5 VK#3

V segment:       L15
    J segment:       JK4

```
          D   I   Q   M   T   Q   S   P   S   S   L   S   A   S   V   G   D   R
 1       GAC ATC CAG ATG ACC CAG TCT CCA TCC TCA CTG TCT GCA TCT GTA GGA GAC AGA
                                                CDR1
                                        ~~~~~~~~~~~~~~~~~~~~~~~~~~~~~~~~~~~~~~~~
          V   T   I   T   C   R   A   S   Q   G   I   S   S   W   L   A   W   Y
 55      GTC ACC ATC ACT TGT CGG GCG AGT CAG GGT ATT AGC AGC TGG TTA GCC TGG TAT
                                                                    CDR2
                                                            ~~~~~~~~~~~~~~~~~~~~
          Q   Q   K   P   E   K   A   P   K   S   L   I   Y   A   A   S   S   L
 109     CAG CAG AAA CCA GAG AAA GCC CCT AAG TCC CTG ATC TAT GCT GCA TCC AGT TTG

CDR2
         ~~~~~~~
          Q   S   G   V   P   S   R   F   S   G   S   G   S   G   T   D   F   T
 163     CAA AGT GGG GTC CCA TCA AGG TTC AGC GGC AGT GGA TCT GGG ACA GAT TTC ACT
                                                                            CDR3
                                                                            ~~~~~~~
          L   T   I   S   S   L   Q   P   E   D   F   A   T   Y   Y   C   Q   Q
 217     CTC ACC ATC AGC AGC CTG CAG CCT GAA GAT TTT GCA ACT TAT TAC TGC CAA CAG

CDR3
         ~~~~~~~~~~~~~~~~~~~~~~~~~~~
          Y   N   S   Y   P   L   T   F   G   G   G   T   K   V   E   I   K
 271     TAT AAT AGT TAC CCG CTC ACT TTC GGC GGA GGG ACC AAG GTG GAG ATC AAA
```

FIGURE 2C

Anti-CTLA4 1H5 VK#4

V segment: L15
J segment: JK4

```
          D    I    Q    M    T    Q    S    P    S    S    L    S    A    S    V    G    D    R
  1      GAC  ATC  CAG  ATG  ACC  CAG  TCT  CCA  TCC  TCA  CTG  TCT  GCA  TCT  GTA  GGA  GAC  AGA

CDR1
                                                      ~~~~~~~~~~~~~~~~~~~~~~~~~~~~~~~~~~~~~~~~~~~
          V    T    I    T    C    R    A    S    Q    G    I    S    S    W    L    A    W    Y
 55      GTC  ACC  ATC  ACT  TGT  CGG  GCG  AGT  CAG  GGT  ATT  AGC  AGC  TGG  TTA  GCC  TGG  TAT

CDR2
                                                                ~~~~~~~~~~~~~~~~~~~~~~~~~~~~~~
          Q    Q    K    P    E    K    A    P    K    S    L    I    Y    A    A    S    S    L
109      CAG  CAG  AAA  CCA  GAG  AAA  GCC  CCT  AAG  TCC  CTG  ATC  TAT  GCT  GCA  TCC  AGT  TTG

CDR2
         ~~~~~~~
          Q    S    G    V    P    S    R    F    S    G    S    G    S    G    T    D    F    T
163      CAA  AGT  GGG  GTC  CCA  TCA  AGG  TTC  AGC  GGC  AGT  GGA  TCT  GGG  ACA  GAT  TTC  ACT

CDR3
                                                                                         ~~~~~~~
          L    T    I    S    S    L    Q    P    E    D    F    A    T    Y    Y    C    Q    Q
217      CTC  ACC  ATC  AGC  AGC  CTG  CAG  CCT  GAA  GAT  TTT  GCA  ACT  TAT  TAC  TGT  CAA  CAG

CDR3
         ~~~~~~~~~~~~~~~~~~~~~~~~~~~
          F    N    S    Y    L    L    T    F    G    G    G    T    K    V    E    I    K
271      TTT  AAT  AGT  TAC  CTG  CTC  ACT  TTC  GGC  GGA  GGG  ACC  AAG  GTG  GAG  ATC  AAA
```

FIGURE 2D

Anti-CTLA-4 3A4 VH

V-segment: 3-33
    D-segment: 6-13
    J-segment: JH4b

```
          Q   V   Q   V   V   E   S   G   G   G   V   V   Q   P   G   R   S   L
  1      CAG GTG CAG GTG GTG GAG TCT GGG GGA GGC GTG GTC CAG CCT GGG AGG TCC CTG
                                                                    CDR1
                                                         ~~~~~~~~~~~~~~~~~~~~
          R   L   S   C   A   A   S   G   F   T   F   S   S   Y   G   M   H   W
  55     AGA CTC TCC TGT GCA GCG TCT GGA TTC ACC TTC AGT AGC TAT GGC ATG CAC TGG
                                                                    CDR2
                                                         ~~~~~~~~~~~~~~~~~~~~
          V   R   Q   A   P   G   K   G   L   E   W   V   A   V   I   W   Y   D
 109     GTC CGC CAG GCT CCA GGC AAG GGG CTG GAG TGG GTG GCA GTT ATA TGG TAT GAT
                          CDR2
         ~~~~~~~~~~~~~~~~~~~~~~~~~~~~~~~~~~~~~~~~~~~~~~~
          G   S   N   K   Y   Y   V   D   S   V   K   G   R   F   T   I   S   R
 163     GGA AGT AAT AAA TAT TAT GTA GAC TCC GTG AAG GGC CGA TTC ACC ATC TCC AGA

D   N   S   K   N   T   L   Y   L   Q   M   N   S   L   R   A   E   D
 217     GAC AAT TCC AAG AAC ACG CTG TAT CTG CAA ATG AAC AGC CTG AGA GCC GAG GAC
                                                     CDR3
                                         ~~~~~~~~~~~~~~~~~~~~~~~~~~~~~~~~~~~~~~~~
          T   A   V   Y   Y   C   A   R   G   P   G   Y   S   S   S   F   D   Y
 271     ACG GCT GTG TAT TAC TGT GCG AGA GGT CCC GGG TAT AGC AGC AGC TTT GAC TAC

W   G   Q   G   T   L   V   T   V   S   S
 325     TGG GGC CAG GGA ACC CTG GTC ACC GTC TCC TCA
```

FIGURE 3

Anti-CTLA-4 3A4 VK

V-segment: L15
J-segment: JK4

```
            D   I   Q   M   T   Q   S   P   S   S   L   S   A   S   V   G   D   R
  1        GAC ATC CAG ATG ACC CAG TCT CCA TCC TCA CTG TCT GCA TCT GTA GGA GAC AGA

CDR1
                                              ~~~~~~~~~~~~~~~~~~~~~~~~~~~~~~~~~~~~~~~~~
            V   T   I   T   C   R   A   S   Q   G   I   S   S   W   L   A   W   Y
  55       GTC ACC ATC ACT TGT CGG GCG AGT CAG GGT ATT AGC AGC TGG TTA GCC TGG TAT

CDR2
                                                              ~~~~~~~~~~~~~~~~~~~~~
            Q   Q   K   P   E   K   A   P   K   S   L   I   Y   A   A   S   S   L
  109      CAG CAG AAA CCA GAG AAA GCC CCT AAG TCC CTG ATC TAT GCT GCA TCC AGT TTG

CDR2
           ~~~~~~~
            Q   S   G   V   P   S   R   F   S   G   S   G   S   G   T   D   F   T
  163      CAA AGT GGG GTC CCA TCA AGG TTC AGC GGC AGT GGA TCT GGG ACA GAT TTC ACT

CDR3
                                                                              ~~~~~~~
            L   T   I   S   S   L   Q   P   E   D   F   A   T   Y   Y   C   Q   Q
  217      CTC ACC ATC AGC AGC CTG CAG CCT GAA GAT TTT GCA ACT TAT TAC TGC CAA CAG

CDR3
           ~~~~~~~~~~~~~~~~~~~~~~~~~~~~~~
            Y   N   S   Y   P   L   T   F   G   G   G   T   K   V   E   I   K
  271      TAT AAT AGT TAC CCT CTC ACT TTC GGC GGA GGG ACC AAG GTG GAG ATC AAA
```

FIGURE 4

Anti-CTLA-4 6C10 VH

V segment:       3-33
    D segment:       6-19
    J segment:       JH4b

```
           Q   V   Q   L   V   E   S   G   G   G   V   V   Q   P   G   R   S   L
  1       CAG GTG CAA CTG GTG GAA TCT GGG GGA GGC GTG GTC CAG CCT GGG AGG TCC CTG

CDR1
                                                                    ~~~~~~~~~~~~~~~~~~~
           R   L   S   C   T   A   S   G   F   T   F   S   S   H   G   M   H   W
 55       AGA CTC TCC TGT ACA GCG TCT GGA TTC ACC TTC AGT AGC CAT GGC ATG CAC TGG

CDR2
                                                                    ~~~~~~~~~~~~~~~~~~~
           V   R   Q   A   P   G   K   G   L   E   W   V   A   V   V   W   F   D
109       GTC CGC CAG GCT CCA GGC AAG GGG CTG GAG TGG GTG GCA GTT GTA TGG TTT GAT

CDR2
          ~~~~~~~~~~~~~~~~~~~~~~~~~~~~~~~~~~~~~~~~~~~~~~~~~~
           G   S   N   K   Y   Y   V   D   S   V   K   G   R   F   T   I   S   R
163       GGA AGT AAT AAA TAC TAT GTA GAC TCC GTG AAG GGC CGA TTC ACC ATC TCC AGA

D   N   S   K   N   T   L   Y   L   Q   M   N   S   L   R   A   E   D
217       GAC AAT TCC AAG AAC ACG CTG TAT CTA CAA ATG AAC AGC CTG AGA GCC GAG GAC

CDR3
                                                        ~~~~~~~~~~~~~~~~~~~~~~~~~~~~~~~~~
           T   A   V   Y   Y   C   A   R   G   S   G   Y   S   S   G   F   D   Y
271       ACG GCT GTG TAT TAC TGT GCG AGA GGC TCC GGG TAT AGC AGT GGC TTT GAC TAC

W   G   Q   G   T   L   V   T   V   S   S
325       TGG GGC CAG GGA ACC CTG GTC ACC GTC TCC TCA
```

FIGURE 5

Anti-CTLA-4 6C10 VK

V segment:    L15
    J segment:    JK4

```
         D   I   Q   M   T   Q   S   P   S   S   L   S   A   S   V   G   D   R
  1     GAC ATC CAG ATG ACC CAG TCT CCA TCC TCA CTG TCT GCA TCT GTA GGA GAC AGA

CDR1
                                    ~~~~~~~~~~~~~~~~~~~~~~~~~~~~~~~~~~~~
         V   T   I   T   C   R   A   S   Q   G   I   S   S   W   L   A   W   Y
 55     GTC ACC ATC ACT TGT CGG GCG AGT CAG GGT ATT AGC AGC TGG TTA GCC TGG TAT

CDR2
                                                                ~~~~~~~~~~~~~~~~~
         Q   Q   K   P   E   K   A   P   K   S   L   I   Y   A   A   S   S   L
109     CAG CAG AAA CCA GAG AAA GCC CCT AAG TCC CTG ATC TAT GCT GCA TCC AGT TTG

CDR2
        ~~~~~~~
         Q   S   G   V   P   S   R   F   S   G   S   G   S   G   T   D   F   T
163     CAA AGT GGG GTC CCA TCA AGG TTC AGC GGC AGT GGA TCT GGG ACA GAT TTC ACT

CDR3
                                                                           ~~~~~~~
         L   T   I   S   S   L   Q   P   E   D   F   A   T   Y   Y   C   Q   Q
217     CTC ACC ATC AGC AGC CTG CAG CCT GAA GAT TTT GCA ACT TAT TAC TGC CAA CAG

CDR3
        ~~~~~~~~~~~~~~~~~~~~~~~~~~~~~
         Y   N   S   Y   P   L   T   F   G   G   G   T   K   V   E   I   K
271     TAT AAT AGT TAC CCG CTC ACT TTC GGC GGA GGG ACC AAG GTG GAG ATC AAA
```

FIGURE 6

Anti-CTLA-4 1H5 VH Region

```
                                                                    CDR1
4-39 germline:  Q L Q L Q E S G P G L V K P S E T L S L T C T V S G G S I S S - - S S Y Y W G W I
1H5 VH:         - - - - - - - - - - - - - - - - - - - - - - - - - - - - N - N - - - - Y - - - -

CDR2
4-39 germline:  R Q P P G K G L E W I G S I Y Y S G S T Y Y N P S L K S R V T I S V D T S K N
1H5 VH:         - - - - - - - - - E - - - - - - - - T - N - - - - - - - - - - - V - - - - R -

CDR3
4-39 germline:  Q F S L K L S S V T A A D T A V Y Y C A R
1H5 VH:         - - - - N - N - - H - - - - - - - - - - S - - H G F T I S W S L D V W G Q G T T V JH6b germline:  T V S S
1H5 VH:         - - - -
```

FIGURE 7

Anti-CTLA4 3A4 VH regions

```
                                                   CDR1                          CDR2
V_H 3-33
Germline:  QVQLVESGGGVVQPGRSLRLSCAASGFTFS  SYGMH  WVRQAPGKGLEWVA  VIWYDGSNKYYADSVKG
3A4:       ---V--------------------------  -----  --------------  ---------V-------

CDR3
V_H 3-33:  RFTISRDNSKNTLYLQMNSLRAEDTAVYYCAR  GPGYSSSFDY  WGQGTLVTVSS
3A4:       --------------------------------  ----------  -----------
```

FIGURE 8

Anti-CTLA4 VH region

```
3-33 Germline: Q V Q L V E S G G G V V Q P G R S L R L S C A A S G F T F S   S Y G M H W V R Q
                                                                         CDR1
6C10 VH:       - - - - - - - - - - - - - - - - - - - - - - T - - - - - - H - - - - - - - -

3-33 Germline: A P G K G L E W V A   V I W Y D G S N K Y Y A D S V K G   R F T I S R D N S K N T
                                     CDR2
6C10 VH:       - - - - - - - - - -   V - - - - - - - - - - - - V - - -   - - - - - - - - - - -
                                       F 3-33 Germline: L Y L Q M N S L R A E D T A V Y Y C A R - -   G S G Y S S G F D Y   W G Q G T L V T V
                                                             CDR3
6C10 VH:       - - - - - - - - - - - - - - - - - - - - -   - - - - - - - - - -   - - - - - - - - -

Anti-CTLA-4 1H5 VK1 Region

```
                                                                   CDR1
L18 germline:   A I Q L T Q S P S S L S A S V G D R V T I T C R A S Q G I S S A L A
1H5 VK:         - - - - - - - - - - - - - - - - - - - - - - - - - - - - - - - - -

CDR2
L18 germline:   W Y Q Q K P G K A P K L L I Y D A S S L E S G V P S R F S G S G S G
1H5 VK:         - - - - - - - - - - - - - - - - - - - - - - - - - - - - - - - - -

CDR3
L18 germline:   T D F T L T I S S L Q P E D F A T Y Y C Q Q F N S Y         L T F G G G T
JK4 germline:                                                         L
1H5 VK:         - - - - - - - - - - - - - - - - - - - - - - - - -       - - - - - - -

JK4 germline:   K V E I K    (JK4)
1H5 VK:         - - - - -
```

FIGURE 10

Anti-CTLA-4 3A4 & 6C10 VK Regions

```
                                          ____CDR1____                ____CDR2____
V_K L-15
Germline:   DIQMTQSPSSLSASVGDRVTITC  RASQGISSWLA  WYQQKPEKAPKSLIY  AASSLQS
3A4:        ----------------------   -----------  ---------------  -------

____CDR3____
V_K L-15:   GVPSRFSGSGSGTDFTLTISSLQPEDFATYYC  QQYNSYP
3A4:        --------------------------------  -------  ----LTFGGGTKVEIK
```

FIGURE 11

Anti-CTLA-4 6C10 VK Region

```
                                                            CDR1
                                                         ┌─────────────┐
L15 germline    D I Q M T Q S P S S L S A S V G D R V T I T C R A S Q G I S S W L A
6C10 VK         - - - - - - - - - - - - - - - - - - - - - - - - - - - - - - - - -

CDR2
                                                 ┌─────────────┐
L15 germline    W Y Q Q K P E K A P K S L I Y A A S S L Q S G V P S R F S G S G S G
6C10 VK         - - - - - - - - - - - - - - - - - - - - - - - - - - - - - - - - -

CDR3
                                               ┌─────────────────┐
L15 germline    T D F T L T I S S L Q P E D F A T Y Y C Q Q Y N S Y P   L T F G G G T
JK4 germline                                                             - - - - - -
6C10 VK         - - - - - - - - - - - - - - - - - - - - - - - - - -      - - - - - -

JK4 germline    K V E I K   (JK4)
6C10 VK         - - - - -
```

FIGURE 12

10D1 Heavy Chain Variable Region

```
                                                   CDR1                            CDR2
10D1 VH:   QVQLVESGGGVVQPGRSLRLSCAASGFTFS          SYTMH    WVRQAPGKGLEWVT         FISYDGNNKYYADSVKG

CDR3
10D1 VH:   RFTISRDNSKNTLYLQMNSLRAEDTAIYYCAR        TGWLGPFDY    WGQGTLVTVSS
```

10D1 Light Chain Variable Region

```
                                                   CDR1                            CDR2
10D1 VK:   EIVLTQSPGTLSLSPGERATLSC                 RASQSVGSSYLA   WYQQKPGQAPRLLIY  GAFSRAT

CDR3
10D1 VK:   GIPDRFSGSGSGTDFTLTISRLEPEDFAVYYC        QQYGSSPWT    FGQGTKVEIK
```

FIGURE 15

ANTI-CTLA-4 ANTIBODIES WITH REDUCED BLOCKING OF BINDING OF CTLA-4 TO B7 AND USES THEREOF

This application incorporates by reference the Sequence Listing named 20101122_SEQ_M00203USPCT.txt dated Oct. 14, 2010 and size 24 KB.

TECHNICAL FIELD

The present invention provides anti-CTLA-4 monoclonal antibodies with reduced blocking of binding of CTLA-4 to B7 that are capable of increasing the response of T cells to antigenic stimulation in vivo, yet the antibodies do not substantially inhibit the binding of a soluble human CTLA-4 protein to cells expressing B7-1, for the treatment of cancers, infectious diseases, as well as for increasing the effectiveness of vaccinations.

BACKGROUND ART

A T cell immune response is a complex process that involves cell-cell interactions (Springer et al. (1987) Ann. Rev. Immunol. 5:223-252), particularly between T and accessory cells such as APC's, and production of soluble immune mediators (cytokines or lymphokines) (Dinarello (1987) New Engl. J. Med. 317:940-945; Sallusto (1997) J. Exp. Med. 179:1109-1118). This response is regulated by several T-cell surface receptors, including the T-cell receptor complex (Weiss (1986) Ann. Rev. Immunol. 4:593-619) and other "accessory" surface molecules (Allison (1994) Curr. Opin. Immunol. 6:414-419; Springer (1987) supra). Many of these accessory molecules are naturally occurring cell surface cluster of differentiation (CD) antigens defined by the reactivity of monoclonal antibodies on the surface of cells (McMichael, Ed. (1987), Leukocyte Typing III, Oxford Univ. Press, Oxford, N.Y.).

CD28 antigen, a homodimeric glycoprotein of the immunoglobulin superfamily (Aruffo and Seed (1987) Proc. Natl. Acad. Sci. USA 84:8573-8577), is an accessory molecule found on most mature human T cells (Damle et al. (1983) J. Immunol. 131:2296-2300). Monoclonal antibodies (MAbs) reactive with CD28 antigen can augment T cell responses initiated by various polyclonal stimuli. Anti-CD28 mAbs can also have inhibitory effects, i.e., they can block autologous mixed lymphocyte reactions (Damle et al. (1981) Proc. Natl. Acad. Sci. USA 78:5096-6001) and activation of antigen-specific T cell clones (Lesslauer et al. (1986) Eur. J. Immunol. 16:1289-1296). CD28 is a counter-receptor for the B cell activation antigens B7-1 and B7-2.

CTLA-4 is a T cell surface molecule that was originally identified by differential screening of a murine cytolytic T cell cDNA library (Brunet et al. (1987) Nature 328:267-270). CTLA-4 is a member of the immunoglobulin (Ig) superfamily, comprising a single extracellular Ig domain. CTLA-4 transcripts have been found in T cell populations having cytotoxic activity (Brunet et al., supra; Brunet et al. (1988) Immunol. Rev. 103:21-36). Researchers have reported the cloning and mapping of the human CTLA4 gene (Dariavach et al. (1988) Eur. J. Immunol. 18:1901-1905) to the same chromosomal region (2q33-34) as CD28 (Lafage-Pochitaloff et al. (1990) Immunogenetics 31:198-201). Sequence comparison between this human CTLA-4 DNA and that encoding CD28 proteins reveals significant homology of sequence, with the greatest degree of homology in the juxtamembrane and cytoplasmic regions (Brunet et al., 1988, supra; Dariavach et al., 1988, supra).

It has been established that CTLA-4 acts as a negative regulator of T cell activity. For example, it has been reported that CTLA-4 deficient mice suffer from massive lymphoproliferation (Chambers et al. (1997) Immunity 7:885-895). It has also been reported that CTLA-4 blockade, using anti-CTLA-4 antibodies, augments T cell responses in vitro (Walunas et al. (1994) Immunity 1:405-413) and in vivo (Kearney (1995) J. Immunol. 155:1032-1036), exacerbates antitumor immunity (Leach (1996) Science 271:1734-1736), and enhances an induced autoimmune disease (Luhder (1998) J. Exp. Med. 187:427-432). It has also been reported that CTLA-4 has an alternative or additional impact on the initial character of the T cell immune response (Chambers (1997) Curr. Opin. Immunol. 9:396-404; Bluestone (1997) J. Immunol. 158:1989-1993; Thompson (1997) Immunity 7:445-450). This is consistent with the observation that some autoimmune patients have autoantibodies to CTLA-4. It is possible that CTLA-4 blocking antibodies have a pathogenic role in these patients (Matsui (1999) J. Immunol. 162:4328-4335). Given the ability of anti-CTLA-4 antibodies to stimulate immune responses, such antibodies are being pursued as therapeutic agents in the treatment of tumors, viral diseases and other clinical indications in which an enhanced immune response is desirable (see e.g., U.S. Pat. No. 5,811,097, No. 5,855,887 and No. 6,051,227, and PCT Publication WO 01/14424).

CTLA-4 has been demonstrated to be a ligand for B7-1 (Linsley et al. (1991) J. Exp. Med. 174:561-569) and B7-2 (Freeman et al. (1993) Science 262:909-911). The role of CTLA-4 as an immune attenuator has been Annu. Rev. Immunol hypothesized to be due to it being a competitive antagonist of CD28 costimulation via B7-1/B7-2 binding (see e.g., Thompson and Allison (1997) Immunity 7:445-450). For example, CTLA-4 has been found to have at least a 10-fold higher affinity for B7-1 and B7-2 than CD28 (Linsley et al. (1991) supra; van der Merwe et al. (1997) J. Exp. Med. 185: 393-403). The crystal structure of the CTLA-4/B7-1 complex has been described (Stamper et al. (2001) Nature 410:608-611). The interaction of CTLA-4 with B7-1 and B7-2 is reviewed in van der Merwe and Davis (2003). 21:659-684.

Given the known interaction of CTLA-4 with the ligands B7-1 and B7-2, functional anti-CTLA-4 antibodies are typically selected based on their ability to block the binding of CTLA-4 to B7-1 and/or B7-2.

SUMMARY OF THE INVENTION

The present invention provides isolated monoclonal antibodies that bind to CTLA-4 and that are capable of increasing the response of T cells to antigenic stimulation in vivo yet the antibodies do not substantially inhibit the binding of a soluble human CTLA-4 protein to cells expressing B7-1. Thus, the antibodies of the invention demonstrate that is it possible to separate the immunostimulatory function of anti-CTLA-4 antibodies from their ability to block the binding of soluble human CTLA-4 to cell-surface expressed B7-1. The soluble human CTLA-4 can be a fusion protein, such as a fusion protein comprising the extracellular domain of human CTLA-4 fused to a human immunoglobulin Fc region (referred to herein as CTLA-4-Ig). The cell-surface expressed B7-1 can be mouse B7-1.

Accordingly, in one aspect, the invention provides an isolated monoclonal antibody, or an antigen-binding portion thereof, wherein the antibody:

(a) binds to cell surface-expressed human CTLA-4;

(b) does not substantially inhibit binding of a soluble human CTLA-4 protein to cells expressing a B7-1 ligand in an in vitro assay; and (c) increases T cell responses to antigenic stimulation in vivo.

In certain embodiments, there is the proviso that the antibody is not the 1H5 antibody. In other embodiments, there is the proviso that the antibody is not the 3A4 antibody. In other embodiments, there is the proviso that the antibody is not the 6C10 antibody. In yet other embodiments, there is the proviso that the antibody is not the 1H5 or the 3A4 antibody. In a preferred embodiment, the soluble human CTLA-4 protein is a human CTLA-4-Ig fusion protein. In a preferred embodiment, the cells expressing a B7-1 ligand are cells transfected to express mouse B7-1 on their cell surface. In a preferred embodiment, the antibody is a human monoclonal antibody. Alternatively, the antibody can be a humanized or chimeric antibody. Preferably, the antibody specifically binds to human CTLA-4. The antibody can be, for example, a full-length antibody of an IgG1 isotype or an IgG4 isotype or a full-length antibody in which the Fc region has been modified to alter functional activity (e.g., antibody dependent cellular cytotoxicity activity). In other embodiments, the antibody is an antibody fragment or a single chain antibody.

Preferred antibodies of the invention inhibit binding of a soluble human CTLA-4 fusion protein to cells expressing a B7-1 ligand in an in vitro assay at least 5 fold less well than a reference antibody, 10D1, which comprises $V_H$ and $V_K$ sequences as shown in FIG. 15 and set forth in SEQ ID NOs: 50 and 51, respectively. Even more preferred antibodies inhibit binding of a soluble human CTLA-4 fusion protein to cells expressing a B7-1 ligand in an in vitro assay at least 6 fold, 7 fold, 8 fold or 9 fold, 10 fold, 15 fold or 20 fold less well than said reference antibody, 10D1.

The antibodies of the invention can increase T cell responses to antigenic stimulation in vivo, such as responses to a viral antigen or to a tumor antigen. Increased T cell responses to antigen stimulation can be evidenced by any one or more of a wide variety of indicators of T cell responses, including by not limited to increased antibody responses, increased cytokine production, increased size of particular T cell subsets (e.g., CD4 central memory T cells) and/or decreased growth of tumor cells in vivo.

In another aspect, the invention provides an isolated human monoclonal antibody, or antigen binding portion thereof, wherein the antibody cross-competes for binding to CTLA-4 with a reference antibody, wherein the reference antibody comprises:

(a) a heavy chain variable region comprising the amino acid sequence of SEQ ID NO: 28 and a light chain variable region comprising the amino acid sequence of SEQ ID NO: 31, 32, 33, or 34; or (b) a heavy chain variable region comprising the amino acid sequence of SEQ ID NO: 29 and a light chain variable region comprising the amino acid sequence of SEQ ID NO: 35; or (c) a heavy chain variable region comprising the amino acid sequence of SEQ ID NO: 30 and a light chain variable region comprising the amino acid sequence of SEQ ID NO: 36.

Thus, in one embodiment, the reference antibody comprises: a heavy chain variable region comprising the amino acid sequence of SEQ ID NO: 28 and a light chain variable region comprising the amino acid sequence of SEQ ID NO: 31, 32, 33, or 34. In another embodiment, the reference antibody comprises: a heavy chain variable region comprising the amino acid sequence of SEQ ID NO: 29 and a light chain variable region comprising the amino acid sequence of SEQ ID NO: 35. In another embodiment, the reference antibody comprises: a heavy chain variable region comprising the amino acid sequence of SEQ ID NO: 30 and a light chain variable region comprising the amino acid sequence of SEQ ID NO: 36.

In yet another aspect, the invention provides an isolated monoclonal antibody, or an antigen-binding portion thereof, comprising a heavy chain variable region that is the product of or derived from a human $V_H$ 4-39 gene, wherein the antibody specifically binds human CTLA-4. The invention also provides a monoclonal antibody, or an antigen-binding portion thereof, comprising a light chain variable region that is the product of or derived from a human $V_K$ L18 gene, wherein the antibody specifically binds human CTLA-4. Still further, the invention provides an isolated monoclonal antibody, or an antigen-binding portion thereof, comprising: a heavy chain variable region that is the product of or derived from a human $V_H$ 4-39 gene and a light chain variable region that is the product of or derived from a human $V_K$ L18 gene, wherein the antibody specifically binds human CTLA-4.

In a preferred embodiment, an antibody of the invention comprises:

(a) a heavy chain variable region CDR1 comprising SEQ ID NO: 1;

(b) a heavy chain variable region CDR2 comprising SEQ ID NO: 4;

(c) a heavy chain variable region CDR3 comprising SEQ ID NO: 7;

(d) a light chain variable region CDR1 comprising SEQ ID NO: 10, 11, 12, or 13;

(e) a light chain variable region CDR2 comprising SEQ ID NO: 16, 17, 18, or 19; and (f) a light chain variable region CDR3 comprising SEQ ID NO: 22.

In another preferred embodiment, an antibody of the invention comprises:

(a) a heavy chain variable region CDR1 comprising SEQ ID NO: 2;

(b) a heavy chain variable region CDR2 comprising SEQ ID NO: 5;

(c) a heavy chain variable region CDR3 comprising SEQ ID NO: 8;

(d) a light chain variable region CDR1 comprising SEQ ID NO: 14;

(e) a light chain variable region CDR2 comprising SEQ ID NO: 20; and (f) a light chain variable region CDR3 comprising SEQ ID NO: 26.

In another preferred embodiment, an antibody of the invention comprises:

(a) a heavy chain variable region CDR1 comprising SEQ ID NO: 3;

(b) a heavy chain variable region CDR2 comprising SEQ ID NO: 6;

(c) a heavy chain variable region CDR3 comprising SEQ ID NO: 9;

(d) a light chain variable region CDR1 comprising SEQ ID NO: 15;

(e) a light chain variable region CDR2 comprising SEQ ID NO: 21; and (f) a light chain variable region CDR3 comprising SEQ ID NO: 27.

In yet another aspect, the invention provides an isolated monoclonal antibody, or antigen binding portion thereof, comprising:

(a) a heavy chain variable region comprising an amino acid sequence selected from the group consisting of SEQ ID NOs: 28-30; and (b) a light chain variable region comprising an amino acid sequence selected from the group consisting of SEQ ID NOs: 31-36;

wherein the antibody specifically binds human CTLA-4.

In a preferred embodiment, the antibody comprises:

(a) a heavy chain variable region comprising the amino acid sequence of SEQ ID NO: 28; and (b) a light chain variable region comprising the amino acid sequence of SEQ ID NO: 31, 32, 33, or 34.

In another preferred embodiment, the antibody comprises:

(a) a heavy chain variable region comprising the amino acid sequence of SEQ ID NO: 29; and (b) a light chain variable region comprising the amino acid sequence of SEQ ID NO: 35.

In another preferred embodiment, the antibody comprises:

(a) a heavy chain variable region comprising the amino acid sequence of SEQ ID NO: 30; and (b) a light chain variable region comprising the amino acid sequence of SEQ ID NO: 36.

In another aspect, the invention provides pharmaceutical compositions comprising an isolated monoclonal antibody, or an antigen-binding portion thereof, wherein the antibody:

(a) binds to cell surface-expressed human CTLA-4;

(b) does not substantially inhibit binding of a soluble human CTLA-4 protein to cells expressing a B7-1 ligand in an in vitro assay; and (c) increases T cell responses to antigenic stimulation in vivo; and a pharmaceutically acceptable carrier.

In certain embodiments, there is the proviso that the antibody is not the 1H5 antibody. In other embodiments, there is the proviso that the antibody is not the 3A4 antibody. In yet other embodiments, there is the proviso that the antibody is not the 1H5 or the 3A4 antibody. In a preferred embodiment, the soluble human CTLA-4 protein is a human CTLA-4-Ig fusion protein. In a preferred embodiment, the cells expressing a B7-1 ligand are cells transfected to express mouse B7-1 on their cell surface. In a preferred embodiment, the antibody is a human monoclonal antibody. Alternatively, the antibody can be a humanized or chimeric antibody. Preferably, the antibody specifically binds to human CTLA-4.

Immunoconjugates, comprising the antibody, or antigen-binding portion, linked to a therapeutic agent (e.g., a cytotoxin or a radioactive isotope) are also provided, as well as pharmaceutical compositions of such immunoconjugates, comprising the immuno conjugate and a pharmaceutically acceptable carrier.

Nucleic acid molecules encoding the antibodies, or antigen-binding portions thereof, of this disclosure are also encompassed by this disclosure, as well as expression vectors comprising such nucleic acids and host cells comprising such expression vectors. Methods for preparing anti-CTLA-4 antibodies using the host cells comprising such expression vectors are also provided and may include the steps of (i) expressing the antibody in the host cell and (ii) isolating the antibody from the host cell.

In another aspect, the invention pertains to a method of increasing the response of T cells to antigenic stimulation in a subject. The method comprises administering to the subject a monoclonal antibody, or antigen binding portion thereof, wherein the monoclonal antibody, or antigen binding portion thereof, (a) binds to cell surface-expressed human CTLA-4;

(b) does not substantially inhibit binding of a soluble human CTLA-4 protein to cells expressing a B7-1 ligand in an in vitro assay; and (c) increases T cell responses to antigenic stimulation in vivo; such that the response of the T cells to antigenic stimulation is increased in the subject as compared to the response in the absence of the monoclonal antibody, or antigen binding portion thereof.

In one embodiment, the method increases the response of T cells to antigenic stimulation by a tumor antigen. In another embodiment, the method increases the response of T cells to antigenic stimulation by a viral antigen.

Preferred subjects are primates, more preferably human. In a preferred embodiment, the monoclonal antibody is a human monoclonal antibody. In other embodiments, the monoclonal antibody is a chimeric or humanized monoclonal antibody. Preferably, the monoclonal antibody inhibits binding of a soluble human CTLA-4 protein to cells expressing a B7-1 ligand in an in vitro assay at least 5 fold less well than a reference antibody, 10D1, which comprises $V_H$ and $V_K$ sequences as shown in FIG. 15 and set forth in SEQ ID NOs: 50 and 51, respectively. More preferably, the monoclonal antibody inhibits binding of a soluble human CTLA-4 protein to cells expressing a B7-1 ligand in an in vitro assay at least 6 fold, 7 fold, 8 fold, 9 fold, 10 fold, 15 fold or 20 fold less well than said reference antibody, 10D1. The increase in the response of T cells to antigen stimulation can be evidenced by any one or more of a variety of indicators of T cell responses, a nonlimiting example of which is an increased antibody response to the antigen in vivo.

In another aspect, the invention provides a method of inhibiting growth of tumor cells in a subject. The method comprises administering to the subject a monoclonal antibody, or antigen binding portion thereof, wherein the monoclonal antibody, or antigen binding portion thereof, (a) binds to cell surface-expressed human CTLA-4;

(b) does not substantially inhibit binding of a soluble human CTLA-4 protein to cells expressing a B7-1 ligand in an in vitro assay; and (c) increases T cell responses to antigenic stimulation in vivo; such that growth of tumor cells is inhibited in the subject.

Preferred subjects are primates, more preferably human subject. In a preferred embodiment, the monoclonal antibody is a human monoclonal antibody. In other embodiments, the monoclonal antibody is a chimeric or humanized monoclonal antibody. Preferably, the monoclonal antibody inhibits binding of a soluble human CTLA-4 protein to cells expressing a B7-1 ligand in an in vitro assay at least 5 fold less well than a reference antibody, 10D1, which comprises $V_H$ and $V_K$ sequences as shown in FIG. 15 and set forth in SEQ ID NOs: 50 and 51, respectively. More preferably, the monoclonal antibody inhibits binding of a soluble human CTLA-4 protein to cells expressing a B7-1 ligand in an in vitro assay at least 6 fold, 7 fold, 8 fold, 9 fold, 10 fold, 15 fold or 20 fold less well than said reference antibody 10D1.

The invention also provides a method of preparing an anti-CTLA-4 antibody comprising:

(a) providing: (i) a heavy chain variable region antibody sequence comprising a CDR1 sequence selected from the group consisting of SEQ ID NOs: 1-3, a CDR2 sequence selected from the group consisting of SEQ ID NOs: 4-6, and/or a CDR3 sequence selected from the group consisting of SEQ ID NOs: 7-9; and/or (ii) a light chain variable region antibody sequence comprising a CDR1 sequence selected from the group consisting of SEQ ID NOs: 10-15, a CDR2 sequence selected from the group consisting of SEQ ID NOs: 16-21, and/or a CDR3 sequence selected from the group consisting of SEQ ID NOs: 22-27;

(b) altering at least one amino acid residue within the heavy chain variable region antibody sequence and/or the light chain variable region antibody sequence to create at least one altered antibody sequence; and (c) expressing the altered antibody sequence as a protein.

Other features and advantages of the instant invention will be apparent from the following detailed description and examples, which should not be construed as limiting. The contents of all references, patents and published patent applications cited throughout this application are expressly incorporated herein by reference.

BRIEF DESCRIPTION OF THE DRAWINGS

FIG. 1 shows the nucleotide sequence (SEQ ID NO: 37) and amino acid sequence (SEQ ID NO: 28) of the heavy chain variable region of the 1H5 human monoclonal antibody. The CDR1 (SEQ ID NO: 1), CDR2 (SEQ ID NO: 4) and CDR3 (SEQ ID NO: 7) regions are delineated.

FIGS. 2A-2D show the nucleotide sequence (SEQ ID NO: 40, 41, 42, 43) and amino acid sequence (SEQ ID NO: 31, 32, 33, 34) of the 4 variants of the light chain variable region of the 1H5 human monoclonal antibody. The CDR1 (SEQ ID NO: 10, 11, 12, 13), CDR2 (SEQ ID NO: 16, 17, 18, 19) and CDR3 (SEQ ID NO: 22, 23, 24, 25) regions of each variant chain are delineated.

FIG. 3 shows the nucleotide sequence (SEQ ID NO: 38) and amino acid sequence (SEQ ID NO: 29) of the heavy chain variable region of the 3A4 human monoclonal antibody. The CDR1 (SEQ ID NO: 2), CDR2 (SEQ ID NO: 5) and CDR3 (SEQ ID NO: 8) regions are delineated.

FIG. 4 shows the nucleotide sequence (SEQ ID NO: 44) and amino acid sequence (SEQ ID NO: 35) of the light chain variable region of the 3A4 human monoclonal antibody. The CDR1 (SEQ ID NO: 14), CDR2 (SEQ ID NO: 20) and CDR3 (SEQ ID NO: 26) regions are delineated.

FIG. 5 shows the nucleotide sequence (SEQ ID NO: 39) and amino acid sequence (SEQ ID NO: 30) of the heavy chain variable region of the 6C10 human monoclonal antibody. The CDR1 (SEQ ID NO: 3), CDR2 (SEQ ID NO: 6) and CDR3 (SEQ ID NO: 9) regions are delineated.

FIG. 6 shows the nucleotide sequence (SEQ ID NO: 45) and amino acid sequence (SEQ ID NO: 36) of the light chain variable region of the 6C10 human monoclonal antibody. The CDR1 (SEQ ID NO: 15), CDR2 (SEQ ID NO: 21) and CDR3 (SEQ ID NO: 27) regions are delineated.

FIG. 7 shows the alignment of the amino acid sequence of the heavy chain variable region of 1H5 with the human germline $V_H$ 4-39 amino acid sequence (SEQ ID NO: 46).

FIG. 8 shows the alignment of the amino acid sequences of the heavy chain variable regions of 3A4 with the human germline $V_H$ 3-33 amino acid sequence (SEQ ID NO: 47).

FIG. 9 shows the alignment of the amino acid sequences of the heavy chain variable regions of 6C10 with the human germline $V_H$ 3-33 amino acid sequence (SEQ ID NO: 47).

FIG. 10 shows the alignment of the amino acid sequence of the light chain variable region of 1H5 with the human germline $V_k$ L-18 amino acid sequence (SEQ ID NO: 48).

FIG. 11 shows the alignment of the amino acid sequences of the light chain variable regions of 3A4 with the human germline $V_k$ L-15 amino acid sequence (SEQ ID NO: 49).

FIG. 12 shows the alignment of the amino acid sequences of the light chain variable regions of 6C10 with the human germline $V_k$ L-15 amino acid sequence (SEQ ID NO: 49).

FIG. 15 shows the heavy and light chain variable region amino acid sequences of the 10D1 human anti-CTLA-4 antibody, also shown in SEQ ID NOs: 50 and 51, respectively.

DISCLOSURE OF THE INVENTION

Figure 13:
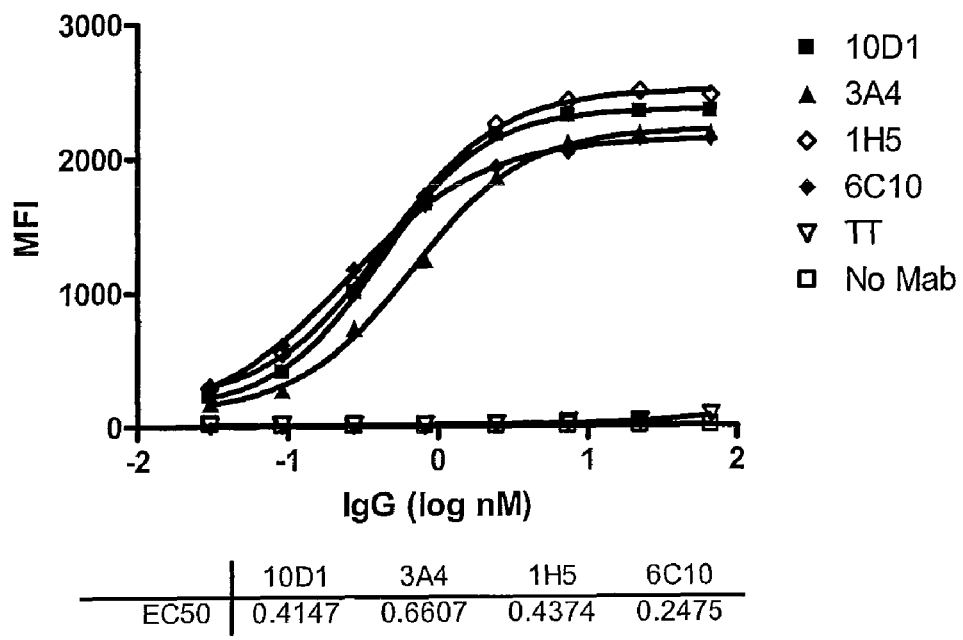
FIG. 13 is a graph showing the binding of a panel of anti-CTLA-4 monoclonal antibodies to a cell line expressing the extracellular domain of human CTLA-4, as measured by flow cytometry.

The present invention relates to isolated monoclonal antibodies that bind to CTLA-4 and that are capable of increasing the response of T cells to antigenic stimulation yet the antibodies do not substantially block the binding of CTLA-4 to B7 ligands (e.g., B7-1 and B7-2). Thus, the antibodies of the invention demonstrate that is it possible to separate the immunostimulatory function of anti-CTLA-4 antibodies from their ability to block the binding of B7 ligands. The invention provides isolated antibodies, methods of making such antibodies, immunoconjugates and bispecific molecules comprising such antibodies and pharmaceutical compositions containing the antibodies, immunconjugates or bispecific molecules of the invention. The invention also relates to methods of using the antibodies to increase the response of T cells to antigenic stimulation, for example in the treatment of cancers or infectious diseases, as well as for increasing the effectiveness of vaccinations.

In order that the present invention may be more readily understood, certain terms are first defined. Additional definitions are set forth throughout the detailed description.

The terms "cytotoxic T lymphocyte-associated antigen-4," "CTLA-4," "CTLA4," "CTLA-4 antigen" and "CD152" (see, e.g., Murata (1999) *Am. J. Pathol.* 155:453-460) are used interchangeably, and include variants, isoforms, species homologs of human CTLA-4, and analogs having at least one common epitope with CTLA-4 (see, e.g., Balzano (1992) *Int. J. Cancer Suppl.* 7:28-32). Accordingly, human antibodies of the invention may, in certain cases, cross-react with CTLA-4 from species other than human, or other proteins which are structurally related to human CTLA-4 (e.g., human CTLA-4 homologs). In other cases, the antibodies may be completely specific for human CTLA-4 and not exhibit species or other types of cross-reactivity.

The amino acid sequence of human CTLA-4 is disclosed at Genbank Accession Number NP_005205. The region of amino acids 1-37 is the leader peptide; 38-161 is the extracellular V-like domain; 162-187 is the transmembrane domain; and 188-223 is the cytoplasmic domain. The nucleotide sequence of human CTLA-4 mRNA is disclosed at NM_005214. Variants of the nucleotide sequence have been reported, including a G to A transition at position 49, a C to T transition at position 272, and an A to G transition at position 439. The amino acid sequence of mouse CTLA-4 is disclosed at Genbank Accession Number NP_033973. The region of amino acids 1-35 is the leader peptide.

The term "CTLA-4" includes variants, isoforms, homologs, orthologs and paralogs. For example, antibodies specific for CTLA-4 may, in certain cases, cross-react with CTLA-4 from species other than human. In other embodiments, the antibodies specific for human CTLA-4 may be completely specific for human CTLA-4 and may not exhibit species or other types of cross-reactivity. The term "human CTLA-4" refers to human sequence CTLA-4, such as the complete amino acid sequence of human CTLA-4 having Genbank Accession Number NP_005205. The human CTLA-4 sequence may differ from human CTLA-4 of Genbank Accession Number NP_005205 by having, for example, conserved mutations or mutations in non-conserved regions and the CTLA-4 has substantially the same biological function as the human CTLA-4 of Genbank Accession Number NP_005205. For example, a biological function of human CTLA-4 is having an epitope in the extracellular domain of CTLA-4 that is specifically bound by an antibody of the instant disclosure or a biological function of human CTLA-4 is modulation of T cell activity.

A particular human CTLA-4 sequence will generally be at least 90% identical in amino acids sequence to human CTLA-4 of Genbank Accession Number NP_005205 and contains amino acid residues that identify the amino acid sequence as being human when compared to CTLA-4 amino acid sequences of other species (e.g., murine). In certain cases, a human CTLA-4 may be at least 95%, or even at least 96%, 97%, 98%, or 99% identical in amino acid sequence to CTLA-4 of Genbank Accession Number NP_005205. In certain embodiments, a human CTLA-4 sequence will display no more than 10 amino acid differences from the CTLA-4 of Genbank Accession Number NP_005205. In certain embodiments, the human CTLA-4 may display no more than 5, or even no more than 4, 3, 2, or 1 amino acid difference from the CTLA-4 of Genbank Accession Number NP_005205. Percent identity can be determined as described herein.

The term "B7 ligand" as used herein is intended to refer to members of the B7 family of molecules that are ligands for CTLA-4 (i.e., members of the B7 family of molecules that are capable of binding CTLA-4). Examples of B7 ligands are B7-1 and B7-2. The amino acid and DNA sequences of human B7-1 (CD80) are disclosed at Genbank Accession Numbers NP_005182 and NM_005191, respectively. The amino acid and DNA sequences of human B7-2 (CD86) (isoform 1) is disclosed at Genbank Accession Numbers NP_787058 and NM_175862, respectively; the amino acid and DNA sequences of human B7-2 (CD86) (isoform 2) is disclosed at Genbank Accession Numbers NP_008820 and NM_006889, respectively. The amino acid and DNA sequences of mouse B7-1 (CD80) are disclosed at Genbank Accession Numbers NP_033985 and NM_009855, respectively. The amino acid and DNA sequences of mouse B7-2 (CD86) are disclosed at Genbank Accession Numbers NP_062261 and NM_019388, respectively.

The term "immune response" refers to the action of, for example, lymphocytes, antigen presenting cells, phagocytic cells, granulocytes, and soluble macromolecules produced by the above cells or the liver (including antibodies, cytokines, and complement) that results in selective damage to, destruction of, or elimination from the human body of invading pathogens, cells or tissues infected with pathogens, cancerous cells, or, in cases of autoimmunity or pathological inflammation, normal human cells or tissues.

A "signal transduction pathway" refers to the biochemical relationship between a variety of signal transduction molecules that play a role in the transmission of a signal from one portion of a cell to another portion of a cell. As used herein, the phrase "cell surface receptor" includes, for example, molecules and complexes of molecules capable of receiving a signal and the transmission of such a signal across the plasma membrane of a cell. An example of a "cell surface receptor" of the present disclosure is the CTLA-4 protein.

The term "antibody" as referred to herein includes whole antibodies and any antigen binding fragment (i.e., "antigen-binding portion") or single chains thereof. An "antibody" refers to a glycoprotein comprising at least two heavy (H) chains and two light (L) chains inter-connected by disulfide bonds, or an antigen binding portion thereof. Each heavy chain is comprised of a heavy chain variable region (abbreviated herein as $V_H$) and a heavy chain constant region. The heavy chain constant region is comprised of three domains, $C_H1$, $C_H2$ and $C_H3$. Each light chain is comprised of a light chain variable region (abbreviated herein as $V_K$) and a light chain constant region. The light chain constant region is comprised of one domain, $C_K$. The $V_H$ and $V_K$ regions can be further subdivided into regions of hypervariability, termed complementarity determining regions (CDR), interspersed with regions that are more conserved, termed framework regions (FR). Each $V_H$ and $V_K$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system.

The term "antigen-binding portion" of an antibody (or simply "antibody portion"), as used herein, refers to one or more fragments of an antibody that retain the ability to specifically bind to an antigen (e.g., CTLA-4). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the $V_K$ $V_H$, $C_K$ and $C_H1$ domains; (ii) a F(ab')$_2$ fragment, a bivalent fragment comprising two Fab fragments linked by a disulfide bridge at the hinge region; (iii) a Fab' fragment, which is essentially an Fab with part of the hinge region (see, FUNDAMENTAL IMMUNOLOGY (Paul ed., 3.sup.rd ed. 1993); (iv) a Fd fragment consisting of the $V_H$ and $C_H1$ domains; (v) a Fv fragment consisting of the $V_K$ and $V_H$ domains of a single arm of an antibody, (vi) a dAb fragment (Ward et al., (1989) *Nature* 341:544-546), which consists of a $V_H$ domain; (vii) an isolated complementarity determining region (CDR); and (viii) a nanobody, a heavy chain variable region containing a single variable domain and two constant domains Furthermore, although the two domains of the Fv fragment, $V_K$ and $V_H$, are coded for by separate genes, they can be joined, using recombinant methods, by a synthetic linker that enables them to be made as a single protein chain in which the $V_K$ and $V_H$ regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies.

An "isolated antibody", as used herein, is intended to refer to an antibody that is substantially free of other antibodies having different antigenic specificities (e.g., an isolated antibody that specifically binds CTLA-4 is substantially free of antibodies that specifically bind antigens other than CTLA-4). An isolated antibody that specifically binds CTLA-4 may, however, have cross-reactivity to other antigens, such as CTLA-4 molecules from other species. Moreover, an isolated antibody may be substantially free of other cellular material and/or chemicals.

The terms "monoclonal antibody" or "monoclonal antibody composition" as used herein refer to a preparation of antibody molecules of single molecular composition. A monoclonal antibody composition displays a single binding specificity and affinity for a particular epitope.

The term "human antibody", as used herein, is intended to include antibodies having variable regions in which both the framework and CDR regions are derived from human germline immunoglobulin sequences. Furthermore, if the antibody contains a constant region, the constant region also is derived from human germline immunoglobulin sequences. The human antibodies of this disclosure may include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences.

The term "human monoclonal antibody" refers to antibodies displaying a single binding specificity, which have variable regions in which both the framework and CDR regions are derived from human germline immunoglobulin sequences. In one embodiment, the human monoclonal antibodies are produced by a hybridoma which includes a B cell obtained from a transgenic nonhuman animal, e.g., a transgenic mouse, having a genome comprising a human heavy chain transgene and a light chain transgene fused to an immortalized cell.

The term "recombinant human antibody", as used herein, includes all human antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom (described further below), (b) antibodies isolated from a host cell transformed to express the human antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies have variable regions in which the framework and CDR regions are derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the $V_H$ and $V_K$ regions of the recombinant antibodies are sequences that, while derived from and related to human germline $V_H$ and $V_K$ sequences, may not naturally exist within the human antibody germline repertoire in vivo.

As used herein, "isotype" refers to the antibody class (e.g., IgM or IgG1) that is encoded by the heavy chain constant region genes.

The phrases "an antibody recognizing an antigen" and "an antibody specific for an antigen" are used interchangeably herein with the term "an antibody which binds specifically to an antigen."

The term "human antibody derivatives" refers to any modified form of the human antibody, e.g., a conjugate of the antibody and another agent or antibody.

The term "humanized antibody" is intended to refer to antibodies in which CDR sequences derived from the germline of another mammalian species, such as a mouse, have been grafted onto human framework sequences. Additional framework region modifications may be made within the human framework sequences.

The term "chimeric antibody" is intended to refer to antibodies in which the variable region sequences are derived from one species and the constant region sequences are derived from another species, such as an antibody in which the variable region sequences are derived from a mouse antibody and the constant region sequences are derived from a human antibody.

As used herein, an antibody that "specifically binds to human CTLA-4" is intended to refer to an antibody that binds to human CTLA-4 (and possibly CTLA-4 from one or more non-human species) but does not substantially bind to non-CTLA-4 proteins. In certain embodiments, an antibody of the instant disclosure specifically binds to human CTLA-4 of Genbank Accession Number NP_005205, or a variant thereof. Preferably, the antibody binds to human CTLA-4 with a $K_D$ of $1 \times 10^{-7}$ M or less, more preferably $5 \times 10^{-8}$ M or less, more preferably $3 \times 10^{-8}$ M or less, more preferably $1 \times 10^{-8}$ M or less, even more preferably $5 \times 10^{-9}$ M or less.

The term "does not substantially bind" to a protein or cells, as used herein, means does not bind or does not bind with a high affinity to the protein or cells, i.e. binds to the protein or cells with a $K_D$ of $1 \times 10^{-6}$ M or more, more preferably $1 \times 10^{-5}$ M or more, more preferably $1 \times 10^{-4}$ M or more, more preferably $1 \times 10^{-3}$ M or more, even more preferably $1 \times 10^{-2}$ M or more.

The term "$K_{assoc}$" or "$K_a$", as used herein, is intended to refer to the association rate of a particular antibody-antigen interaction, whereas the term "$K_{dis}$" or "$K_d$," as used herein, is intended to refer to the dissociation rate of a particular antibody-antigen interaction. The term "$K_D$", as used herein, is intended to refer to the dissociation constant, which is obtained from the ratio of $K_d$ to $K_a$ (i.e., $K_d/K_a$) and is expressed as a molar concentration (M). $K_D$ values for antibodies can be determined using methods well established in the art. A preferred method for determining the $K_D$ of an antibody is by using surface plasmon resonance, preferably using a biosensor system such as a Biacore® system.

As used herein, the term "high affinity" for an IgG antibody refers to an antibody having a $K_D$ of $1 \times 10^{-7}$ M or less, more preferably $5 \times 10^{-8}$ M or less, even more preferably $1 \times 10^{-8}$ M or less, even more preferably $5 \times 10^{-9}$ M or less and even more preferably $1 \times 10^{-9}$ M or less for a target antigen. However, "high affinity" binding can vary for other antibody isotypes. For example, "high affinity" binding for an IgM isotype refers to an antibody having a $K_D$ of $10^{-6}$ M or less, more preferably $10^{-7}$ M or less, even more preferably $10^{-8}$ M or less.

As used herein, the term "subject" includes any human or nonhuman animal. The term "nonhuman animal" includes all vertebrates, e.g., mammals and non-mammals, such as non-human primates, sheep, dogs, cats, horses, cows, chickens, amphibians, reptiles, etc.

Various aspects of this disclosure are described in further detail in the following subsections.

Functional Properties of Anti-CTLA-4 Antibodies

The antibodies of the invention are characterized, at least in part, by particular functional features or properties of the antibodies. For example, the invention provides an isolated monoclonal antibody, or an antigen-binding portion thereof, wherein the antibody:

(a) binds to cell surface-expressed human CTLA-4;

(b) does not substantially inhibit binding of a soluble human CTLA-4 protein to cells expressing a B7-1 ligand in an in vitro assay; and (c) increases T cell responses to antigenic stimulation in vivo.

Preferably, an antibody of the invention binds to CTLA-4 with high affinity, for example with a $K_D$ of $10^{-7}$ M or less, more preferably with a $K_D$ of $10^{-8}$ M or less or $10^{-9}$ M or less or even $10^{-10}$ M or less. In a preferred embodiment, the antibody binds to human CTLA-4.

Furthermore, the antibodies of the invention can be referred to as "non-blocking" antibodies, meaning that the antibodies do not substantially inhibit the binding of a soluble human CTLA-4 protein to cells expressing a B7-1 ligand in an in vitro assay. In various embodiments, an antibody of the invention does not substantially inhibit the binding of a soluble human CTLA-4 protein to cells expressing B7-1, does not substantially inhibit the binding of a soluble human CTLA-4 protein to cells expressing B7-2, or does not substantially inhibit the binding of a soluble human CTLA-4 protein to both B7-1 and B7-2.

A nonlimiting example of a soluble human CTLA-4 protein that can be used to test the inhibitory ability of antibodies of the invention is a CTLA-4-Ig fusion protein comprising the extracellular domain of human CTLA-4 fused to the Fc region of a human immunoglobulin. The preparation and use of such Ig fusion proteins is well-established in the art. A suitable CTLA4-Ig fusion protein is commercially available from R&D Systems (Cat #325-CT-200 or 325-CT-200/CF), which product is particularly preferred for use in the invention. For example, when testing whether an antibody is "non-blocking", if the antibody does not substantially inhibit binding of the R&D Systems human CTLA-4-Ig fusion protein to cells expressing a B7-1 ligand in an in vitro assay then than the antibody is considered to be a "non-blocking" antibody in accordance with the current invention (regardless of whether the antibody is able to inhibit the binding of another human CTLA-4-Ig fusion protein preparation to cells expressing a B7-1 ligand).

Analysis of the R&D Systems CTLA-4-Ig fusion protein determined that it contains an alanine residue at amino acid position 111 of the mature protein (amino acid position 147 of Genbank Accession No. NP_005205). An additional or alternative example of a CTLA4-Ig fusion protein that is suitable for use in the in vitro assays of the invention is a CTLA4-Ig fusion protein that is essentially the same as the R & D Systems CTLA4-Ig except that it contains a threonine at amino acid position 111 of the mature protein (amino acid position 147 of Genbank Accession No. NP_005205). Furthermore, it has been determined that the presence of threonine at position 111 of the mature protein results in an additional carbohydrate residue in the $Thr_{111}$ material as compared to the $Ala_{111}$ material. However, either the $Thr_{111}$ form of CTLA-4-Ig or the $Ala_{111}$ form of CTLA-4-Ig is suitable for use in the current invention.

Alternatively, the extracellular domain alone of CTLA-4 can be used as a soluble human CTLA-4 protein, or other forms of fusion proteins comprising the extracellular domain of CTLA-4 can be used.

A nonlimiting example of a cell expressing a B7-1 ligand that can be used to test the inhibitory ability of antibodies of the invention is a cell of a mouse fibroblast cell line transfected to express mouse B7-1 on its cell surface, such as mouse fibroblast Ltk-cells (European Collection of Cell Cultures ECACC No. 85011432) transfected to express mouse B7-1 on their cell surface. An example of such a transfected cell line is the 4D3 cell line described in the Examples herein and also in U.S. Patent Publication No. 2002/0086014 (in which the cell line is referred to as LtkmB7.1). Other suitable cells include, for example, CHO cells transfected to express recombinant human or mouse B7-1.

The term "does not substantially inhibit the binding" is intended to mean that the antibody does not inhibit the binding of a soluble human CTLA-4 protein to cells expressing a B7-1 ligand at a concentration at which the previously known anti-CTLA-4 antibody 10D1 is capable of inhibiting such binding. The human monoclonal 10D1 antibody is described in detail in PCT Publication WO 01/14424, as well as U.S. Pat. No. 6,984,720 and U.S. Patent Publication No. 20020086014, the contents of each of which are expressly incorporated by reference. The 10D1 antibody comprises VH and VK regions having the amino acid sequences shown in FIG. 15.

Preferred antibodies of the invention inhibit binding of a soluble human CTLA-4 fusion protein to cells expressing a B7-1 ligand in an in vitro assay at least 5 fold less well than a reference antibody, 10D1, which comprises $V_H$ and $V_K$ sequences as set forth in SEQ ID NOs: 50 and 51, respectively. More preferred antibodies of the invention inhibit binding of a soluble human CTLA-4 protein to cells expressing a B7-1 ligand in an in vitro assay at least 5 fold, 6 fold, 7 fold, 8 fold, 9 fold, 10 fold, 15 fold or 20 fold less well than a reference antibody, 10D1, which comprises $V_H$ and $V_K$ sequences as set forth in SEQ ID NOs: 50 and 51, respectively. In still other embodiments, an antibody of the invention inhibits binding of a soluble human CTLA-4 fusion protein to cells expressing a B7-1 ligand in an in vitro assay at least 30 fold less well, or 40-fold less well, or 50-fold less well, or 60-fold less well, or 70-fold less well, or 80-fold less well, or 90-fold less well, or 100-fold less well than a reference antibody, 10D1, which comprises $V_H$ and $V_K$ sequences as set forth in SEQ ID NOs: 50 and 51, respectively.

Still further, the antibodies of the invention are immunostimulatory antibodies, meaning that the antibodies increase the response of T cells to antigenic stimulation in vivo, relative to the response of the T cells to the antigenic stimulation in the absence of the CTLA-4 antibody or in the presence of a control antibody. The antigen stimulation to which the T cell response is increased can be, for example, stimulation by a tumor antigen or by an antigen from a pathogen (e.g., a viral or bacterial, antigen). The ability of anti-CTLA-4 antibodies to increase the response of T cells to antigenic stimulation has been described in the art (see e.g., Walunas et al. (1994) *Immunity* 1:405-413; Kearney (1995) *J. Immunol.* 1.155: 1032-1036; Leach (1996) *Science* 271:1734-1736; Keler et al. (2003) *J. Immunol.* 171:6251-6259; U.S. Pat. No. 5,811, 097, U.S. Pat. No. 5,855,887 and U.S. Pat. No. 6,051,227, and PCT Publication WO 01/14424) and can be evaluated using any one of a number of different in vitro or in vivo assays described in the aforementioned publications.

Increases in T cell responses to antigen stimulation can be evidenced by any one or more of a wide variety of indicators of T cell responses, including by not limited to increased antibody responses, increased cytokine production, increased size of particular T cell subsets (e.g., CD4 central memory T cells) and/or decreased growth of tumor cells in vivo. Other assays that can be performed to evaluate T cell responses to antigen stimulation include T cell proliferation assays and ELISPOT assays, e.g., to identify and enumerate cytokine secreting cells at the single cell level.

An example of an in vivo system by which to evaluate the ability of an antibody of the invention to increase the response of T cells to antigenic stimulation is antibody treatment of cynomolgus monkeys that are coadministered an immunostimulant agents (e.g., a cellular or proteinaceous vaccine), as described in detail in Example 4. The use of an anti-CTLA-4 antibody in combination with a vaccine in vivo in cynomolgus monkeys is also described in Keler et al. (2003) *J. Immunol.* 171:6251-6259.

An example of another assay by which to evaluate the ability of an antibody of the invention to increase the response of T cells to antigenic stimulation is a tumor growth inhibition assay. Briefly, tumor cells (such as MC38 colon carcinoma cells or B16 melanoma cells) are injected into mice with a test antibody of the invention or an isotype matched control antibody. (For testing antibodies that bind human CTLA-4, a mouse is used that is transgenic for human CTLA-4 such that the test antibody interacts with the human CTLA-4 expressed in the mice). The effect of the test antibody on growth of the tumor cells in the mice is evaluated, as compared to the control antibody. Test antibodies that result in less tumor growth in the mice as compared to the control antibody are identified as antibodies that increase the response of T cells to antigenic stimulation.

In certain embodiments, there is the proviso that the monoclonal antibody of the invention is not the 1H5 antibody. In other embodiments, there is the proviso that the monoclonal antibody of the invention is not the 3A4 antibody. In yet other embodiments, there is the proviso that the monoclonal antibody of the invention is not the 1H5 or the 3A4 antibody. These provisos can be applied to, for example, antibody compositions of the invention, pharmaceutical compositions of the invention comprising antibody compositions of the invention or methods of the invention that use antibody compositions of the invention, or any other aspects of the invention that comprise an antibody composition of the invention. The preparation and partial characterization of the 3A4 antibody is described in PCT Publication WO 01/14424, as well as in U.S. Pat. No. 6,984,720 and U.S. Patent Publication No. 20020086014. The preparation and partial characterization of the 1H5 antibody is described in PCT Publication WO 02/43478, as well as in U.S. Pat. No. 7,041,870 and U.S. Patent Publication No. 20020199213.

Monoclonal Antibodies 1H5, 3A4 and 6C10

Preferred antibodies of the invention include the human monoclonal antibodies 1H5, 3A4 and 6C10, isolated and structurally characterized as described in Examples 1 and 2. The $V_H$ amino acid sequences of 1H5, 3A4 and 6C10 are shown in SEQ ID NOs: 28, 29 and 30, respectively. The $V_K$ amino acid sequences of 1H5, 3A4 and 6C10 are shown in SEQ ID NOs: 31-36.

Given that each of these antibodies can bind to CTLA-4, the $V_H$ and $V_K$ sequences can be "mixed and matched" to create other anti-CTLA-4 binding molecules of this disclosure. CTLA-4 binding of such "mixed and matched" antibodies can be tested using the binding assays described herein and in the Examples (e.g., ELISA or flow cytometry). Preferably, when $V_H$ and $V_K$ chains are mixed and matched, a $V_H$ sequence from a particular $V_H/V_K$ pairing is replaced with a structurally similar $V_H$ sequence. Likewise, preferably a $V_K$ sequence from a particular $V_H/V_K$ pairing is replaced with a structurally similar $V_K$ sequence.

Accordingly, in one aspect, this disclosure provides an isolated monoclonal antibody, or antigen binding portion thereof comprising:

(a) a heavy chain variable region comprising an amino acid sequence selected from the group consisting of SEQ ID NOs: 28-30; and (b) a light chain variable region comprising an amino acid sequence selected from the group consisting of SEQ ID NOs: 31-36;

wherein the antibody specifically binds CTLA-4, preferably human CTLA-4.

Preferred heavy and light chain combinations include:

(a) a heavy chain variable region comprising the amino acid sequence of SEQ ID NO: 28 and a light chain variable region comprising the amino acid sequence of SEQ ID NO: 31-34; or (b) a heavy chain variable region comprising the amino acid sequence of SEQ ID NO: 29 and a light chain variable region comprising the amino acid sequence of SEQ ID NO: 35; or (c) a heavy chain variable region comprising the amino acid sequence of SEQ ID NO: 30 and a light chain variable region comprising the amino acid sequence of SEQ ID NO: 36.

In another aspect, this disclosure provides antibodies that comprise the heavy chain and light chain CDR1s, CDR2s and CDR3s of 1H5, 3A4 and 6C10, or combinations thereof. The amino acid sequences of the $V_H$ CDR1s of 1H5, 3A4 and 6C10 are shown in SEQ ID NOs: 1-3, respectively. The amino acid sequences of the $V_H$ CDR2s of 1H5, 3A4 and 6C10 are shown in SEQ ID NOs: 4-6, respectively. The amino acid sequences of the $V_H$ CDR3s of 1H5, 3A4 and 6C10 are shown in SEQ ID NOs: 7-9, respectively. The amino acid sequences of the $V_K$ CDR1s of 1H5, 3A4 and 6C10 are shown in SEQ ID NOs: 10-15, respectively. The amino acid sequences of the $V_K$ CDR2s of 1H5, 3A4 and 6C10 are shown in SEQ ID NOs: 16-21, respectively. The amino acid sequences of the $V_K$ CDR3 s of 1H5, 3A4 and 6C10 are shown in SEQ ID NOs: 22-27, respectively. The CDR regions are delineated using the Kabat system (Kabat, E. A., et al. (1991) Sequences of Proteins of Immunological Interest, Fifth Edition, U.S. Department of Health and Human Services, NIH Publication No. 91-3242).

Given that each of these antibodies can bind to CTLA-4 and that antigen-binding specificity is provided primarily by the CDR1, CDR2, and CDR3 regions, the $V_H$ CDR1, CDR2, and CDR3 sequences and $V_K$ CDR1, CDR2, and CDR3 sequences can be "mixed and matched" (i.e., CDRs from different antibodies can be mixed and match, although each antibody must contain a $V_H$ CDR1, CDR2, and CDR3 and a $V_K$ CDR1, CDR2, and CDR3) to create other anti-CTLA-4 binding molecules of this disclosure. CTLA-4 binding of such "mixed and matched" antibodies can be tested using the binding assays described herein and in the Examples (e.g., ELISAs, Biacore® analysis). Preferably, when $V_H$ CDR sequences are mixed and matched, the CDR1, CDR2 and/or CDR3 sequence from a particular $V_H$ sequence is replaced with a structurally similar CDR sequence(s). Likewise, when $V_K$ CDR sequences are mixed and matched, the CDR1, CDR2 and/or CDR3 sequence from a particular $V_K$ sequence preferably is replaced with a structurally similar CDR sequence(s). It will be readily apparent to the ordinarily skilled artisan that novel $V_H$ and $V_K$ sequences can be created by substituting one or more $V_H$ and/or $V_K$ CDR region sequences with structurally similar sequences from the CDR sequences disclosed herein for monoclonal antibodies 1H5, 3A4 and 6C10.

Accordingly, in another aspect, this disclosure provides an isolated monoclonal antibody, or antigen binding portion thereof comprising:

(a) a heavy chain variable region CDR1 comprising an amino acid sequence selected from the group consisting of SEQ ID NOs: 1-3;

(b) a heavy chain variable region CDR2 comprising an amino acid sequence selected from the group consisting of SEQ ID NOs: 4-6;

(c) a heavy chain variable region CDR3 comprising an amino acid sequence selected from the group consisting of SEQ ID NOs: 7-9;

(d) a light chain variable region CDR1 comprising an amino acid sequence selected from the group consisting of SEQ ID NOs: 10-15;

(e) a light chain variable region CDR2 comprising an amino acid sequence selected from the group consisting of SEQ ID NOs: 16-21; and (f) a light chain variable region CDR3 comprising an amino acid sequence selected from the group consisting of SEQ ID NOs: 22-27;

wherein the antibody specifically binds CTLA-4, preferably human CTLA-4.

In a preferred embodiment, the antibody comprises:

(a) a heavy chain variable region CDR1 comprising SEQ ID NO: 1;

(b) a heavy chain variable region CDR2 comprising SEQ ID NO: 4;

(c) a heavy chain variable region CDR3 comprising SEQ ID NO: 7;

(d) a light chain variable region CDR1 comprising SEQ ID NO: 10, 11, 12, or 13;

(e) a light chain variable region CDR2 comprising SEQ ID NO: 16, 17, 18, or 19; and (f) a light chain variable region CDR3 comprising SEQ ID NO: 22, 23, 24, or 25.

In another preferred embodiment, the antibody comprises:

(a) a heavy chain variable region CDR1 comprising SEQ ID NO: 2;

(b) a heavy chain variable region CDR2 comprising SEQ ID NO: 5;

(c) a heavy chain variable region CDR3 comprising SEQ ID NO: 8;

(d) a light chain variable region CDR1 comprising SEQ ID NO: 14;

(e) a light chain variable region CDR2 comprising SEQ ID NO: 20; and (f) a light chain variable region CDR3 comprising SEQ ID NO: 26.

In another preferred embodiment, the antibody comprises:

(a) a heavy chain variable region CDR1 comprising SEQ ID NO: 3;

(b) a heavy chain variable region CDR2 comprising SEQ ID NO: 6;

(c) a heavy chain variable region CDR3 comprising SEQ ID NO: 9;

(d) a light chain variable region CDR1 comprising SEQ ID NO: 15;

(e) a light chain variable region CDR2 comprising SEQ ID NO: 21; and (f) a light chain variable region CDR3 comprising SEQ ID NO: 27.

It is well known in the art that the CDR3 domain, independently from the CDR1 and/or CDR2 domain(s), alone can determine the binding specificity of an antibody for a cognate antigen and that multiple antibodies can predictably be generated having the same binding specificity based on a common CDR3 sequence. See, for example, Klimka et al., *British J. of Cancer* 83(2):252-260 (2000) (describing the production of a humanized anti-CD30 antibody using only the heavy chain variable domain CDR3 of murine anti-CD30 antibody Ki-4); Beiboer et al., *J. Mol. Biol.* 296:833-849 (2000) (describing recombinant epithelial glycoprotein-2 (EGP-2) antibodies using only the heavy chain CDR3 sequence of the parental murine MOC-31 anti-EGP-2 antibody); Rader et al., *Proc. Natl. Acad. Sci. U.S.A.* 95:8910-8915 (1998) (describing a panel of humanized anti-integrin $\alpha_v\beta_3$ antibodies using a heavy and light chain variable CDR3 domain of a murine anti-integrin $\alpha_v\beta_3$ antibody LM609 wherein each member antibody comprises a distinct sequence outside the CDR3 domain and capable of binding the same epitope as the parent murine antibody with affinities as high or higher than the parent murine antibody); Barbas et al., *J. Am. Chem. Soc.* 116:2161-2162 (1994) (disclosing that the CDR3 domain provides the most significant contribution to antigen binding); Barbas et al., *Proc. Natl. Acad. Sci. U.S.A.* 92:2529-2533 (1995) (describing the grafting of heavy chain CDR3 sequences of three Fabs (SI-1, SI-40, and SI-32) against human placental DNA onto the heavy chain of an anti-tetanus toxoid Fab thereby replacing the existing heavy chain CDR3 and demonstrating that the CDR3 domain alone conferred binding specificity); Ditzel et al., *J. Immunol.* 157:739-749 (1996) (describing grafting studies wherein transfer of only the heavy chain CDR3 of a parent polyspecific Fab LNA3 to a heavy chain of a monospecific IgG tetanus toxoid-binding Fab p313 antibody was sufficient to retain binding specificity of the parent Fab); Berezov et al., *BIAjournal* 8:Scientific Review 8 (2001) (describing peptide mimetics based on the CDR3 of an anti-HER2 monoclonal antibody; Igarashi et al., *J. Biochem (Tokyo)* 117:452-7 (1995) (describing a 12 amino acid synthetic polypeptide corresponding to the CDR3 domain of an anti-phosphatidylserine antibody); Bourgeois et al., *J. Virol* 72:807-10 (1998) (showing that a signal peptide derived form the heavy chain CDR3 domain of an anti-respiratory syncytial virus (RSV) antibody was capable of neutralizing the virus in vitro); Levi et al., *Proc. Natl. Acad. Sci. U.S.A.* 90:4374-8 (1993) (describing a peptide based on the heavy chain CDR3 domain of a murine anti-HIV antibody); Polymenis and Stoller, *J. Immunol.* 152:5218-5329 (1994) (describing enabling binding of an scFv by grafting the heavy chain CDR3 region of a Z-DNA-binding antibody) and Xu and Davis, *Immunity* 13:37-45 (2000) (describing that diversity at the heavy chain CDR3 is sufficient to permit otherwise identical IgM molecules to distinguish between a variety of hapten and protein antigens). See also, U.S. Pat. Nos. 6,951,646; 6,914,128; 6,090,382; 6,818,216; 6,156,313; 6,827,925; 5,833,943; 5,762,905 and 5,760,185, describing patented antibodies defined by a single CDR domain. Each of these references is hereby incorporated by reference in its entirety.

Accordingly, the present disclosure provides monoclonal antibodies comprising one or more heavy and/or light chain CDR3 domains from an antibody derived from a human or non-human animal, wherein the monoclonal antibody is capable of specifically binding to CTLA-4. Within certain aspects, the present disclosure provides monoclonal antibodies comprising one or more heavy and/or light chain CDR3 domain from a non-human antibody, such as a mouse or rat antibody, wherein the monoclonal antibody is capable of specifically binding to CTLA-4. Within some embodiments, such inventive antibodies comprising one or more heavy and/or light chain CDR3 domain from a non-human antibody (a) are capable of competing for binding with; (b) retain the functional characteristics; (c) bind to the same epitope; and/or (d) have a similar binding affinity as the corresponding parental non-human antibody.

Within other aspects, the present disclosure provides monoclonal antibodies comprising one or more heavy and/or light chain CDR3 domain from a human antibody, such as, for example, a human antibody obtained from a non-human animal, wherein the human antibody is capable of specifically binding to CTLA-4. Within other aspects, the present disclosure provides monoclonal antibodies comprising one or more heavy and/or light chain CDR3 domain from a first human antibody, such as, for example, a human antibody obtained from a non-human animal, wherein the first human antibody is capable of specifically binding to CTLA-4 and wherein the CDR3 domain from the first human antibody replaces a CDR3 domain in a human antibody that is lacking binding specificity for CTLA-4 to generate a second human antibody that is capable of specifically binding to CTLA-4. Within some embodiments, such inventive antibodies comprising one or more heavy and/or light chain CDR3 domain from the first human antibody (a) are capable of competing for binding with; (b) retain the functional characteristics; (c) bind to the same epitope; and/or (d) have a similar binding affinity as the corresponding parental first human antibody.

Antibodies Having Particular Germline Sequences

In certain embodiments, an antibody of this disclosure comprises a heavy chain variable region from a particular germline heavy chain immunoglobulin gene and/or a light chain variable region from a particular germline light chain immunoglobulin gene.

For example, in a preferred embodiment, this disclosure provides an isolated monoclonal antibody, or an antigen-binding portion thereof, comprising a heavy chain variable region that is the product of or derived from a human $V_H$ 4-39 gene or a human $V_H$ 3-33 gene, wherein the antibody specifically binds CTLA-4. In another preferred embodiment, this disclosure provides an isolated monoclonal antibody, or an antigen-binding portion thereof, comprising a light chain variable region that is the product of or derived from a human $V_K$ L15 gene or a human $V_K$ L18 gene, wherein the antibody specifically binds CTLA-4. In yet another preferred embodiment, this disclosure provides an isolated monoclonal antibody, or antigen-binding portion thereof, wherein the antibody comprises a heavy chain variable region that is the product of or derived from a human $V_H$ 4-39 gene and comprises a light chain variable region that is the product of or derived from a human $V_K$ L18 gene, wherein the antibody specifically binds to CTLA-4, preferably human CTLA-4. In yet another preferred embodiment, this disclosure provides an isolated monoclonal antibody, or antigen-binding portion thereof, wherein the antibody comprises a heavy chain variable region that is the product of or derived from a human $V_H$ 3-33 gene and comprises a light chain variable region that is the product of or derived from a human $V_K$ L15 gene, wherein the antibody specifically binds to CTLA-4, preferably human CTLA-4.

Antibodies of the invention comprising a heavy chain of a particular $V_H$ germline sequence and/or comprising a light chain of a particular $V_K$ germline sequence also may possess one or more of the functional characteristics of the antibodies described in detail herein, such as:

(a) binding to cell surface-expressed human CTLA-4;

(b) not substantially inhibiting binding of a soluble human CTLA-4 protein to cells expressing a B7-1 ligand in an in vitro assay; and (c) increasing T cell responses to antigenic stimulation in vivo.

An example of an antibody having $V_H$ and $V_K$ of $V_H$ 4-39 and $V_K$ L18, respectively, is the 1H5 antibody. Examples of antibodies having $V_H$ and $V_K$ of $V_H$ 3-33 and $V_K$ L15, respectively, are the 3A4 and 6C10 antibodies.

As used herein, a human antibody comprises heavy or light chain variable regions that is "the product of" or "derived from" a particular germline sequence if the variable regions of the antibody are obtained from a system that uses human germline immunoglobulin genes. Such systems include immunizing a transgenic mouse carrying human immunoglobulin genes with the antigen of interest or screening a human immunoglobulin gene library displayed on phage with the antigen of interest. A human antibody that is "the product of" or "derived from" a human germline immunoglobulin sequence can be identified as such by comparing the amino acid sequence of the human antibody to the amino acid sequences of human germline immunoglobulins and selecting the human germline immunoglobulin sequence that is closest in sequence (i.e., greatest % identity) to the sequence of the human antibody. A human antibody that is "the product of" or "derived from" a particular human germline immunoglobulin sequence may contain amino acid differences as compared to the germline sequence, due to, for example, naturally-occurring somatic mutations or intentional introduction of site-directed mutation. However, a selected human antibody typically is at least 90% identical in amino acids sequence to an amino acid sequence encoded by a human germline immunoglobulin gene and contains amino acid residues that identify the human antibody as being human when compared to the germline immunoglobulin amino acid sequences of other species (e.g., murine germline sequences). In certain cases, a human antibody may be at least 95%, or even at least 96%, 97%, 98%, or 99% identical in amino acid sequence to the amino acid sequence encoded by the germline immunoglobulin gene. Typically, a human antibody derived from a particular human germline sequence will display no more than 10 amino acid differences from the amino acid sequence encoded by the human germline immunoglobulin gene. In certain cases, the human antibody may display no more than 5, or even no more than 4, 3, 2, or 1 amino acid difference from the amino acid sequence encoded by the germline immunoglobulin gene.

Homologous Antibodies

In yet another embodiment, an antibody of this disclosure comprises heavy and light chain variable regions comprising amino acid sequences that are homologous to the amino acid sequences of the preferred antibodies described herein, and wherein the antibodies retain the desired functional properties of the anti-CTLA-4 antibodies of this disclosure.

For example, this disclosure provides an isolated monoclonal antibody, or antigen binding portion thereof, comprising a heavy chain variable region and a light chain variable region, wherein:

(a) the heavy chain variable region comprises an amino acid sequence that is at least 80% homologous to an amino acid sequence selected from the group consisting of SEQ ID NOs: 28-30;

(b) the light chain variable region comprises an amino acid sequence that is at least 80% homologous to an amino acid sequence selected from the group consisting of SEQ ID NOs: 31-36;

(c) the antibody specifically binds to human CTLA-4.

Additionally or alternatively, the antibody may possess one or more of the functional properties of the antibodies described in detail herein; for example the antibody may possess the following properties:

(a) binding to cell surface-expressed human CTLA-4;

(b) not substantially inhibiting binding of a soluble human CTLA-4 protein to cells expressing a B7-1 ligand in an in vitro assay; and (c) increasing T cell responses to antigenic stimulation in vivo.

In various embodiments, the antibody can be, for example, a human antibody, a humanized antibody or a chimeric antibody.

In other embodiments, the $V_H$ and/or $V_K$ amino acid sequences may be 85%, 90%, 95%, 96%, 97%, 98% or 99% homologous to the sequences set forth above. An antibody having $V_H$ and $V_K$ regions having high (i.e., 80% or greater) homology to the $V_H$ and $V_K$ regions of the sequences set forth above, can be obtained by mutagenesis (e.g., site-directed or PCR-mediated mutagenesis) of nucleic acid molecules encoding SEQ ID NOs: 37-39 and/or 40-45, followed by testing of the encoded altered antibody for retained function (i.e., the functions set forth above) using the functional assays described herein.

As used herein, the percent homology between two amino acid sequences is equivalent to the percent identity between the two sequences. The percent identity between the two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent identity between two amino acid sequences can be determined using the algorithm of E. Meyers and W. Miller (*Comput. Appl. Biosci.*, 4:11-17 (1988)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (*J. Mol. Biol.* 48:444-453 (1970)) algorithm which has been incorporated into the GAP program in the GCG software package (available at http://www.gcg.com), using either a Blossum 62 matrix or a PAM250 matrix, and a gap weight of 16, 14, 12, 10, 8, 6, or 4 and a length weight of 1, 2, 3, 4, 5, or 6.

Additionally or alternatively, the protein sequences of the present disclosure can further be used as a "query sequence" to perform a search against public databases to, for example, to identify related sequences. Such searches can be performed using the XBLAST program (version 2.0) of Altschul, et al. (1990) *J. Mol. Biol.* 215:403-10. BLAST protein searches can be performed with the) XBLAST program, score=50, wordlength=3 to obtain amino acid sequences homologous to the antibody molecules of this disclosure. To obtain gapped alignments for comparison purposes, Gapped BLAST can be utilized as described in Altschul et al., (1997) *Nucleic Acids Res.* 25(17):3389-3402. When utilizing BLAST and Gapped BLAST programs, the default parameters of the respective programs (e.g., XBLAST and NBLAST) are useful. See www.ncbi.nlm.nih.gov.

Antibodies with Conservative Modifications

In certain embodiments, an antibody of this disclosure comprises a heavy chain variable region comprising CDR1, CDR2 and CDR3 sequences and a light chain variable region comprising CDR1, CDR2 and CDR3 sequences, wherein one or more of these CDR sequences comprise specified amino acid sequences based on the preferred antibodies described herein (e.g., 1H5, 3A4, 6C10), or conservative modifications thereof, and wherein the antibodies retain the desired functional properties of the anti-CTLA-4 antibodies of this disclosure. It is understood in the art that certain conservative sequence modification can be made which do not remove antigen binding. See, for example, Brummell et al. (1993) *Biochem* 32:1180-8 (describing mutational analysis in the CDR3 heavy chain domain of antibodies specific for *Salmonella*); de Wildt et al. (1997) *Prot. Eng.* 10:835-41 (describing mutation studies in anti-UA1 antibodies); Komissarov et al. (1997) *J. Biol. Chem.* 272:26864-26870 (showing that mutations in the middle of HCDR3 led to either abolished or diminished affinity); Hall et al. (1992) *J. Immunol.* 149:1605-12 (describing that a single amino acid change in the CDR3 region abolished binding activity); Kelley and O'Connell (1993) *Biochem.* 32:6862-35 (describing the contribution of Tyr residues in antigen binding); Adib-Conquy et al. (1998) *Int. Immunol.* 10:341-6 (describing the effect of hydrophobicity in binding) and Beers et al. (2000) *Clin. Can. Res.* 6:2835-43 (describing HCDR3 amino acid mutants). Accordingly, this disclosure provides an isolated monoclonal antibody, or antigen binding portion thereof, comprising a heavy chain variable region comprising CDR1, CDR2, and CDR3 sequences and a light chain variable region comprising CDR1, CDR2, and CDR3 sequences, wherein:

(a) the heavy chain variable region CDR3 sequence comprises an amino acid sequence selected from the group consisting of amino acid sequences of SEQ ID NOs: 7-9, and conservative modifications thereof;

(b) the light chain variable region CDR3 sequence comprises an amino acid sequence selected from the group consisting of amino acid sequence of SEQ ID NOs: 22-27, and conservative modifications thereof; and (c) the antibody specifically binds to human CTLA-4.

Additionally or alternatively, the antibody may possess one or more of the functional properties of the antibodies described in detail herein; for example the antibody may possess the following properties:

(a) binding to cell surface-expressed human CTLA-4;

(b) not substantially inhibiting binding of a soluble human CTLA-4 protein to cells expressing a B7-1 ligand in an in vitro assay; and (c) increasing T cell responses to antigenic stimulation in vivo.

In a preferred embodiment, the heavy chain variable region CDR2 sequence comprises an amino acid sequence selected from the group consisting of amino acid sequences of SEQ ID NOs: 4-6, and conservative modifications thereof; and the light chain variable region CDR2 sequence comprises an amino acid sequence selected from the group consisting of amino acid sequences of SEQ ID NOs: 16-21, and conservative modifications thereof. In another preferred embodiment, the heavy chain variable region CDR1 sequence comprises an amino acid sequence selected from the group consisting of amino acid sequences of SEQ ID NOs: 1-3, and conservative modifications thereof; and the light chain variable region CDR1 sequence comprises an amino acid sequence selected from the group consisting of amino acid sequences of SEQ ID NOs: 10-15, and conservative modifications thereof.

In various embodiments, the antibody can be, for example, human antibodies, humanized antibodies or chimeric antibodies.

As used herein, the term "conservative sequence modifications" is intended to refer to amino acid modifications that do not significantly affect or alter the binding characteristics of the antibody containing the amino acid sequence. Such conservative modifications include amino acid substitutions, additions and deletions. Modifications can be introduced into an antibody of this disclosure by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the CDR regions of an antibody of this disclosure can be replaced with other amino acid residues from the same side chain family and the altered antibody can be tested for retained function (i.e., the functions set forth above) using the functional assays described herein.

Antibodies that Bind to the Same Epitope as Anti-CTLA-4 Antibodies

In another embodiment, this disclosure provides antibodies that bind to the same epitope on human CTLA-4 as any of the anti-CTLA-4 monoclonal antibodies of this disclosure (i.e., antibodies that have the ability to cross-compete for binding to CTLA-4 with any of the monoclonal antibodies of this disclosure). In preferred embodiments, the reference antibody for cross-competition studies can be the monoclonal antibody 1H5 (having $V_H$ and $V_K$ sequences as shown in SEQ ID NOs: 28 and 31, 32, 33, or 34, respectively), or the monoclonal antibody 3A4 (having $V_H$ and $V_K$ sequences as shown in SEQ ID NOs: 29 and 35, respectively) or the monoclonal antibody 6C10 (having $V_H$ and $V_K$ sequences as shown in SEQ ID NOs: 30 and 36, respectively).

Such cross-competing antibodies can be identified based on their ability to cross-compete with 1H5, 3A4 or 6C10 in standard CTLA-4 binding assays. For example, standard ELISA assays can be used in which recombinant CTLA-4 is immobilized on the plate, one of the antibodies is fluorescently labeled and the ability of non-labeled antibodies to compete off the binding of the labeled antibody is evaluated. Additionally or alternatively, BIAcore analysis can be used to assess the ability of the antibodies to cross-compete. The ability of a test antibody to inhibit the binding of, for example, 1H5, 3A4 or 6C10, to human CTLA-4 demonstrates that the test antibody can compete with 1H5, 3A4 or 6C10 for binding to human CTLA-4 and thus binds to the same epitope on human CTLA-4 as 1H5, 3A4 or 6C10. In a preferred embodiment, the antibody that binds to the same epitope on CTLA-4 as 1H5, 3A4 or 6C10 is a human monoclonal antibody. Such human monoclonal antibodies can be prepared and isolated as described in the Examples.

Engineered and Modified Antibodies

An antibody of this disclosure further can be prepared using an antibody having one or more of the $V_H$ and/or $V_K$ sequences disclosed herein as starting material to engineer a modified antibody, which modified antibody may have altered properties from the starting antibody. An antibody can be engineered by modifying one or more residues within one or both variable regions (i.e., $V_H$ and/or $V_K$), for example within one or more CDR regions and/or within one or more framework regions. Additionally or alternatively, an antibody can be engineered by modifying residues within the constant region(s), for example to alter the effector function(s) of the antibody.

In certain embodiments, CDR grafting can be used to engineer variable regions of antibodies. Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann, L. et al. (1998) *Nature* 332:323-327; Jones, P. et al. (1986) *Nature* 321:522-525; Queen, C. et al. (1989) *Proc. Natl. Acad. See. U.S.A.* 86:10029-10033; U.S. Pat. No. 5,225,539 to Winter, and U.S. Pat. Nos. 5,530,101; 5,585,089; 5,693,762 and 6,180,370 to Queen et al.)

Accordingly, another embodiment of this disclosure pertains to an isolated monoclonal antibody, or antigen binding portion thereof, comprising a heavy chain variable region comprising CDR1, CDR2, and CDR3 sequences comprising an amino acid sequence selected from the group consisting of SEQ ID NOs: 1-3, SEQ ID NOs: 4-6, and SEQ ID NOs: 7-9, respectively, and a light chain variable region comprising CDR1, CDR2, and CDR3 sequences comprising an amino acid sequence selected from the group consisting of SEQ ID NOs: 10-15, SEQ ID NOs: 16-21, and SEQ ID NOs: 22-27, respectively. Thus, such antibodies contain the $V_H$ and $V_K$ CDR sequences of monoclonal antibodies 1H5, 3A4 or 6C10 yet may contain different framework sequences from these antibodies.

Such framework sequences can be obtained from public DNA databases or published references that include germline antibody gene sequences. For example, germline DNA sequences for human heavy and light chain variable region genes can be found in the "VBase" human germline sequence database (available on the Internet at www.mrc-cpe.cam.ac.uk/vbase), as well as in Kabat, E. A., et al. (1991) Sequences of Proteins of Immunological Interest, Fifth Edition, U.S. Department of Health and Human Services, NIH Publication No. 91-3242; Tomlinson, I. M., et al. (1992) "The Repertoire of Human Germline $V_H$ Sequences Reveals about Fifty Groups of $V_H$ Segments with Different Hypervariable Loops" *J. Mol. Biol.* 227:776-798; and Cox, J. P. L. et al. (1994) "A Directory of Human Germ-line $V_H$ Segments Reveals a Strong Bias in their Usage" *Eur. J. Immunol.* 24:827-836; the contents of each of which are expressly incorporated herein by reference. As another example, the germline DNA sequences for human heavy and light chain variable region genes can be found in the Genbank database. For example, the following heavy chain germline sequences found in the HCo7 HuMAb mouse are available in the accompanying Genbank accession numbers: 1-69 (NG_0010109, NT_024637 and BC070333), 3-33 (NG_0010109 and NT_024637) and 3-7 (NG_0010109 and NT_024637). As another example, the following heavy chain germline sequences found in the HCo12 HuMAb mouse are available in the accompanying Genbank accession numbers: 1-69 (NG_0010109, NT_024637 and BC070333), 5-51 (NG_0010109 and NT_024637), 4-34 (NG_0010109 and NT_024637), 3-30.3 (CAJ556644) and 3-23 (AJ406678).

Antibody protein sequences are compared against a compiled protein sequence database using one of the sequence similarity searching methods called the Gapped BLAST (Altschul et al. (1997) *Nucleic Acids Research* 25:3389-3402), which is well known to those skilled in the art. BLAST is a heuristic algorithm in that a statistically significant alignment between the antibody sequence and the database sequence is likely to contain high-scoring segment pairs (HSP) of aligned words. Segment pairs whose scores cannot be improved by extension or trimming is called a hit. Briefly, the nucleotide sequences of VBASE origin (http://vbase.mrc-cpe.cam.ac.uk/vbase1/list2.php) are translated and the region between and including FR1 through FR3 framework region is retained. The database sequences have an average length of 98 residues. Duplicate sequences which are exact matches over the entire length of the protein are removed. A BLAST search for proteins using the program blastp with default, standard parameters except the low complexity filter, which is turned off, and the substitution matrix of BLOSUM62, filters for top 5 hits yielding sequence matches. The nucleotide sequences are translated in all six frames and the frame with no stop codons in the matching segment of the database sequence is considered the potential hit. This is in turn confirmed using the BLAST program tblastx, which translates the antibody sequence in all six frames and compares those translations to the VBASE nucleotide sequences dynamically translated in all six frames.

The identities are exact amino acid matches between the antibody sequence and the protein database over the entire length of the sequence. The positives (identities+substitution match) are not identical but amino acid substitutions guided by the BLOSUM62 substitution matrix. If the antibody sequence matches two of the database sequences with same identity, the hit with most positives would be decided to be the matching sequence hit.

Preferred framework sequences for use in the antibodies of this disclosure are those that are structurally similar to the framework sequences used by selected antibodies of this disclosure, e.g., similar to the $V_H$ 4-39 (SEQ ID NO: 46) or $V_H$ 3-33 (SEQ ID NO: 47) heavy chain framework sequences and/or the $V_K$ L18 (SEQ ID NO: 48) or $V_K$ L15 (SEQ ID NO: 49) light chain framework sequences used by preferred monoclonal antibodies of this disclosure. The $V_H$ CDR1, CDR2, and CDR3 sequences, and the $V_K$ CDR1, CDR2, and CDR3 sequences, can be grafted onto framework regions that have the identical sequence as that found in the germline immunoglobulin gene from which the framework sequence derive, or the CDR sequences can be grafted onto framework regions that contain one or more mutations as compared to the germline sequences. For example, it has been found that in certain instances it is beneficial to mutate residues within the framework regions to maintain or enhance the antigen binding ability of the antibody (see e.g., U.S. Pat. Nos. 5,530,101; 5,585,089; 5,693,762 and 6,180,370 to Queen et al.).

Another type of variable region modification is to mutate amino acid residues within the $V_H$ and/or $V_K$ CDR1, CDR2 and/or CDR3 regions to thereby improve one or more binding properties (e.g., affinity) of the antibody of interest. Site-directed mutagenesis or PCR-mediated mutagenesis can be performed to introduce the mutation(s) and the effect on antibody binding, or other functional property of interest, can be evaluated in in vitro or in vivo assays as described herein and provided in the Examples. Preferably conservative modifications (as discussed above) are introduced. The mutations may be amino acid substitutions, additions or deletions, but are preferably substitutions. Moreover, typically no more than one, two, three, four or five residues within a CDR region are altered.

Accordingly, in another embodiment, the instant disclosure provides isolated anti-CTLA-4 monoclonal antibodies, or antigen binding portions thereof, comprising a heavy chain variable region comprising: (a) a $V_H$ CDR1 region comprising an amino acid sequence selected from the group consisting of SEQ ID NOs: 1-3, or an amino acid sequence having one, two, three, four or five amino acid substitutions, deletions or additions as compared to SEQ ID NOs: 1-3; (b) a $V_H$ CDR2 region comprising an amino acid sequence selected from the group consisting of SEQ ID NOs: 4-6, or an amino acid sequence having one, two, three, four or five amino acid substitutions, deletions or additions as compared to SEQ ID NOs: 4-6; (c) a $V_H$ CDR3 region comprising an amino acid sequence selected from the group consisting of SEQ ID NOs: 7-9, or an amino acid sequence having one, two, three, four or five amino acid substitutions, deletions or additions as compared to SEQ ID NOs: 7-9; (d) a $V_K$ CDR1 region comprising an amino acid sequence selected from the group consisting of SEQ ID NOs: 10-15, or an amino acid sequence having one, two, three, four or five amino acid substitutions, deletions or additions as compared to SEQ ID NOs: 10-15; (e) a $V_K$ CDR2 region comprising an amino acid sequence selected from the group consisting of SEQ ID NOs: 16-21, or an amino acid sequence having one, two, three, four or five amino acid substitutions, deletions or additions as compared to SEQ ID NOs: 16-21; and (f) a $V_K$ CDR3 region comprising an amino acid sequence selected from the group consisting of SEQ ID NOs: 22-27, or an amino acid sequence having one, two, three, four or five amino acid substitutions, deletions or additions as compared to SEQ ID NOs: 22-27.

Engineered antibodies of this disclosure include those in which modifications have been made to framework residues within $V_H$ and/or $V_K$, e.g. to improve the properties of the antibody. Typically such framework modifications are made to decrease the immunogenicity of the antibody. For example, one approach is to "backmutate" one or more framework residues to the corresponding germline sequence. More specifically, an antibody that has undergone somatic mutation may contain framework residues that differ from the germline sequence from which the antibody is derived. Such residues can be identified by comparing the antibody framework sequences to the germline sequences from which the antibody is derived.

For example, for the 1H5 $V_H$ region, framework region amino acid positions 46, 71, 77, 83, 85, 88 and 96 (using the Kabat numbering system) differs from germline. One or more of these positions can be backmutated to the germline sequence by making one or more of the following substitutions: E46G, V71I, R77K, N83K, N85S, I88T and/or S96Y.

Furthermore, for the 3A4 $V_H$ region, framework region amino acid position 4 (using the Kabat numbering system) differs from germline. This position can be backmutated to the germline sequence by making the following substitution: V4L.

Furthermore, for the 6C10 $V_H$ region, framework region amino acid position 23 (using the Kabat numbering system) differs from germline. This position can be backmutated to the germline sequence by making the following substitution: T23A.

Another type of framework modification involves mutating one or more residues within the framework region, or even within one or more CDR regions, to remove T cell epitopes to thereby reduce the potential immunogenicity of the antibody. This approach is also referred to as "deimmunization" and is described in further detail in U.S. Patent Publication No. 20030153043 by Carr et al.

In addition or alternative to modifications made within the framework or CDR regions, antibodies of this disclosure may be engineered to include modifications within the Fc region, typically to alter one or more functional properties of the antibody, such as serum half-life, complement fixation, Fc receptor binding, and/or antigen-dependent cellular cytotoxicity. Furthermore, an antibody of this disclosure may be chemically modified (e.g., one or more chemical moieties can be attached to the antibody) or be modified to alter its glycosylation, again to alter one or more functional properties of the antibody. Each of these embodiments is described in further detail below. The numbering of residues in the Fc region is that of the EU index of Kabat.

In one embodiment, the hinge region of CH1 is modified such that the number of cysteine residues in the hinge region is altered, e.g., increased or decreased. This approach is described further in U.S. Pat. No. 5,677,425 by Bodmer et al. The number of cysteine residues in the hinge region of CH1 is altered to, for example, facilitate assembly of the light and heavy chains or to increase or decrease the stability of the antibody.

In another embodiment, the Fc hinge region of an antibody is mutated to decrease the biological half life of the antibody. More specifically, one or more amino acid mutations are introduced into the CH2-CH3 domain interface region of the Fc-hinge fragment such that the antibody has impaired Staphylococcal protein A (SpA) binding relative to native Fc-hinge domain SpA binding. This approach is described in further detail in U.S. Pat. No. 6,165,745 by Ward et al.

In another embodiment, the antibody is modified to increase its biological half life. Various approaches are possible. For example, one or more of the following mutations can be introduced: T252L, T254S, T256F, as described in U.S. Pat. No. 6,277,375 to Ward. Alternatively, to increase the biological half life, the antibody can be altered within the CH1 or CL region to contain a salvage receptor binding epitope taken from two loops of a CH2 domain of an Fc region of an IgG, as described in U.S. Pat. Nos. 5,869,046 and 6,121,022 by Presta et al.

In yet other embodiments, the Fc region is altered by replacing at least one amino acid residue with a different amino acid residue to alter the effector function(s) of the antibody. For example, one or more amino acids selected from amino acid residues 234, 235, 236, 237, 297, 318, 320 and 322 can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in further detail in U.S. Pat. Nos. 5,624,821 and 5,648,260, both by Winter et al.

In another example, one or more amino acids selected from amino acid residues 329, 331 and 322 can be replaced with a different amino acid residue such that the antibody has altered C1q binding and/or reduced or abolished complement dependent cytotoxicity (CDC). This approach is described in further detail in U.S. Pat. No. 6,194,551 by Idusogie et al.

In another example, one or more amino acid residues within amino acid positions 231 and 239 are altered to thereby alter the ability of the antibody to fix complement. This approach is described further in PCT Publication WO 94/29351 by Bodmer et al.

In yet another example, the Fc region is modified to increase the ability of the antibody to mediate antibody dependent cellular cytotoxicity (ADCC) and/or to increase the affinity of the antibody for an Fcγ receptor by modifying one or more amino acids at the following positions: 238, 239, 248, 249, 252, 254, 255, 256, 258, 265, 267, 268, 269, 270, 272, 276, 278, 280, 283, 285, 286, 289, 290, 292, 293, 294, 295, 296, 298, 301, 303, 305, 307, 309, 312, 315, 320, 322, 324, 326, 327, 329, 330, 331, 333, 334, 335, 337, 338, 340, 360, 373, 376, 378, 382, 388, 389, 398, 414, 416, 419, 430, 434, 435, 437, 438 or 439. This approach is described further in PCT Publication WO 00/42072 by Presta. Moreover, the binding sites on human IgG1 for FcγR1, FcγRII, FcγRIII and FcRn have been mapped and variants with improved binding have been described (see Shields, R. L. et al. (2001) *J. Biol. Chem.* 276:6591-6604). Specific mutations at positions 256, 290, 298, 333, 334 and 339 were shown to improve binding to FcγRIII. Additionally, the following combination mutants were shown to improve FcγRIII binding: T256A/S298A, S298A/E333A, S298A/K224A and S298A/E333A/K334A.

In still another embodiment, the glycosylation of an antibody is modified. For example, an aglycoslated antibody can be made (i.e., the antibody lacks glycosylation). Glycosylation can be altered to, for example, increase the affinity of the antibody for antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Such an approach is described in further detail in U.S. Pat. Nos. 5,714,350 and 6,350,861 by Co et al.

Additionally or alternatively, an antibody can be made that has an altered type of glycosylation, such as a hypofucosylated antibody having reduced amounts of fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of this disclosure to thereby produce an antibody with altered glycosylation. For example, the cell lines Ms704, Ms705, and Ms709 lack the fucosyltransferase gene, FUT8 (alpha (1,6) fucosyltransferase), such that antibodies expressed in the Ms704, Ms705, and Ms709 cell lines lack fucose on their carbohydrates. The Ms704, Ms705, and Ms709 FUT8$^{-/-}$ cell lines were created by the targeted disruption of the FUT8 gene in CHO/DG44 cells using two replacement vectors (see U.S. Patent Publication No. 20040110704 by Yamane et al. and Yamane-Ohnuki et al. (2004) *Biotechnol Bioeng* 87:614-22). As another example, EP 1,176,195 by Hanai et al. describes a cell line with a functionally disrupted FUT8 gene, which encodes a fucosyl transferase, such that antibodies expressed in such a cell line exhibit hypofucosylation by reducing or eliminating the alpha 1,6 bond-related enzyme. Hanai et al. also describe cell lines which have a low enzyme activity for adding fucose to the N-acetylglucosamine that binds to the Fc region of the antibody or does not have the enzyme activity, for example the rat myeloma cell line YB2/0 (ATCC CRL 1662). PCT Publication WO 03/035835 by Presta describes a variant CHO cell line, Lec13 cells, with reduced ability to attach fucose to Asn(297)-linked carbohydrates, also resulting in hypofucosylation of antibodies expressed in that host cell (see also Shields, R. L. et al. (2002) *J. Biol. Chem.* 277:26733-26740). Antibodies with a modified glycosylation profile can also be produced in chicken eggs, as described in US Patent Application No. PCT/US06/05853. Alternatively, antibodies with a modified glycosylation profile can be produced in plant cells, such as *Lemna*. Methods for production of antibodies in a plant system are disclosed in the U.S. patent application Ser. No. 60/836,998 corresponding to Alston & Bird LLP filed on Aug. 11, 2006. PCT Publication WO 99/54342 by Umana et al. describes cell lines engineered to express glycoprotein-modifying glycosyl transferases (e.g., beta(1,4)-N-acetylglucosaminyltransferase III (GnTIII)) such that antibodies expressed in the engineered cell lines exhibit increased bisecting GlcNac structures which results in increased ADCC activity of the antibodies (see also Umana et al. (1999) *Nat. Biotech.* 17:176-180). Alternatively, the fucose residues of the antibody may be cleaved off using a fucosidase enzyme. For example, the fucosidase alpha-L-fucosidase removes fucosyl residues from antibodies (Tarentino, A. L. et al. (1975) *Biochem.* 14:5516-23).

Another modification of the antibodies herein that is contemplated by this disclosure is pegylation. An antibody can be pegylated to, for example, increase the biological (e.g., serum) half life of the antibody. To pegylate an antibody, the antibody, or fragment thereof, typically is reacted with polyethylene glycol (PEG), such as a reactive ester or aldehyde derivative of PEG, under conditions in which one or more PEG groups become attached to the antibody or antibody fragment. Preferably, the pegylation is carried out via an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono (C1-C10) alkoxy- or aryloxy-polyethylene glycol or polyethylene glycol-maleimide. In certain embodiments, the antibody to be pegylated is an aglycosylated antibody. Methods for pegylating proteins are known in the art and can be applied to the antibodies of this disclosure. See for example, EP 0 154 316 by Nishimura et al. and EP 0 401 384 by Ishikawa et al.

Antibody Fragments and Antibody Mimetics

The instant invention is not limited to traditional antibodies and may be practiced through the use of antibody fragments and antibody mimetics. As detailed below, a wide variety of antibody fragment and antibody mimetic technologies have now been developed and are widely known in the art. While a number of these technologies, such as domain antibodies, Nanobodies, and UniBodies make use of fragments of, or other modifications to, traditional antibody structures, there are also alternative technologies, such as Affibodies, DARPins, Anticalins, Avimers, and Versabodies that employ binding structures that, while they mimic traditional antibody binding, are generated from and function via distinct mechanisms.

Domain Antibodies (dAbs) are the smallest functional binding units of antibodies, corresponding to the variable regions of either the heavy (VH) or light (VK) chains of human antibodies. Domain Antibodies have a molecular weight of approximately 13 kDa. Domantis has developed a series of large and highly functional libraries of fully human VH and VK dAbs (more than ten billion different sequences in each library), and uses these libraries to select dAbs that are specific to therapeutic targets. In contrast to many conventional antibodies, Domain Antibodies are well expressed in bacterial, yeast, and mammalian cell systems. Further details of domain antibodies and methods of production thereof may be obtained by reference to U.S. Pat. Nos. 6,291,158; 6,582,915; 6,593,081; 6,172,197; 6,696,245; US Serial No. 2004/0110941; European patent application No. 1433846 and European Patents 0368684 & 0616640; WO05/035572, WO04/101790, WO04/081026, WO04/058821, WO04/003019 and WO03/002609, each of which is herein incorporated by reference in its entirety.

Nanobodies are antibody-derived therapeutic proteins that contain the unique structural and functional properties of naturally-occurring heavy-chain antibodies. These heavy-chain antibodies contain a single variable domain (VHH) and two constant domains (CH2 and CH3). Importantly, the cloned and isolated VHH domain is a perfectly stable polypeptide harbouring the full antigen-binding capacity of the original heavy-chain antibody. Nanobodies have a high homology with the VH domains of human antibodies and can be further humanized without any loss of activity. Importantly, Nanobodies have a low immunogenic potential, which has been confirmed in primate studies with Nanobody lead compounds.

Nanobodies combine the advantages of conventional antibodies with important features of small molecule drugs. Like conventional antibodies, Nanobodies show high target specificity, high affinity for their target and low inherent toxicity. However, like small molecule drugs they can inhibit enzymes and readily access receptor clefts. Furthermore, Nanobodies are extremely stable, can be administered by means other than injection (see e.g. WO 04/041867, which is herein incorporated by reference in its entirety) and are easy to manufacture. Other advantages of Nanobodies include recognizing uncommon or hidden epitopes as a result of their small size, binding into cavities or active sites of protein targets with high affinity and selectivity due to their unique 3-dimensional, drug format flexibility, tailoring of half-life and ease and speed of drug discovery.

Nanobodies are encoded by single genes and are efficiently produced in almost all prokaryotic and eukaryotic hosts e.g. *E. coli* (see e.g. U.S. Pat. No. 6,765,087, which is herein incorporated by reference in its entirety), molds (for example *Aspergillus* or *Trichoderma*) and yeast (for example *Saccharomyces, Kluyveromyces, Hansenula* or *Pichia*) (see e.g. U.S. Pat. No. 6,838,254, which is herein incorporated by reference in its entirety). The production process is scalable and multi-kilogram quantities of Nanobodies have been produced. Because Nanobodies exhibit a superior stability compared with conventional antibodies, they can be formulated as a long shelf-life, ready-to-use solution.

The Nanoclone method (see e.g. WO 06/079372, which is herein incorporated by reference in its entirety) is a proprietary method for generating Nanobodies against a desired target, based on automated high-throughout selection of B-cells and could be used in the context of the instant invention.

UniBodies are another antibody fragment technology, however this one is based upon the removal of the hinge region of IgG4 antibodies. The deletion of the hinge region results in a molecule that is essentially half the size of traditional IgG4 antibodies and has a univalent binding region rather than the bivalent binding region of IgG4 antibodies. It is also well known that IgG4 antibodies are inert and thus do not interact with the immune system, which may be advantageous for the treatment of diseases where an immune response is not desired, and this advantage is passed onto UniBodies. For example, UniBodies may function to inhibit or silence, but not kill, the cells to which they are bound. Additionally, UniBody binding to cancer cells do not stimulate them to proliferate. Furthermore, because UniBodies are about half the size of traditional IgG4 antibodies, they may show better distribution over larger solid tumors with potentially advantageous efficacy. UniBodies are cleared from the body at a similar rate to whole IgG4 antibodies and are able to bind with a similar affinity for their antigens as whole antibodies. Further details of UniBodies may be obtained by reference to patent WO2007/059782, which is herein incorporated by reference in its entirety.

Affibody molecules represent a new class of affinity proteins based on a 58-amino acid residue protein domain, derived from one of the IgG-binding domains of staphylococcal protein A. This three helix bundle domain has been used as a scaffold for the construction of combinatorial phagemid libraries, from which Affibody variants that target the desired molecules can be selected using phage display technology (Nord K, Gunneriusson E, Ringdahl J, Stahl S, Uhlen M, Nygren P A, Binding proteins selected from combinatorial libraries of an α-helical bacterial receptor domain, Nat Biotechnol 1997; 15:772-7. Ronmark J, Gronlund H, Uhlen M, Nygren P A, Human immunoglobulin A (IgA)-specific ligands from combinatorial engineering of protein A, Eur J Biochem 2002; 269:2647-55.). The simple, robust structure of Affibody molecules in combination with their low molecular weight (6 kDa), make them suitable for a wide variety of applications, for instance, as detection reagents (Ronmark J, Hansson M, Nguyen T, et al, Construction and characterization of affibody-Fc chimeras produced in *Escherichia coli*, J Immunol Methods 2002; 261:199-211) and to inhibit receptor interactions (Sandstorm K, Xu Z, Forsberg G, Nygren P A, Inhibition of the CD28-CD80 co-stimulation signal by a CD28-binding Affibody ligand developed by combinatorial protein engineering, Protein Eng 2003; 16:691-7). Further details of Affibodies and methods of production thereof may be obtained by reference to U.S. Pat. No. 5,831,012 which is herein incorporated by reference in its entirety.

Labelled Affibodies may also be useful in imaging applications for determining abundance of Isoforms.

DARPins (Designed Ankyrin Repeat Proteins) are one example of an antibody mimetic DRP (Designed Repeat Protein) technology that has been developed to exploit the binding abilities of non-antibody polypeptides. Repeat proteins such as ankyrin or leucine-rich repeat proteins, are ubiquitous binding molecules, which occur, unlike antibodies, intra- and extracellularly. Their unique modular architecture features repeating structural units (repeats), which stack together to form elongated repeat domains displaying variable and modular target-binding surfaces. Based on this modularity, combinatorial libraries of polypeptides with highly diversified binding specificities can be generated. This strategy includes the consensus design of self-compatible repeats displaying variable surface residues and their random assembly into repeat domains.

DARPins can be produced in bacterial expression systems at very high yields and they belong to the most stable proteins known. Highly specific, high-affinity DARPins to a broad range of target proteins, including human receptors, cytokines, kinases, human proteases, viruses and membrane proteins, have been selected. DARPins having affinities in the single-digit nanomolar to picomolar range can be obtained.

DARPins have been used in a wide range of applications, including ELISA, sandwich ELISA, flow cytometric analysis (FACS), immunohistochemistry (IHC), chip applications, affinity purification or Western blotting. DARPins also proved to be highly active in the intracellular compartment for example as intracellular marker proteins fused to green fluorescent protein (GFP). DARPins were further used to inhibit viral entry with IC50 in the pM range. DARPins are not only ideal to block protein-protein interactions, but also to inhibit enzymes. Proteases, kinases and transporters have been successfully inhibited, most often an allosteric inhibition mode. Very fast and specific enrichments on the tumor and very favorable tumor to blood ratios make DARPins well suited for in vivo diagnostics or therapeutic approaches.

Additional information regarding DARPins and other DRP technologies can be found in US Patent Application Publication No. 2004/0132028 and International Patent Application Publication No. WO 02/20565, both of which are hereby incorporated by reference in their entirety.

Anticalins are an additional antibody mimetic technology, however in this case the binding specificity is derived from lipocalins, a family of low molecular weight proteins that are naturally and abundantly expressed in human tissues and body fluids. Lipocalins have evolved to perform a range of functions in vivo associated with the physiological transport and storage of chemically sensitive or insoluble compounds. Lipocalins have a robust intrinsic structure comprising a highly conserved β-barrel which supports four loops at one terminus of the protein. These loops form the entrance to a binding pocket and conformational differences in this part of the molecule account for the variation in binding specificity between individual lipocalins.

While the overall structure of hypervariable loops supported by a conserved β-sheet framework is reminiscent of immunoglobulins, lipocalins differ considerably from antibodies in terms of size, being composed of a single polypeptide chain of 160-180 amino acids which is marginally larger than a single immunoglobulin domain.

Lipocalins are cloned and their loops are subjected to engineering in order to create Anticalins. Libraries of structurally diverse Anticalins have been generated and Anticalin display allows the selection and screening of binding function, followed by the expression and production of soluble protein for further analysis in prokaryotic or eukaryotic systems. Studies have successfully demonstrated that Anticalins can be developed that are specific for virtually any human target protein can be isolated and binding affinities in the nanomolar or higher range can be obtained.

Anticalins can also be formatted as dual targeting proteins, so-called Duocalins. A Duocalin binds two separate therapeutic targets in one easily produced monomeric protein using standard manufacturing processes while retaining target specificity and affinity regardless of the structural orientation of its two binding domains Modulation of multiple targets through a single molecule is particularly advantageous in diseases known to involve more than a single causative factor. Moreover, bi- or multivalent binding formats such as Duocalins have significant potential in targeting cell surface molecules in disease, mediating agonistic effects on signal transduction pathways or inducing enhanced internalization effects via binding and clustering of cell surface receptors. Furthermore, the high intrinsic stability of Duocalins is comparable to monomeric Anticalins, offering flexible formulation and delivery potential for Duocalins.

Additional information regarding Anticalins can be found in U.S. Pat. No. 7,250,297 and International Patent Application Publication No. WO 99/16873, both of which are hereby incorporated by reference in their entirety.

Another antibody mimetic technology useful in the context of the instant invention are Avimers. Avimers are evolved from a large family of human extracellular receptor domains by in vitro exon shuffling and phage display, generating multidomain proteins with binding and inhibitory properties. Linking multiple independent binding domains has been shown to create avidity and results in improved affinity and specificity compared with conventional single-epitope binding proteins. Other potential advantages include simple and efficient production of multitarget-specific molecules in *Escherichia coli*, improved thermostability and resistance to proteases. Avimers with sub-nanomolar affinities have been obtained against a variety of targets.

Additional information regarding Avimers can be found in US Patent Application Publication Nos. 2006/0286603, 2006/0234299, 2006/0223114, 2006/0177831, 2006/0008844, 2005/0221384, 2005/0164301, 2005/0089932, 2005/0053973, 2005/0048512, 2004/0175756, all of which are hereby incorporated by reference in their entirety.

Versabodies are another antibody mimetic technology that could be used in the context of the instant invention. Versabodies are small proteins of 3-5 kDa with >15% cysteines, which form a high disulfide density scaffold, replacing the hydrophobic core that typical proteins have. The replacement of a large number of hydrophobic amino acids, comprising the hydrophobic core, with a small number of disulfides results in a protein that is smaller, more hydrophilic (less aggregation and non-specific binding), more resistant to proteases and heat, and has a lower density of T-cell epitopes, because the residues that contribute most to MHC presentation are hydrophobic. All four of these properties are well-known to affect immunogenicity, and together they are expected to cause a large decrease in immunogenicity.

The inspiration for Versabodies comes from the natural injectable biopharmaceuticals produced by leeches, snakes, spiders, scorpions, snails, and anemones, which are known to exhibit unexpectedly low immunogenicity. Starting with selected natural protein families, by design and by screening the size, hydrophobicity, proteolytic antigen processing, and epitope density are minimized to levels far below the average for natural injectable proteins.

Given the structure of Versabodies, these antibody mimetics offer a versatile format that includes multi-valency, multi-specificity, a diversity of half-life mechanisms, tissue targeting modules and the absence of the antibody Fc region. Furthermore, Versabodies are manufactured in E. coli at high yields, and because of their hydrophilicity and small size, Versabodies are highly soluble and can be formulated to high concentrations. Versabodies are exceptionally heat stable (they can be boiled) and offer extended shelf-life.

Additional information regarding Versabodies can be found in US Patent Application Publication No. 2007/0191272 which is hereby incorporated by reference in its entirety.

The detailed description of antibody fragment and antibody mimetic technologies provided above is not intended to be a comprehensive list of all technologies that could be used in the context of the instant specification. For example, and also not by way of limitation, a variety of additional technologies including alternative polypeptide-based technologies, such as fusions of complimentary determining regions as outlined in Qui et al., Nature Biotechnology, 25(8) 921-929 (2007), which is hereby incorporated by reference in its entirety, as well as nucleic acid-based technologies, such as the RNA aptamer technologies described in U.S. Pat. Nos. 5,789,157, 5,864,026, 5,712,375, 5,763,566, 6,013,443, 6,376,474, 6,613,526, 6,114,120, 6,261,774, and 6,387,620, all of which are hereby incorporated by reference, could be used in the context of the instant invention.

Antibody Physical Properties

The antibodies of the present disclosure may be further characterized by the various physical properties of the anti-CTLA-4 antibodies. Various assays may be used to detect and/or differentiate different classes of antibodies based on these physical properties.

In some embodiments, antibodies of the present disclosure may contain one or more glycosylation sites in either the light or heavy chain variable region. The presence of one or more glycosylation sites in the variable region may result in increased immunogenicity of the antibody or an alteration of the pK of the antibody due to altered antigen binding (Marshall et al (1972) Annu Rev Biochem 41:673-702; Gala F A and Morrison S L (2004) J Immunol 172:5489-94; Wallick et al (1988) J Exp Med 168:1099-109; Spiro RG (2002) Glycobiology 12:43R-56R; Parekh et al (1985) Nature 316:452-7; Mimura et al. (2000) Mol Immunol 37:697-706). Glycosylation has been known to occur at motifs containing an N-X-S/T sequence. Variable region glycosylation may be tested using a Glycoblot assay, which cleaves the antibody to produce a Fab, and then tests for glycosylation using an assay that measures periodate oxidation and Schiff base formation. Alternatively, variable region glycosylation may be tested using Dionex light chromatography (Dionex-LC), which cleaves saccharides from a Fab into monosaccharides and analyzes the individual saccharide content. In some instances, it is preferred to have an anti-CTLA-4 antibody that does not contain variable region glycosylation. This can be achieved either by selecting antibodies that do not contain the glycosylation motif in the variable region or by mutating residues within the glycosylation motif using standard techniques well known in the art.

In a preferred embodiment, the antibodies of the present disclosure do not contain asparagine isomerism sites. A deamidation or isoaspartic acid effect may occur on N-G or D-G sequences, respectively. The deamidation or isoaspartic acid effect results in the creation of isoaspartic acid which decreases the stability of an antibody by creating a kinked structure off a side chain carboxy terminus rather than the main chain. The creation of isoaspartic acid can be measured using an iso-quant assay, which uses a reverse-phase HPLC to test for isoaspartic acid.

Each antibody will have a unique isoelectric point (pI), but generally antibodies will fall in the pH range of between 6 and 9.5. The pI for an IgG1 antibody typically falls within the pH range of 7-9.5 and the pI for an IgG4 antibody typically falls within the pH range of 6-8. Antibodies may have a pI that is outside this range. Although the effects are generally unknown, there is speculation that antibodies with a pI outside the normal range may have some unfolding and instability under in vivo conditions. The isoelectric point may be tested using a capillary isoelectric focusing assay, which creates a pH gradient and may utilize laser focusing for increased accuracy (Janini et al (2002) Electrophoresis 23:1605-11; Ma et al. (2001) Chromatographia 53:S75-89; Hunt et al (1998) J Chromatogr A 800:355-67). In some instances, it is preferred to have an anti-CTLA-4 antibody that contains a pI value that falls in the normal range. This can be achieved either by selecting antibodies with a pI in the normal range, or by mutating charged surface residues using standard techniques well known in the art.

Each antibody will have a melting temperature that is indicative of thermal stability (Krishnamurthy R and Manning MC (2002) Curr Pharm Biotechnol 3:361-71). A higher thermal stability indicates greater overall antibody stability in vivo. The melting point of an antibody may be measure using techniques such as differential scanning calorimetry (Chen et al (2003) Pharm Res 20:1952-60; Ghirlando et al (1999) Immunol Lett 68:47-52). $T_{M1}$ indicates the temperature of the initial unfolding of the antibody. $T_{M2}$ indicates the temperature of complete unfolding of the antibody. Generally, it is preferred that the $T_{M1}$ of an antibody of the present disclosure is greater than 60° C., preferably greater than 65° C., even more preferably greater than 70° C. Alternatively, the thermal stability of an antibody may be measure using circular dichroism (Murray et al. (2002) J. Chromatogr Sci 40:343-9).

In a preferred embodiment, antibodies are selected that do not rapidly degrade. Fragmentation of an anti-CTLA-4 antibody may be measured using capillary electrophoresis (CE) and MALDI-MS, as is well understood in the art (Alexander A J and Hughes D E (1995) Anal Chem 67:3626-32).

In another preferred embodiment, antibodies are selected that have minimal aggregation effects. Aggregation may lead to triggering of an unwanted immune response and/or altered or unfavorable pharmacokinetic properties. Generally, antibodies are acceptable with aggregation of 25% or less, preferably 20% or less, even more preferably 15% or less, even more preferably 10% or less and even more preferably 5% or less. Aggregation may be measured by several techniques well known in the art, including size-exclusion column (SEC) high performance liquid chromatography (HPLC), and light scattering to identify monomers, dimers, trimers or multimers.

Methods of Engineering Antibodies

As discussed above, the anti-CTLA-4 antibodies having $V_H$ and $V_K$ sequences disclosed herein can be used to create new anti-CTLA-4 antibodies by modifying the $V_H$ and/or $V_K$ sequences, or the constant region(s) attached thereto. Thus, in another aspect of this disclosure, the structural features of an anti-CTLA-4 antibody of this disclosure, e.g. 1H5, 3A4 or 6C10, are used to create structurally related anti-CTLA-4 antibodies that retain at least one functional property of the antibodies of this disclosure, such as binding to human CTLA-4. For example, one or more CDR regions of 1H5, 3A4 or 6C10, or mutations thereof, can be combined recombinantly with known framework regions and/or other CDRs to create additional, recombinantly-engineered, anti-CTLA-4 antibodies of this disclosure, as discussed above. Other types of modifications include those described in the previous section. The starting material for the engineering method is one or more of the $V_H$ and/or $V_K$ sequences provided herein, or one or more CDR regions thereof. To create the engineered antibody, it is not necessary to actually prepare (i.e., express as a protein) an antibody having one or more of the $V_H$ and/or $V_K$ sequences provided herein, or one or more CDR regions thereof. Rather, the information contained in the sequence(s) is used as the starting material to create a "second generation" sequence(s) derived from the original sequence(s) and then the "second generation" sequence(s) is prepared and expressed as a protein.

Accordingly, in another embodiment, this disclosure provides a method for preparing an anti-CTLA-4 antibody comprising:

(a) providing: (i) a heavy chain variable region antibody sequence comprising a CDR1 sequence selected from the group consisting of SEQ ID NOs: 1-3, a CDR2 sequence selected from the group consisting of SEQ ID NOs: 4-6, and/or a CDR3 sequence selected from the group consisting of SEQ ID NOs: 7-9; and/or (ii) a light chain variable region antibody sequence comprising a CDR1 sequence selected from the group consisting of SEQ ID NOs: 10-15, a CDR2 sequence selected from the group consisting of SEQ ID NOs: 16-21, and/or a CDR3 sequence selected from the group consisting of SEQ ID NOs: 22-27;

(b) altering at least one amino acid residue within the heavy chain variable region antibody sequence and/or the light chain variable region antibody sequence to create at least one altered antibody sequence; and (c) expressing the altered antibody sequence as a protein.

Standard molecular biology techniques can be used to prepare and express the altered antibody sequence.

Preferably, the antibody encoded by the altered antibody sequence(s) is one that retains one, some or all of the functional properties of the anti-CTLA-4 antibodies described herein, which functional properties include, but are not limited to:

(a) binding to cell surface-expressed human CTLA-4;

(b) not substantially inhibiting binding of a soluble human CTLA-4 protein to cells expressing a B7-1 ligand in an in vitro assay; and (c) increasing T cell responses to antigenic stimulation in vivo.

The functional properties of the altered antibodies can be assessed using standard assays available in the art and/or described herein, such as those set forth in the Examples.

In certain embodiments of the methods of engineering antibodies of this disclosure, mutations can be introduced randomly or selectively along all or part of an anti-CTLA-4 antibody coding sequence and the resulting modified anti-CTLA-4 antibodies can be screened for binding activity and/or other functional properties as described herein. Mutational methods have been described in the art. For example, PCT Publication WO 02/092780 by Short describes methods for creating and screening antibody mutations using saturation mutagenesis, synthetic ligation assembly, or a combination thereof. Alternatively, PCT Publication WO 03/074679 by Lazar et al. describes methods of using computational screening methods to optimize physiochemical properties of antibodies.

Nucleic Acid Molecules Encoding Antibodies of this Disclosure

Another aspect of this disclosure pertains to nucleic acid molecules that encode the antibodies of this disclosure. The nucleic acids may be present in whole cells, in a cell lysate, or in a partially purified or substantially pure form. A nucleic acid is "isolated" or "rendered substantially pure" when purified away from other cellular components or other contaminants, e.g., other cellular nucleic acids or proteins, by standard techniques, including alkaline/SDS treatment, CsCl banding, column chromatography, agarose gel electrophoresis and others well known in the art. See, F. Ausubel, et al., ed. (1987) Current Protocols in Molecular Biology, Greene Publishing and Wiley Interscience, New York. A nucleic acid of this disclosure can be, for example, DNA or RNA and may or may not contain intronic sequences. In a preferred embodiment, the nucleic acid is a cDNA molecule.

Nucleic acids of this disclosure can be obtained using standard molecular biology techniques. For antibodies expressed by hybridomas (e.g., hybridomas prepared from transgenic mice carrying human immunoglobulin genes as described further below), cDNAs encoding the light and heavy chains of the antibody made by the hybridoma can be obtained by standard PCR amplification or cDNA cloning techniques. For antibodies obtained from an immunoglobulin gene library (e.g., using phage display techniques), a nucleic acid encoding such antibodies can be recovered from the gene library.

Preferred nucleic acids molecules of this disclosure are those encoding the $V_H$ and $V_K$ sequences of the 1H5, 3A4 and 6C10 monoclonal antibodies. DNA sequences encoding the $V_H$ sequences of 1H5, 3A4 and 6C10 are shown in SEQ ID NOs: 37-39, respectively. DNA sequences encoding the $V_K$ sequences of 1H5, 3A4 and 6C10 are shown in SEQ ID NOs: 40-45, respectively.

Once DNA fragments encoding $V_H$ and $V_K$ segments are obtained, these DNA fragments can be further manipulated by standard recombinant DNA techniques, for example to convert the variable region genes to full-length antibody chain genes, to Fab fragment genes or to a scFv gene. In these manipulations, a $V_K$- or $V_H$-encoding DNA fragment is operatively linked to another DNA fragment encoding another protein, such as an antibody constant region or a flexible linker. The term "operatively linked", as used in this context, is intended to mean that the two DNA fragments are joined such that the amino acid sequences encoded by the two DNA fragments remain in-frame.

The isolated DNA encoding the $V_H$ region can be converted to a full-length heavy chain gene by operatively linking the VH-encoding DNA to another DNA molecule encoding heavy chain constant regions (CH1, CH2 and CH3). The sequences of human heavy chain constant region genes are known in the art (see e.g., Kabat, E. A., et al. (1991)

Sequences of Proteins of Immunological Interest, Fifth Edition, U.S. Department of Health and Human Services, NIH Publication No. 91-3242) and DNA fragments encompassing these regions can be obtained by standard PCR amplification. The heavy chain constant region can be an IgG1, IgG2, IgG3, IgG4, IgA, IgE, IgM or IgD constant region, but most preferably is an IgG1 or IgG4 constant region. For a Fab fragment heavy chain gene, the $V_H$-encoding DNA can be operatively linked to another DNA molecule encoding only the heavy chain CH1 constant region.

The isolated DNA encoding the $V_K$ region can be converted to a full-length light chain gene (as well as a Fab light chain gene) by operatively linking the $V_K$-encoding DNA to another DNA molecule encoding the light chain constant region, CL. The sequences of human light chain constant region genes are known in the art (see e.g., Kabat, E. A., et al. (1991) Sequences of Proteins of Immunological Interest, Fifth Edition, U.S. Department of Health and Human Services, NIH Publication No. 91-3242) and DNA fragments encompassing these regions can be obtained by standard PCR amplification. In preferred embodiments, the light chain constant region can be a kappa or lambda constant region.

To create a scFv gene, the $V_H$- and $V_K$-encoding DNA fragments are operatively linked to another fragment encoding a flexible linker, e.g., encoding the amino acid sequence $(Gly_4-Ser)_3$, such that the $V_H$ and $V_K$ sequences can be expressed as a contiguous single-chain protein, with the $V_K$ and $V_H$ regions joined by the flexible linker (see e.g., Bird et al. (1988) *Science* 242:423-426; Huston et al. (1988) *Proc. Natl. Acad. Sci. USA* 85:5879-5883; McCafferty et al., (1990) *Nature* 348:552-554).

Production of Monoclonal Antibodies of this Disclosure

Monoclonal antibodies (mAbs) of the present disclosure can be produced by a variety of techniques, including conventional monoclonal antibody methodology e.g., the standard somatic cell hybridization technique of Kohler and Milstein (1975) *Nature* 256: 495. Although somatic cell hybridization procedures are preferred, in principle, other techniques for producing monoclonal antibody can be employed e.g., viral or oncogenic transformation of B lymphocytes.

The preferred animal system for preparing hybridomas is the murine system. Hybridoma production in the mouse is a very well-established procedure. Immunization protocols and techniques for isolation of immunized splenocytes for fusion are known in the art. Fusion partners (e.g., murine myeloma cells) and fusion procedures are also known.

Chimeric or humanized antibodies of the present disclosure can be prepared based on the sequence of a non-human monoclonal antibody prepared as described above. DNA encoding the heavy and light chain immunoglobulins can be obtained from the non-human hybridoma of interest and engineered to contain non-murine (e.g., human) immunoglobulin sequences using standard molecular biology techniques. For example, to create a chimeric antibody, murine variable regions can be linked to human constant regions using methods known in the art (see e.g., U.S. Pat. No. 4,816,567 to Cabilly et al.). To create a humanized antibody, murine CDR regions can be inserted into a human framework using methods known in the art (see e.g., U.S. Pat. No. 5,225,539 to Winter, and U.S. Pat. Nos. 5,530,101; 5,585,089; 5,693,762 and 6,180,370 to Queen et al.).

In a preferred embodiment, the antibodies of this disclosure are human monoclonal antibodies. Such human monoclonal antibodies directed against CTLA-4 can be generated using transgenic or transchromosomic mice carrying parts of the human immune system rather than the mouse system. These transgenic and transchromosomic mice include mice referred to herein as the HuMAb Mouse® strain and KM Mouse® strain, respectively, and are collectively referred to herein as "human Ig mice."

The HuMAb Mouse® strain (Medarex™, Inc.) contains human immunoglobulin gene miniloci that encode unrearranged human heavy (μ and γ) and κ light chain immunoglobulin sequences, together with targeted mutations that inactivate the endogenous μ and κ chain loci (see e.g., Lonberg, et al. (1994) *Nature* 368(6474): 856-859). Accordingly, the mice exhibit reduced expression of mouse IgM or κ, and in response to immunization, the introduced human heavy and light chain transgenes undergo class switching and somatic mutation to generate high affinity human IgGκ monoclonal antibodies (Lonberg, N. et al. (1994), supra; reviewed in Lonberg, N. (1994) *Handbook of Experimental Pharmacology* 113:49-101; Lonberg, N. and Huszar, D. (1995) *Intern. Rev. Immunol.* 13: 65-93, and Harding, F. and Lonberg, N. (1995) *Ann. N.Y. Acad. Sci.* 764:536-546). Preparation and use of the HuMAb Mouse® strain, and the genomic modifications carried by such mice, is further described in Taylor, L. et al. (1992) *Nucleic Acids Research* 20:6287-6295; Chen, J. et al. (1993) *International Immunology* 5: 647-656; Tuaillon et al. (1993) *Proc. Natl. Acad. Sci. USA* 90:3720-3724; Choi et al. (1993) *Nature Genetics* 4:117-123; Chen, J. et al. (1993) *EMBO J.* 12: 821-830; Tuaillon et al. (1994) *J. Immunol.* 152:2912-2920; Taylor, L. et al. (1994) *International Immunology* 6: 579-591; and Fishwild, D. et al. (1996) *Nature Biotechnology* 14: 845-851, the contents of all of which are hereby specifically incorporated by reference in their entirety. See further, U.S. Pat. Nos. 5,545,806; 5,569,825; 5,625,126; 5,633,425; 5,789,650; 5,877,397; 5,661,016; 5,814,318; 5,874,299; and 5,770,429; all to Lonberg and Kay; U.S. Pat. No. 5,545,807 to Surani et al.; PCT Publication Nos. WO 92/03918, WO 93/12227, WO 94/25585, WO 97/13852, WO 98/24884 and WO 99/45962, all to Lonberg and Kay; and PCT Publication No. WO 01/14424 to Korman et al.

In another embodiment, human antibodies of this disclosure can be raised using a mouse that carries human immunoglobulin sequences on transgenes and transchromosomes, such as a mouse that carries a human heavy chain transgene and a human light chain transchromosome. This mouse is referred to herein as a "KM Mouse® strain," and is described in detail in PCT Publication WO 02/43478 to Ishida et al.

Still further, alternative transgenic animal systems expressing human immunoglobulin genes are available in the art and can be used to raise anti-CTLA-4 antibodies of this disclosure. For example, an alternative transgenic system referred to as the Xenomouse (Abgenix, Inc.) can be used; such mice are described in, for example, U.S. Pat. Nos. 5,939,598; 6,075,181; 6,114,598; 6,150,584 and 6,162,963 to Kucherlapati et al.

Moreover, alternative transchromosomic animal systems expressing human immunoglobulin genes are available in the art and can be used to raise anti-CTLA-4 antibodies of this disclosure. For example, mice carrying both a human heavy chain transchromosome and a human light chain transchromosome, referred to as "TC mice" can be used; such mice are described in Tomizuka et al. (2000) *Proc. Natl. Acad. Sci. USA* 97:722-727. Furthermore, cows carrying human heavy and light chain transchromosomes have been described in the art (e.g., Kuroiwa et al. (2002) *Nature Biotechnology* 20:889-894 and PCT application No. WO 2002/092812) and can be used to raise anti-CTLA-4 antibodies of this disclosure.

Human monoclonal antibodies of this disclosure can also be prepared using phage display methods for screening libraries of human immunoglobulin genes. Such phage display methods for isolating human antibodies are established in the art. See for example: U.S. Pat. Nos. 5,223,409; 5,403,484; and 5,571,698 to Ladner et al.; U.S. Pat. Nos. 5,427,908 and 5,580,717 to Dower et al.; U.S. Pat. Nos. 5,969,108 and 6,172,197 to McCafferty et al.; and U.S. Pat. Nos. 5,885,793; 6,521,404; 6,544,731; 6,555,313; 6,582,915 and 6,593,081 to Griffiths et al.

Human monoclonal antibodies of this disclosure can also be prepared using SCID mice into which human immune cells have been reconstituted such that a human antibody response can be generated upon immunization. Such mice are described in, for example, U.S. Pat. Nos. 5,476,996 and 5,698,767 to Wilson et al.

In another embodiment, human anti-CTLA-4 antibodies are prepared using a combination of human Ig mouse and phage display techniques, as described in U.S. Pat. No. 6,794,132 by Buechler et al. More specifically, the method first involves raising an anti-CTLA-4 antibody response in a human Ig mouse (such as a HuMab strain mouse or KM strain mouse as described above) by immunizing the mouse with a CTLA-4 antigen, followed by isolating nucleic acids encoding human antibody chains from lymphatic cells of the mouse and introducing these nucleic acids into a display vector (e.g., phage) to provide a library of display packages. Thus, each library member comprises a nucleic acid encoding a human antibody chain and each antibody chain is displayed from the display package. The library then is screened with a CTLA-4 antigen to isolate library members that specifically bind CTLA-4. Nucleic acid inserts of the selected library members then are isolated and sequenced by standard methods to determine the light and heavy chain variable sequences of the selected CTLA-4 binders. The variable regions can be converted to full-length antibody chains by standard recombinant DNA techniques, such as cloning of the variable regions into an expression vector that carries the human heavy and light chain constant regions such that the $V_H$ region is operatively linked to the $C_H$ region and the $V_K$ region is operatively linked to the $C_L$ region.

Immunization of Human Ig Mice

When human Ig mice are used to raise human antibodies of this disclosure, such mice can be immunized with a purified or enriched preparation of CTLA-4 antigen and/or recombinant CTLA-4, or cells expressing CTLA-4, or a CTLA-4 fusion protein, as described by Lonberg, N. et al. (1994) Nature 368(6474): 856-859; Fishwild, D. et al. (1996) Nature Biotechnology 14: 845-851; and PCT Publication WO 98/24884 and WO 01/14424. Preferably, the mice will be 6-16 weeks of age upon the first infusion. For example, a purified or recombinant preparation (5-50 µg) of CTLA-4 antigen can be used to immunize the human Ig mice intraperitoneally. More preferably, the immunogen used to raise the antibodies of this disclosure is a combination of recombinant CTLA-4 soluble fusion protein and cells that express CTLA-4 on the cell surface.

Detailed procedures to generate fully human monoclonal antibodies to CTLA-4 are described in Example 1 below. Cumulative experience with various antigens has shown that the transgenic mice respond when initially immunized intraperitoneally (IP) with antigen in complete Freund's adjuvant, followed by every other week IP immunizations (up to a total of 6) with antigen in incomplete Freund's adjuvant. However, adjuvants other than Freund's are also found to be effective. In addition, whole cells in the absence of adjuvant are found to be highly immunogenic. The immune response can be monitored over the course of the immunization protocol with plasma samples being obtained by retroorbital bleeds. The plasma can be screened by ELISA (as described below), and mice with sufficient titers of anti-CTLA-4 human immunoglobulin can be used for fusions. Mice can be boosted intravenously with antigen 3 days before sacrifice and removal of the spleen. It is expected that 2-3 fusions for each immunization may need to be performed. Between 6 and 24 mice are typically immunized for each antigen. Usually both HCo7 and HCo12 strains are used. In addition, both HCo7 and HCo12 transgene can be bred together into a single mouse having two different human heavy chain transgenes (HCo7/HCo12).

Generation of Hybridomas Producing Human Monoclonal Antibodies of this Disclosure To generate hybridomas producing human monoclonal antibodies of this disclosure, splenocytes and/or lymph node cells from immunized mice can be isolated and fused to an appropriate immortalized cell line, such as a mouse myeloma cell line. The resulting hybridomas can be screened for the production of antigen-specific antibodies. For example, single cell suspensions of splenic lymphocytes from immunized mice can be fused to one-sixth the number of P3X63-Ag8.653 nonsecreting mouse myeloma cells (ATCC, CRL 1580) with 50% PEG. Alternatively, the single cell suspension of splenic lymphocytes from immunized mice can be fused using an electric field based electrofusion method, using a CytoPulse large chamber cell fusion electroporator (CytoPulse Sciences, Inc., Glen Burnie Md.). Cells are plated at approximately $2\times10^5$ in flat bottom microtiter plate, followed by a two week incubation in selective medium containing 20% fetal Clone Serum, 18% "653" conditioned media, 5% origen (IGEN), 4 mM L-glutamine, 1 mM sodium pyruvate, 5 mM HEPES, 0.055 mM 2-mercaptoethanol, 50 units/ml penicillin, 50 mg/ml streptomycin, 50 mg/ml gentamycin and 1×HAT (Sigma; the HAT is added 24 hours after the fusion). After approximately two weeks, cells can be cultured in medium in which the HAT is replaced with HT. Individual wells can then be screened by ELISA for human monoclonal IgM and IgG antibodies. Once extensive hybridoma growth occurs, medium can be observed usually after 10-14 days. The antibody secreting hybridomas can be replated, screened again, and if still positive for human IgG, the monoclonal antibodies can be subcloned at least twice by limiting dilution. The stable subclones can then be cultured in vitro to generate small amounts of antibody in tissue culture medium for characterization.

To purify human monoclonal antibodies, selected hybridomas can be grown in two-liter spinner-flasks for monoclonal antibody purification. Supernatants can be filtered and concentrated before affinity chromatography with protein A-sepharose (Pharmacia, Piscataway, N.J.). Eluted IgG can be checked by gel electrophoresis and high performance liquid chromatography to ensure purity. The buffer solution can be exchanged into PBS, and the concentration can be determined by OD280 using 1.43 extinction coefficient. The monoclonal antibodies can be aliquoted and stored at –80° C.

Generation of Transfectomas Producing Monoclonal Antibodies of this Disclosure

Antibodies of this disclosure also can be produced in a host cell transfectoma using, for example, a combination of recombinant DNA techniques and gene transfection methods as is well known in the art (e.g., Morrison, S. (1985) Science 229:1202).

For example, to express the antibodies, or antibody fragments thereof, DNAs encoding partial or full-length light and heavy chains, can be obtained by standard molecular biology techniques (e.g., PCR amplification or cDNA cloning using a hybridoma that expresses the antibody of interest) and the DNAs can be inserted into expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vector or, more typically, both genes are inserted into the same expression vector. The antibody genes are inserted into the expression vector by standard methods (e.g., ligation of complementary restriction sites on the antibody gene fragment and vector, or blunt end ligation if no restriction sites are present). The light and heavy chain variable regions of the antibodies described herein can be used to create full-length antibody genes of any antibody isotype by inserting them into expression vectors already encoding heavy chain constant and light chain constant regions of the desired isotype such that the $V_H$ segment is operatively linked to the $C_H$ segment(s) within the vector and the $V_K$ segment is operatively linked to the $C_L$ segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes, the recombinant expression vectors of this disclosure carry regulatory sequences that control the expression of the antibody chain genes in a host cell. The term "regulatory sequence" is intended to include promoters, enhancers and other expression control elements (e.g., polyadenylation signals) that control the transcription or translation of the antibody chain genes. Such regulatory sequences are described, for example, in Goeddel (Gene Expression Technology. Methods in Enzymology 185, Academic Press, San Diego, Calif. (1990)). It will be appreciated by those skilled in the art that the design of the expression vector, including the selection of regulatory sequences, may depend on such factors as the choice of the host cell to be transformed, the level of expression of protein desired, etc. Preferred regulatory sequences for mammalian host cell expression include viral elements that direct high levels of protein expression in mammalian cells, such as promoters and/or enhancers derived from cytomegalovirus (CMV), Simian Virus 40 (SV40), adenovirus, (e.g., the adenovirus major late promoter (AdMLP) and polyoma. Alternatively, nonviral regulatory sequences may be used, such as the ubiquitin promoter or β-globin promoter. Still further, regulatory elements composed of sequences from different sources, such as the SRα promoter system, which contains sequences from the SV40 early promoter and the long terminal repeat of human T cell leukemia virus type 1 (Takebe, Y. et al. (1988) *Mol. Cell. Biol.* 8:466-472).

In addition to the antibody chain genes and regulatory sequences, the recombinant expression vectors of this disclosure may carry additional sequences, such as sequences that regulate replication of the vector in host cells (e.g., origins of replication) and selectable marker genes. The selectable marker gene facilitates selection of host cells into which the vector has been introduced (see, e.g., U.S. Pat. Nos. 4,399,216, 4,634,665 and 5,179,017, all by Axel et al.). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr-host cells with methotrexate selection/amplification) and the neo gene (for G418 selection).

For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is theoretically possible to express the antibodies of this disclosure in either prokaryotic or eukaryotic host cells, expression of antibodies in eukaryotic cells, and most preferably mammalian host cells, is the most preferred because such eukaryotic cells, and in particular mammalian cells, are more likely than prokaryotic cells to assemble and secrete a properly folded and immunologically active antibody. Prokaryotic expression of antibody genes has been reported to be ineffective for production of high yields of active antibody (Boss, M. A. and Wood, C. R. (1985) *Immunology Today* 6:12-13).

Preferred mammalian host cells for expressing the recombinant antibodies of this disclosure include Chinese Hamster Ovary (CHO cells) (including dhfr− CHO cells, described in Urlaub and Chasin, (1980) *Proc. Natl. Acad. Sci. USA* 77:4216-4220, used with a DHFR selectable marker, e.g., as described in R. J. Kaufman and P. A. Sharp (1982) *J. Mol. Biol.* 159:601-621), NSO myeloma cells, COS cells and SP2 cells. In particular, for use with NSO myeloma cells, another preferred expression system is the GS gene expression system disclosed in WO 87/04462 (to Wilson), WO 89/01036 (to Bebbington) and EP 338,841 (to Bebbington). When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Characterization of Antibody Binding to Antigen

Antibodies of the invention can be tested for binding to CTLA-4 by, for example, standard ELISA. Briefly, microtiter plates are coated with purified and/or recombinant CTLA-4 (e.g., soluble human CTLA-4 fusion protein) at 0.25 µg/ml in PBS, and then blocked with 5% bovine serum albumin in PBS. Dilutions of antibody (e.g., dilutions of plasma from CTLA-4-immunized mice) are added to each well and incubated for 1-2 hours at 37° C. The plates are washed with PBS/Tween and then incubated with secondary reagent (e.g., for human antibodies, a goat-anti-human IgG Fc-specific polyclonal reagent) conjugated to alkaline phosphatase for 1 hour at 37° C. After washing, the plates are developed with pNPP substrate (1 mg/ml), and analyzed at OD of 405-650. Preferably, mice that develop the highest titers will be used for fusions.

An ELISA assay as described above can also be used to screen for hybridomas that show positive reactivity with CTLA-4 immunogen. Hybridomas that bind with high avidity to CTLA-4 are subcloned and further characterized. One clone from each hybridoma, which retains the reactivity of the parent cells (by ELISA), can be chosen for making a 5-10 vial cell bank stored at −140° C., and for antibody purification.

To purify anti-CTLA-4 antibodies, selected hybridomas can be grown in two-liter spinner-flasks for monoclonal antibody purification. Supernatants can be filtered and concentrated before affinity chromatography with protein A-sepharose (Pharmacia, Piscataway, N.J.). Eluted IgG can be checked by gel electrophoresis and high performance liquid chromatography to ensure purity. The buffer solution can be exchanged into PBS, and the concentration can be determined by OD280 using 1.43 extinction coefficient. The monoclonal antibodies can be aliquoted and stored at −80° C.

To determine if the selected anti-CTLA-4 monoclonal antibodies bind to unique epitopes, each antibody can be biotinylated using commercially available reagents (Pierce, Rockford, Ill.). Competition studies using unlabeled monoclonal antibodies and biotinylated monoclonal antibodies can be performed using CTLA-4 coated-ELISA plates as described above. Biotinylated mAb binding can be detected with a strep-avidin-alkaline phosphatase probe.

To determine the isotype of purified antibodies, isotype ELISAs can be performed using reagents specific for antibodies of a particular isotype. For example, to determine the isotype of a human monoclonal antibody, wells of microtiter plates can be coated with 1 μg/ml of anti-human immunoglobulin overnight at 4° C. After blocking with 1% BSA, the plates are reacted with 1 μg/ml or less of test monoclonal antibodies or purified isotype controls, at ambient temperature for one to two hours. The wells can then be reacted with either human IgG1 or human IgM-specific alkaline phosphatase-conjugated probes. Plates are developed and analyzed as described above.

Anti-CTLA-4 human IgGs can be further tested for reactivity with CTLA-4 antigen by Western blotting. Briefly, CTLA-4 can be prepared and subjected to sodium dodecyl sulfate polyacrylamide gel electrophoresis. After electrophoresis, the separated antigens are transferred to nitrocellulose membranes, blocked with 10% fetal calf serum, and probed with the monoclonal antibodies to be tested. Human IgG binding can be detected using anti-human IgG alkaline phosphatase and developed with BCIP/NBT substrate tablets (Sigma Chem. Co., St. Louis, Mo.).

The binding specificity of an antibody of this disclosure may also be determined by monitoring binding of the antibody to cells expressing CTLA-4, for example by flow cytometry. A cell line that naturally expresses CTLA-4 may be used or a cell line, such as a CHO cell line, may be transfected with an expression vector encoding a transmembrane form of CTLA-4. Another example of a cell line expressing CTLA-4 is the BW-huCTLA-4CD3ζ cell line, which is a murine T cell hybridoma that expresses the extracellular and transmembrane domain of human CTLA-4 fused to the intracellular domain of murine CD3ζ (described in Keler et al. (2003) *J. Immunol.* 171:6251-6259). The transfected protein may comprise a tag, such as a myc-tag, preferably at the N-terminus, for detection using an antibody to the tag. Binding of an antibody of this disclosure to CTLA-4 may be determined by incubating the transfected cells with the antibody, and detecting bound antibody. Binding of an antibody to the tag on the transfected protein may be used as a positive control.

Immunoconjugates

In another aspect, the present disclosure features an anti-CTLA-4 antibody, or a fragment thereof, conjugated to a therapeutic moiety, such as a cytotoxin, a drug (e.g., an immunosuppressant) or a radiotoxin. Such conjugates are referred to herein as "immunoconjugates". Immunoconjugates that include one or more cytotoxins are referred to as "immunotoxins." A cytotoxin or cytotoxic agent includes any agent that is detrimental to (e.g., kills) cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents also include, for example, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

Other preferred examples of therapeutic cytotoxins that can be conjugated to an antibody of this disclosure include duocarmycins, calicheamicins, maytansines and auristatins, and derivatives thereof. An example of a calicheamicin antibody conjugate is commercially available (Mylotarg®; American Home Products).

Cytotoxins can be conjugated to antibodies of this disclosure using linker technology available in the art. Examples of linker types that have been used to conjugate a cytotoxin to an antibody include, but are not limited to, hydrazones, thioethers, esters, disulfides and peptide-containing linkers. A linker can be chosen that is, for example, susceptible to cleavage by low pH within the lysosomal compartment or susceptible to cleavage by proteases, such as proteases preferentially expressed in tumor tissue such as cathepsins (e.g., cathepsins B, C, D).

For further discussion of types of cytotoxins, linkers and methods for conjugating therapeutic agents to antibodies, see also Saito, G. et al. (2003) *Adv. Drug Deliv. Rev.* 55:199-215; Trail, P. A. et al. (2003) *Cancer Immunol. Immunother.* 52:328-337; Payne, G. (2003) *Cancer Cell* 3:207-212; Allen, T. M. (2002) *Nat. Rev. Cancer* 2:750-763; Pastan, I. and Kreitman, R. J. (2002) *Curr. Opin. Investig. Drugs* 3:1089-1091; Senter, P. D. and Springer, C. J. (2001) *Adv. Drug Deliv. Rev.* 53:247-264.

Antibodies of the present disclosure also can be conjugated to a radioactive isotope to generate cytotoxic radiopharmaceuticals, also referred to as radioimmunoconjugates. Examples of radioactive isotopes that can be conjugated to antibodies for use diagnostically or therapeutically include, but are not limited to, iodine$^{131}$, indium$^{111}$, yttrium$^{90}$ and lutetium$^{177}$. Methods for preparing radio-immunconjugates are established in the art. Examples of radioimmunoconjugates are commercially available, including Zevalin® (IDEC Pharmaceuticals) and Bexxar® (Corixa Pharmaceuticals), and similar methods can be used to prepare radioimmunoconjugates using the antibodies of this disclosure.

The antibody conjugates of this disclosure can be used to modify a given biological response, and the drug moiety is not to be construed as limited to classical chemical therapeutic agents. For example, the drug moiety may be a protein or polypeptide possessing a desired biological activity. Such proteins may include, for example, an enzymatically active toxin, or active fragment thereof, such as abrin, ricin A, pseudomonas exotoxin, or diphtheria toxin; a protein such as tumor necrosis factor or interferon-γ; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Techniques for conjugating such therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., *Immunol. Rev.*, 62:119-58 (1982).

Bispecific Molecules

In another aspect, the present disclosure features bispecific molecules comprising an anti-CTLA-4 antibody, or a fragment thereof, of this disclosure. An antibody of this disclosure, or antigen-binding portions thereof, can be derivatized or linked to another functional molecule, e.g., another peptide or protein (e.g., another antibody or ligand for a receptor) to generate a bispecific molecule that binds to at least two different binding sites or target molecules. The antibody of this disclosure may in fact be derivatized or linked to more than one other functional molecule to generate multispecific molecules that bind to more than two different binding sites and/or target molecules; such multispecific molecules are also intended to be encompassed by the term "bispecific molecule" as used herein. To create a bispecific molecule of this disclosure, an antibody of this disclosure can be functionally linked (e.g., by chemical coupling, genetic fusion, noncovalent association or otherwise) to one or more other binding molecules, such as another antibody, antibody fragment, peptide or binding mimetic, such that a bispecific molecule results.

Accordingly, the present disclosure includes bispecific molecules comprising at least one first binding specificity for CTLA-4 and a second binding specificity for a second target epitope. In a particular embodiment of this disclosure, the second target epitope is an Fc receptor, e.g., human FcγRI (CD64) or a human Fcα receptor (CD89). Therefore, this disclosure includes bispecific molecules capable of binding both to FcγR or FcαR expressing effector cells (e.g., monocytes, macrophages or polymorphonuclear cells (PMNs)), and to target cells expressing CTLA-4. These bispecific molecules target CTLA-4 expressing cells to effector cell and trigger Fc receptor-mediated effector cell activities, such as phagocytosis of CTLA-4 expressing cells, antibody dependent cell-mediated cytotoxicity (ADCC), cytokine release, or generation of superoxide anion.

In an embodiment of this disclosure in which the bispecific molecule is multispecific, the molecule can further include a third binding specificity, in addition to an anti-Fc binding specificity and an anti-CTLA-4 binding specificity. In one embodiment, the third binding specificity is an anti-enhancement factor (EF) portion, e.g., a molecule which binds to a surface protein involved in cytotoxic activity and thereby increases the immune response against the target cell. The "anti-enhancement factor portion" can be an antibody, functional antibody fragment or a ligand that binds to a given molecule, e.g., an antigen or a receptor, and thereby results in an enhancement of the effect of the binding determinants for the Fc receptor or target cell antigen. The "anti-enhancement factor portion" can bind an Fc receptor or a target cell antigen. Alternatively, the anti-enhancement factor portion can bind to an entity that is different from the entity to which the first and second binding specificities bind. For example, the anti-enhancement factor portion can bind a cytotoxic T-cell (e.g. via CD2, CD3, CD8, CD28, CD4, CD40, ICAM-1 or other immune cell that results in an increased immune response against the target cell).

In one embodiment, the bispecific molecules of this disclosure comprise as a binding specificity at least one antibody, or an antibody fragment thereof, including, e.g., an Fab, Fab', F(ab')$_2$, Fv, Fd, dAb or a single chain Fv. The antibody may also be a light chain or heavy chain dimer, or any minimal fragment thereof such as a Fv or a single chain construct as described in U.S. Pat. No. 4,946,778 to Ladner et al., the contents of which is expressly incorporated by reference.

In one embodiment, the binding specificity for an Fcγ receptor is provided by a monoclonal antibody, the binding of which is not blocked by human immunoglobulin G (IgG). As used herein, the term "IgG receptor" refers to any of the eight γ-chain genes located on chromosome 1. These genes encode a total of twelve transmembrane or soluble receptor isoforms which are grouped into three Fcγ receptor classes: FcγRI (CD64), FcγRII (CD32), and FcγRIII (CD16). In one preferred embodiment, the Fcγ receptor a human high affinity FcγRI. The human FcγRI is a 72 kDa molecule, which shows high affinity for monomeric IgG ($10^8$-$10^9$ M$^{-1}$).

The production and characterization of certain preferred anti-Fcγ monoclonal antibodies are described in PCT Publication WO 88/00052 and in U.S. Pat. No. 4,954,617 to Fanger et al., the teachings of which are fully incorporated by reference herein. These antibodies bind to an epitope of FcγRI, FcγRII or FcγRIII at a site which is distinct from the Fcγ binding site of the receptor and, thus, their binding is not blocked substantially by physiological levels of IgG. Specific anti-FcγRI antibodies useful in this disclosure are mAb 22, mAb 32, mAb 44, mAb 62 and mAb 197. The hybridoma producing mAb 32 is available from the American Type Culture Collection, ATCC Accession No. HB9469. In other embodiments, the anti-Fcγ receptor antibody is a humanized form of monoclonal antibody 22 (H22). The production and characterization of the H22 antibody is described in Graziano, R. F. et al. (1995) *J. Immunol.* 155 (10): 4996-5002 and PCT Publication WO 94/10332 to Tempest et al. The H22 antibody producing cell line was deposited at the American Type Culture Collection under the designation HA022CL1 and has the accession no. CRL 11177.

In still other preferred embodiments, the binding specificity for an Fc receptor is provided by an antibody that binds to a human IgA receptor, e.g., an Fc-alpha receptor (FcαRI (CD89)), the binding of which is preferably not blocked by human immunoglobulin A (IgA). The term "IgA receptor" is intended to include the gene product of one α-gene (FcαRI) located on chromosome 19. This gene is known to encode several alternatively spliced transmembrane isoforms of 55 to 110 kDa. FcαRI (CD89) is constitutively expressed on monocytes/macrophages, eosinophilic and neutrophilic granulocytes, but not on non-effector cell populations. FcαRI has medium affinity ($\approx 5\times10^7$ M$^{-1}$) for both IgA1 and IgA2, which is increased upon exposure to cytokines such as G-CSF or GM-CSF (Morton, H. C. et al. (1996) *Critical Reviews in Immunology* 16:423-440). Four FcαRI-specific monoclonal antibodies, identified as A3, A59, A62 and A77, which bind FcαRI outside the IgA ligand binding domain, have been described (Monteiro, R. C. et al. (1992) *J. Immunol.* 148: 1764).

FcαRI and FcγRI are preferred trigger receptors for use in the bispecific molecules of this disclosure because they are (1) expressed primarily on immune effector cells, e.g., monocytes, PMNs, macrophages and dendritic cells; (2) expressed at high levels (e.g., 5,000-100,000 per cell); (3) mediators of cytotoxic activities (e.g., ADCC, phagocytosis); and (4) mediate enhanced antigen presentation of antigens, including self-antigens, targeted to them.

While human monoclonal antibodies are preferred, other antibodies which can be employed in the bispecific molecules of this disclosure are murine, chimeric and humanized monoclonal antibodies.

The bispecific molecules of the present disclosure can be prepared by conjugating the constituent binding specificities, e.g., the anti-FcR and anti-CTLA-4 binding specificities, using methods known in the art. For example, each binding specificity of the bispecific molecule can be generated separately and then conjugated to one another. When the binding specificities are proteins or peptides, a variety of coupling or cross-linking agents can be used for covalent conjugation. Examples of cross-linking agents include protein A, carbodiimide, N-succinimidyl-5-acetyl-thioacetate (SATA), 5,5'-dithiobis(2-nitrobenzoic acid) (DTNB), o-phenylenedi-maleimide (oPDM), N-succinimidyl-3-(2-pyridyldithio) propionate (SPDP), and sulfosuccinimidyl 4-(N-maleimidomethyl)cyclohaxane-1-carboxylate (sulfo-SMCC) (see e.g., Karpovsky et al. (1984) *J. Exp. Med.* 160: 1686; Liu, M A et al. (1985) *Proc. Natl. Acad. Sci. USA* 82:8648). Other methods include those described in Paulus (1985) Behring Ins. Mitt. No. 78, 118-132; Brennan et al. (1985) *Science* 229:81-83, and Glennie et al. (1987) *J. Immunol.* 139: 2367-2375). Preferred conjugating agents are SATA and sulfo-SMCC, both available from Pierce Chemical Co. (Rockford, Ill.).

When the binding specificities are antibodies, they can be conjugated via sulfhydryl bonding of the C-terminus hinge regions of the two heavy chains. In a particularly preferred embodiment, the hinge region is modified to contain an odd number of sulfhydryl residues, preferably one, prior to conjugation.

Alternatively, both binding specificities can be encoded in the same vector and expressed and assembled in the same host cell. This method is particularly useful where the bispecific molecule is a mAb×mAb, mAb×Fab, Fab×F(ab')$_2$ or ligand× Fab fusion protein. A bispecific molecule of this disclosure can be a single chain molecule comprising one single chain antibody and a binding determinant, or a single chain bispecific molecule comprising two binding determinants. Bispecific molecules may comprise at least two single chain molecules. Methods for preparing bispecific molecules are described for example in U.S. Pat. Nos. 5,260,203; 5,455,030; 4,881,175; 5,132,405; 5,091,513; 5,476,786; 5,013,653; 5,258,498; and 5,482,858, all of which are expressly incorporated herein by reference.

Binding of the bispecific molecules to their specific targets can be confirmed by, for example, enzyme-linked immunosorbent assay (ELISA), radioimmunoassay (RIA), FACS analysis, bioassay (e.g., growth inhibition), or Western Blot assay. Each of these assays generally detects the presence of protein-antibody complexes of particular interest by employing a labeled reagent (e.g., an antibody) specific for the complex of interest. For example, the FcR-antibody complexes can be detected using e.g., an enzyme-linked antibody or antibody fragment which recognizes and specifically binds to the antibody-FcR complexes. Alternatively, the complexes can be detected using any of a variety of other immunoassays. For example, the antibody can be radioactively labeled and used in a radioimmunoassay (RIA) (see, for example, Weintraub, B., Principles of Radioimmunoassays, Seventh Training Course on Radioligand Assay Techniques, The Endocrine Society, March, 1986, which is incorporated by reference herein). The radioactive isotope can be detected by such means as the use of a γcounter or a scintillation counter or by autoradiography.

Pharmaceutical Compositions

In another aspect, the present disclosure provides a composition, e.g., a pharmaceutical composition, containing one or a combination of monoclonal antibodies, or antigen-binding portion(s) thereof, of the present disclosure, formulated together with a pharmaceutically acceptable carrier. Such compositions may include one or a combination of (e.g., two or more different) antibodies, or immunoconjugates or bispecific molecules of this disclosure. For example, a pharmaceutical composition of this disclosure can comprise a combination of antibodies (or immunoconjugates or bispecifics) that bind to different epitopes on the target antigen or that have complementary activities.

Pharmaceutical compositions of this disclosure also can be administered in combination therapy, i.e., combined with other agents. For example, the combination therapy can include an anti-CTLA-4 antibody of the present disclosure combined with at least one other anti-cancer, anti-inflammatory or immunosuppressant agent. Examples of therapeutic agents that can be used in combination therapy are described in greater detail below in the section on uses of the antibodies of this disclosure.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). Depending on the route of administration, the active compound, i.e., antibody, immunoconjugate, or bispecific molecule, may be coated in a material to protect the compound from the action of acids and other natural conditions that may inactivate the compound.

The pharmaceutical compounds of this disclosure may include one or more pharmaceutically acceptable salts. A "pharmaceutically acceptable salt" refers to a salt that retains the desired biological activity of the parent compound and does not impart any undesired toxicological effects (see e.g., Berge, S. M., et al. (1977) *J. Pharm. Sci.* 66:1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A pharmaceutical composition of this disclosure also may include a pharmaceutically acceptable anti-oxidant. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Examples of suitable aqueous and nonaqueous carriers that may be employed in the pharmaceutical compositions of this disclosure include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of this disclosure is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. Generally, out of one hundred percent, this amount will range from about 0.01 percent to about ninety-nine percent of active ingredient, preferably from about 0.1 percent to about 70 percent, most preferably from about 1 percent to about 30 percent of active ingredient in combination with a pharmaceutically acceptable carrier.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of this disclosure are dictated by and directly dependent on (a) the unique characteristics of the active compound and the particular therapeutic effect to be achieved, and (b) the limitations inherent in the art of compounding such an active compound for the treatment of sensitivity in individuals.

For administration of the antibody, the dosage ranges from about 0.0001 to 100 mg/kg, and more usually 0.01 to 5 mg/kg, of the host body weight. For example dosages can be 0.3 mg/kg body weight, 1 mg/kg body weight, 3 mg/kg body weight, 5 mg/kg body weight or 10 mg/kg body weight or within the range of 1-10 mg/kg. An exemplary treatment regime entails administration once per week, once every two weeks, once every three weeks, once every four weeks, once a month, once every 3 months or once every three to 6 months. Preferred dosage regimens for an anti-CTLA-4 antibody of this disclosure include 1 mg/kg body weight or 3 mg/kg body weight via intravenous administration, with the antibody being given using one of the following dosing schedules: (i) every four weeks for six dosages, then every three months; (ii) every three weeks; (iii) 3 mg/kg body weight once followed by 1 mg/kg body weight every three weeks.

In some methods, two or more monoclonal antibodies with different binding specificities are administered simultaneously, in which case the dosage of each antibody administered falls within the ranges indicated. Antibody is usually administered on multiple occasions. Intervals between single dosages can be, for example, weekly, monthly, every three months or yearly. Intervals can also be irregular as indicated by measuring blood levels of antibody to the target antigen in the patient. In some methods, dosage is adjusted to achieve a plasma antibody concentration of about 1-1000 μg/ml and in some methods about 25-300 μg/ml.

Alternatively, antibody can be administered as a sustained release formulation, in which case less frequent administration is required. Dosage and frequency vary depending on the half-life of the antibody in the patient. In general, human antibodies show the longest half life, followed by humanized antibodies, chimeric antibodies, and nonhuman antibodies.

The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime.

Actual dosage levels of the active ingredients in the pharmaceutical compositions of the present disclosure may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present disclosure employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A "therapeutically effective dosage" of an anti-CTLA-4 antibody of this disclosure preferably results in a decrease in severity of disease symptoms, an increase in frequency and duration of disease symptom-free periods, or a prevention of impairment or disability due to the disease affliction. For example, for the treatment of tumors, a "therapeutically effective dosage" preferably inhibits cell growth or tumor growth by at least about 20%, more preferably by at least about 40%, even more preferably by at least about 60%, and still more preferably by at least about 80% relative to untreated subjects. The ability of a compound to inhibit tumor growth can be evaluated in an animal model system predictive of efficacy in human tumors. Alternatively, this property of a composition can be evaluated by examining the ability of the compound to inhibit cell growth, such inhibition can be measured in vitro by assays known to the skilled practitioner. A therapeutically effective amount of a therapeutic compound can decrease tumor size, or otherwise ameliorate symptoms in a subject. One of ordinary skill in the art would be able to determine such amounts based on such factors as the subject's size, the severity of the subject's symptoms, and the particular composition or route of administration selected.

A composition of the present disclosure can be administered via one or more routes of administration using one or more of a variety of methods known in the art. As will be appreciated by the skilled artisan, the route and/or mode of administration will vary depending upon the desired results. Preferred routes of administration for antibodies of this disclosure include intravenous, intramuscular, intradermal, intraperitoneal, subcutaneous, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Alternatively, an antibody of this disclosure can be administered via a non-parenteral route, such as a topical, epidermal or mucosal route of administration, for example, intranasally, orally, vaginally, rectally, sublingually or topically.

The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978.

Therapeutic compositions can be administered with medical devices known in the art. For example, in a preferred embodiment, a therapeutic composition of this disclosure can be administered with a needleless hypodermic injection device, such as the devices disclosed in U.S. Pat. Nos. 5,399,163; 5,383,851; 5,312,335; 5,064,413; 4,941,880; 4,790,824; or 4,596,556. Examples of well-known implants and modules useful in the present disclosure include: U.S. Pat. No. 4,487,603, which discloses an implantable micro-infusion pump for dispensing medication at a controlled rate; U.S. Pat. No. 4,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. These patents are incorporated herein by reference. Many other such implants, delivery systems, and modules are known to those skilled in the art.

In certain embodiments, the human monoclonal antibodies of this disclosure can be formulated to ensure proper distribution in vivo. For example, the blood-brain barrier (BBB) excludes many highly hydrophilic compounds. To ensure that the therapeutic compounds of this disclosure cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs, thus enhance targeted drug delivery (see, e.g., V. V. Ranade (1989) *J. Clin. Pharmacol.* 29:685). Exemplary targeting moieties include folate or biotin (see, e.g., U.S. Pat. No. 5,416,016 to Low et al.); mannosides (Umezawa et al., (1988) *Biochem. Biophys. Res. Commun.* 153:1038); antibodies (P. G. Bloeman et al. (1995) *FEBS Lett.* 357:140; M. Owais et al. (1995) *Antimicrob. Agents Chemother.* 39:180); surfactant protein A receptor (Briscoe et al. (1995) *Am. J. Physiol.* 1233:134); p120 (Schreier et al. (1994) *J. Biol. Chem.* 269:9090); see also K. Keinanen; M. L. Laukkanen (1994) *FEBS Lett.* 346:123; J. J. Killion; I. J. Fidler (1994) *Immunomethods* 4:273.

Uses and Methods of the Invention

The antibodies, antibody compositions and methods of the present invention have numerous in vitro and in vivo utilities involving, for example, detection of CTLA-4 or enhancement of immune response by blockade of CTLA-4. In a preferred embodiment, the antibodies of the present invention are human antibodies. For example, these molecules can be administered to cells in culture, in vitro or ex vivo, or to human subjects, e.g., in vivo, to enhance immunity in a variety of situations. Accordingly, in one aspect, the invention provides a method of modifying an immune response in a subject comprising administering to the subject the antibody, or antigen-binding portion thereof, of the invention such that the immune response in the subject is modified. Preferably, the response is enhanced, stimulated or up-regulated.

As used herein, the term "subject" is intended to include human and non-human animals. Non-human animals includes all vertebrates, e.g., mammals and non-mammals, such as non-human primates, sheep, dogs, cats, cows, horses, chickens, amphibians, and reptiles, although mammals are preferred, such as non-human primates, sheep, dogs, cats, cows and horses. Preferred subjects are primates, including, for examples, humans, chimpanzees, cynomolgus monkeys and rhesus monkeys. Particularly preferred subjects include human patients in need of enhancement of an immune response. The methods are particularly suitable for treating human patients having a disorder that can be treated by augmenting the T-cell mediated immune responses. In a particular embodiment, the methods are particularly suitable for treatment of cancer cells in vivo. To achieve antigen-specific enhancement of immunity, the anti-CTLA-4 antibodies can be administered together with an antigen of interest. When antibodies to CTLA-4 are administered together with another agent, the two can be administered in either order or simultaneously.

The invention further provides methods for detecting the presence of human CTLA-4 antigen in a sample, or measuring the amount of human CTLA-4 antigen, comprising contacting the sample, and a control sample, with a human monoclonal antibody, or an antigen binding portion thereof, which specifically binds to human CTLA-4, under conditions that allow for formation of a complex between the antibody or portion thereof and human CTLA-4. The formation of a complex is then detected, wherein a difference complex formation between the sample compared to the control sample is indicative the presence of human CTLA-4 antigen in the sample.

Given the specific binding of the antibodies of the invention for CTLA-4, the antibodies of the invention can be used to specifically detect CTLA-4 expression on the surface of cells and, moreover, can be used to purify CTLA-4 via immunoaffinity purification.

Also within the scope of the invention are kits comprising the compositions (e.g., antibodies, human antibodies, immunoconjugates and bispecific molecules) of the invention and instructions for use. The kit can further contain a least one additional reagent, or one or more additional antibodies of the invention (e.g., an antibody having a complementary activity which binds to an epitope on the target antigen distinct from the first antibody). Kits typically include a label indicating the intended use of the contents of the kit. The term label includes any writing, or recorded material supplied on or with the kit, or which otherwise accompanies the kit.

Furthermore, the anti-CTLA-4 antibodies (and immunoconjugates and bispecific molecules) of the invention can be used in the following clinical or therapeutic settings.

Activating Immune Responses

CTLA-4 blockade using anti-CTLA-4 antibodies has been shown to activate immune responses both in animal models and in humans (Leach et al. (1996) *Science* 271:1734-1736; Hodi et al. (2003) *Proc. Natl. Acad. Sci. USA* 100:4712-4717; Phan et al. (2003) *Proc. Natl. Acad. Sci. USA* 100:8372-8377). Accordingly, the anti-CTLA-4 antibodies of the invention can be used to enhance immune responses in a subject by administering the antibody to the subject, alone or in combination with other agents. For example, antibodies to CTLA-4 can be combined with an immunogenic agent, such as cancerous cells, purified tumor antigens (including recombinant proteins, peptides, and carbohydrate molecules), viral or bacterial pathogens, cells, and cells transfected with genes encoding immune stimulating cytokines and cell surface antigens such as B7 (see e.g., Hurwitz, A. et al. (1998) *Proc. Natl. Acad. Sci. U.S.A.* 95:10067-10071). Accordingly, the methods of the invention for activating an immune response can be used in clinical situations including, but not limited to, the treatment of cancers, the treatment of infectious diseases, the improvement of vaccination protocols and stimulation of autoimmune reactivites, as discussed further below.

Cancer

Blockade of CTLA-4 by antibodies can enhance the immune response to cancerous cells in a patient. Thus, in one aspect, the present invention relates to treatment of a subject in vivo using an anti-CTLA-4 antibody such that growth of cancerous tumors is inhibited. An anti-CTLA-4 antibody may be used alone to inhibit the growth of cancerous tumors. Alternatively, an anti-CTLA-4 antibody may be used in conjunction with other immunogenic agents, standard cancer treatments, or other antibodies, as described below.

Accordingly, in one embodiment, the invention provides a method of inhibiting growth of tumor cells in a subject, comprising administering to the subject a therapeutically effective amount of an anti-CTLA-4 antibody, or antigen-binding portion thereof, disclosed herein. Preferably, the antibody is a human anti-CTLA-4 antibody (such as any of the human anti-human CTLA-4 antibodies described herein). Additionally or alternatively, the antibody may be a chimeric or humanized anti-CTLA-4 antibody.

Preferred cancers whose growth may be inhibited using the antibodies of the invention include cancers typically responsive to immunotherapy. Non-limiting examples of preferred cancers for treatment include melanoma (e.g., metastatic malignant melanoma), renal cancer (e.g. clear cell carcinoma), prostate cancer (e.g. hormone refractory prostate adenocarcinoma), breast cancer, colon cancer and lung cancer (e.g. non-small cell lung cancer). Additionally, the invention includes refractory or recurrent malignancies whose growth may be inhibited using the antibodies of the invention.

Examples of other cancers that may be treated using the methods of the invention include bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, and combinations of said cancers. The present invention is also useful for treatment of metastatic cancers.

Optionally, antibodies to CTLA-4 can be combined with an immunogenic agent, such as cancerous cells, purified tumor antigens (including recombinant proteins, peptides, and carbohydrate molecules), cells, and cells transfected with genes encoding immune stimulating cytokines (He et al (2004) *J. Immunol.* 173:4919-28). Non-limiting examples of tumor vaccines that can be used include peptides of melanoma antigens, such as peptides of gp100, MAGE antigens, Trp-2, MART1 and/or tyrosinase, or tumor cells transfected to express the cytokine GM-CSF (discussed further below).

In certain instances, CTLA-4 blockade may be more effective when combined with a vaccination protocol. Many experimental strategies for vaccination against tumors have been devised (see Rosenberg, S., 2000, Development of Cancer Vaccines, ASCO Educational Book Spring: 60-62; Logothetis, C., 2000, ASCO Educational Book Spring: 300-302; Khayat, D. 2000, ASCO Educational Book Spring: 414-428; Foon, K. 2000, ASCO Educational Book Spring: 730-738; see also Restifo, N. and Sznol, M., Cancer Vaccines, Ch. 61, pp. 3023-3043 in DeVita, V. et al. (eds.), 1997, Cancer: Principles and Practice of Oncology. Fifth Edition). In one of these strategies, a vaccine is prepared using autologous or allogeneic tumor cells. These cellular vaccines have been shown to be most effective when the tumor cells are transduced to express GM-CSF. GM-CSF has been shown to be a potent activator of antigen presentation for tumor vaccination (Dranoff et al. (1993) *Proc. Natl. Acad. Sci. U.S.A.* 90: 3539-43).

The study of gene expression and large scale gene expression patterns in various tumors has led to the definition of so called tumor specific antigens (Rosenberg, S A (1999) *Immunity* 10: 281-7). In many cases, these tumor specific antigens are differentiation antigens expressed in the tumors and in the cell from which the tumor arose, for example melanocyte antigens gp100, MAGE antigens, and Trp-2. More importantly, many of these antigens can be shown to be the targets of tumor specific T cells found in the host. CTLA-4 blockade may be used in conjunction with a collection of recombinant proteins and/or peptides expressed in a tumor in order to generate an immune response to these proteins. These proteins are normally viewed by the immune system as self antigens and are therefore tolerant to them. The tumor antigen may also include the protein telomerase, which is required for the synthesis of telomeres of chromosomes and which is expressed in more than 85% of human cancers and in only a limited number of somatic tissues (Kim, N et al. (1994) *Science* 266: 2011-2013). (These somatic tissues may be protected from immune attack by various means). Tumor antigen may also be "neo-antigens" expressed in cancer cells because of somatic mutations that alter protein sequence or create fusion proteins between two unrelated sequences (i.e. bcr-abl in the Philadelphia chromosome), or idiotype from B cell tumors.

Other tumor vaccines may include the proteins from viruses implicated in human cancers such a Human Papilloma Viruses (HPV), Hepatitis Viruses (HBV and HCV) and Kaposi's Herpes Sarcoma Virus (KHSV). Another form of tumor specific antigen which may be used in conjunction with CTLA-4 blockade is purified heat shock proteins (HSP) isolated from the tumor tissue itself. These heat shock proteins contain fragments of proteins from the tumor cells and these HSPs are highly efficient at delivery to antigen presenting cells for eliciting tumor immunity (Suot, R & Srivastava, P (1995) *Science* 269:1585-1588; Tamura, Y. et al. (1997) Science 278:117-120).

Dendritic cells (DC) are potent antigen presenting cells that can be used to prime antigen-specific responses. DC's can be produced ex vivo and loaded with various protein and peptide antigens as well as tumor cell extracts (Nestle, F. et al. (1998) *Nature Medicine* 4: 328-332). DCs may also be transduced by genetic means to express these tumor antigens as well. DCs have also been fused directly to tumor cells for the purposes of immunization (Kugler, A. et al. (2000) *Nature Medicine* 6:332-336). As a method of vaccination, DC immunization may be effectively combined with CTLA-4 blockade to activate more potent anti-tumor responses.

CTLA-4 blockade may also be combined with standard cancer treatments. CTLA-4 blockade may be effectively combined with chemotherapeutic regimes. In these instances, it may be possible to reduce the dose of chemotherapeutic reagent administered (Mokyr, M. et al. (1998) *Cancer Research* 58: 5301-5304). An example of such a combination is an anti-CTLA-4 antibody in combination with decarbazine for the treatment of melanoma. Another example of such a combination is an anti-CTLA-4 antibody in combination with interleukin-2 (IL-2) for the treatment of melanoma. The scientific rationale behind the combined use of CTLA-4 blockade and chemotherapy is that cell death, which is a consequence of the cytotoxic action of most chemotherapeutic compounds, should result in increased levels of tumor antigen in the antigen presentation pathway. Other combination therapies that may result in synergy with CTLA-4 blockade through cell death are radiation, surgery, and hormone deprivation. Each of these protocols creates a source of tumor antigen in the host. Angiogenesis inhibitors may also be combined with CTLA-4 blockade. Inhibition of angiogenesis leads to tumor cell death which may feed tumor antigen into host antigen presentation pathways.

CTLA-4 blocking antibodies can also be used in combination with bispecific antibodies that target Fc alpha or Fc gamma receptor-expressing effectors cells to tumor cells (see, e.g., U.S. Pat. Nos. 5,922,845 and 5,837,243). Bispecific antibodies can be used to target two separate antigens. For example anti-Fc receptor/anti tumor antigen (e.g., Her-2/neu) bispecific antibodies have been used to target macrophages to sites of tumor. This targeting may more effectively activate tumor specific responses. The T cell arm of these responses would by augmented by the use of CTLA-4 blockade. Alternatively, antigen may be delivered directly to DCs by the use of bispecific antibodies which bind to tumor antigen and a dendritic cell specific cell surface marker.

In another example, a combination of anti-CTLA-4 antibodies can be used in conjunction with anti-neoplastic antibodies, such as Rituxan® (rituximab), Herceptin® (trastuzumab), Bexxar® (tositumomab), Zevalin® (ibritumomab), Campath® (alemtuzumab), Lymphocide® (eprtuzumab), Avastin® (bevacizumab), and Tarceva® (erlotinib), and the like. By way of example and not wishing to be bound by theory, treatment with an anti-cancer antibody or an anti-cancer antibody conjugated to a toxin can lead to cancer cell death (e.g., tumor cells) which would potentiate an immune response augmented by CTLA-4 blockade. In an exemplary embodiment, a treatment of a hyperproliferative disease (e.g., a cancer tumor) may include an anti-cancer antibody in combination with an anti-CTLA-4 antibody, concurrently or sequentially or any combination thereof, which may potentiate an anti-tumor immune responses by the host. Tumors evade host immune surveillance by a large variety of mechanisms. Many of these mechanisms may be overcome by the inactivation of proteins which are expressed by the tumors and which are immunosuppressive. These include among others TGF-beta (Kehrl, J. et al. (1986) *J. Exp. Med.* 163: 1037-1050), IL-10 (Howard, M. & O'Garra, A. (1992) *Immunology Today* 13: 198-200), and Fas ligand (Hahne, M. et al. (1996) *Science* 274: 1363-1365). Antibodies to each of these entities may be used in combination with anti-CTLA-4 to counteract the effects of the immunosuppressive agent and favor tumor immune responses by the host.

Other antibodies which may be used to activate host immune responsiveness can be used in combination with anti-CTLA-4. A particularly preferred antibody with which an anti-CTLA-4 antibody can be combined is an anti-PD-1 antibody (discussed in detail below). Other examples of antibodies for use in combination therapy include antibodies to molecules on the surface of dendritic cells which activate DC function and antigen presentation. Anti-CD40 antibodies are able to substitute effectively for T cell helper activity (Ridge, J. et al. (1998) *Nature* 393: 474-478) and can be used in conjunction with CTLA-4 antibodies (Ito, N. et al. (2000) *Immunobiology* 201 (5) 527-40). Activating antibodies to T cell costimulatory molecules such as OX-40 (Weinberg, A. et al. (2000) *Immunol* 164: 2160-2169), 4-1BB (Melero, I. et al. (1997) *Nature Medicine* 3: 682-685 (1997), and ICOS (Hutloff, A. et al. (1999) *Nature* 397: 262-266) may also provide for increased levels of T cell activation.

Bone marrow transplantation is currently being used to treat a variety of tumors of hematopoietic origin. While graft versus host disease is a consequence of this treatment, therapeutic benefit may be obtained from graft vs. tumor responses. CTLA-4 blockade can be used to increase the effectiveness of the donor engrafted tumor specific T cells.

There are also several experimental treatment protocols that involve ex vivo activation and expansion of antigen specific T cells and adoptive transfer of these cells into recipients in order to antigen-specific T cells against tumor (Greenberg, R. & Riddell, S. (1999) *Science* 285: 546-51). These methods may also be used to activate T cell responses to infectious agents such as CMV. Ex vivo activation in the presence of anti-CTLA-4 antibodies may be expected to increase the frequency and activity of the adoptively transferred T cells.

In further embodiments, CTLA-4 blockade can be further combined with the use of any non-absorbable steroid. As used herein, a "non-absorbable steroid" is a glucocorticoid that exhibits extensive first pass metabolism such that, following metabolism in the liver, the bioavailability of the steroid is low, i.e., less than about 20%. In one embodiment of the invention, the non-absorbable steroid is budesonide. Budesonide is a locally-acting glucocorticosteroid, which is extensively metabolized, primarily by the liver, following oral administration. ENTOCORT EC® (Astra-Zeneca) is a pH- and time-dependent oral formulation of budesonide developed to optimize drug delivery to the ileum and throughout the colon. ENTOCORT EC® is approved in the U.S. for the treatment of mild to moderate Crohn's disease involving the ileum and/or ascending colon. The usual oral dosage of ENTOCORT EC® for the treatment of Crohn's disease is 6 to 9 mg/day. ENTOCORT EC® is released in the intestines before being absorbed and retained in the gut mucosa. Once it passes through the gut mucosa target tissue, ENTOCORT EC® is extensively metabolized by the cytochrome P450 system in the liver to metabolites with negligible glucocorticoid activity. Therefore, the bioavailability is low (about 10%). The low bioavailability of budesonide results in an improved therapeutic ratio compared to other glucocorticoids with less extensive first-pass metabolism. Budesonide results in fewer adverse effects, including less hypothalamic-pituitary suppression, than systemically-acting corticosteroids. However, chronic administration of ENTOCORT EC® can result in systemic glucocorticoid effects such as hypercorticism and adrenal suppression. See PDR 58$^{th}$ ed. 2004; 608-610.

In still further embodiments, CTLA-4 blockade in conjunction with a non-absorbable steroid can be further combined with a salicylate. Salicylates include 5-ASA agents such as, for example: sulfasalazine (AZULFIDINE®, Pharmacia & UpJohn); olsalazine (DIPENTUM®, Pharmacia & UpJohn); balsalazide (COLAZAL®, Salix Pharmaceuticals, Inc.); and mesalamine (ASACOL®, Procter & Gamble Pharmaceuticals; PENTASA®, Shire US; CANASA®, Axcan Scandipharm, Inc.; ROWASA®, Solvay).

In accordance with the methods of the present invention, a salicylate administered in combination with an anti-CTLA-4 antibody and a non-absorbable steroid can include any overlapping or sequential administration of the salicylate and the non-absorbable steroid for the purpose of decreasing the incidence of colitis induced by the immunostimulatory antibody. Thus, for example, methods for reducing the incidence of colitis induced by the immunostimulatory antibody according to the present invention encompass administering a salicylate and a non-absorbable concurrently or sequentially (e.g., a salicylate is administered 6 hours after a non-absorbable steroid), or any combination thereof. Further, according to the present invention, a salicylate and a non-absorbable steroid can be administered by the same route (e.g., both are administered orally) or by different routes (e.g., a salicylate is administered orally and a non-absorbable steroid is administered rectally), which may differ from the route(s) used to administer the anti-CTLA-4 antibody.

Infectious Diseases

Other methods of the invention are used to treat patients that have been exposed to particular toxins or pathogens. Accordingly, another aspect of the invention provides a method of treating an infectious disease in a subject comprising administering to the subject an anti-CTLA-4 antibody, or antigen-binding portion thereof, as disclosed herein, such that the subject is treated for the infectious disease. Preferably, the antibody is a human anti-human CTLA-4 antibody (such as any of the human anti-CTLA-4 antibodies described herein). Additionally or alternatively, the antibody can be a chimeric or humanized antibody.

Similar to its application to tumors as discussed above, antibody mediated CTLA-4 blockade can be used alone, or as an adjuvant, in combination with vaccines, to stimulate the immune response to pathogens, toxins, and self-antigens. Examples of pathogens for which this therapeutic approach may be particularly useful, include pathogens for which there is currently no effective vaccine, or pathogens for which conventional vaccines are less than completely effective. These include, but are not limited to HIV, Hepatitis (A, B, & C), Influenza, Herpes, *Giardia*, Malaria, *Leishmania*, *Staphylococcus aureus*, *Pseudomonas Aeruginosa*. CTLA-4 blockade is particularly useful against established infections by agents such as HIV that present altered antigens over the course of the infections. These novel epitopes are recognized as foreign at the time of anti-human CTLA-4 administration, thus provoking a strong T cell response that is not dampened by negative signals through CTLA-4.

Some examples of pathogenic viruses causing infections treatable by methods of the invention include HIV, hepatitis (A, B, or C), herpes virus (e.g., VZV, HSV-1, HAV-6, HSV-II, and CMV, Epstein Barr virus), adenovirus, influenza virus, flaviviruses, echovirus, rhinovirus, coxsackie virus, cornovirus, respiratory syncytial virus, mumps virus, rotavirus, measles virus, rubella virus, parvovirus, vaccinia virus, HTLV virus, dengue virus, papillomavirus, molluscum virus, poliovirus, rabies virus, JC virus and arboviral encephalitis virus.

Some examples of pathogenic bacteria causing infections treatable by methods of the invention include *chlamydia*, rickettsial bacteria, mycobacteria, staphylococci, streptococci, pneumonococci, meningococci and conococci, *klebsiella, proteus, serratia, pseudomonas, legionella*, diphtheria, *salmonella*, bacilli, cholera, tetanus, botulism, anthrax, plague, leptospirosis, and Lymes disease bacteria.

Some examples of pathogenic fungi causing infections treatable by methods of the invention include *Candida* (*albicans, krusei, glabrata, tropicalis*, etc.), *Cryptococcus neoformans, Aspergillus* (*fumigatus, niger*, etc.), Genus Mucorales (*mucor, absidia, rhizophus*), *Sporothrix schenkii, Blastomyces dermatitidis, Paracoccidioides brasiliensis, Coccidioides immitis* and *Histoplasma capsulatum.*

Some examples of pathogenic parasites causing infections treatable by methods of the invention include *Entamoeba histolytica, Balantidium coli, Naegleria fowleri, Acanthamoeba* sp., *Giardia lambia, Cryptosporidium* sp., *Pneumocystis carinii, Plasmodium vivax, Babesia microti, Trypanosoma brucei, Trypanosoma cruzi, Leishmania donovani, Toxoplasma gondi, Nippostrongylus brasiliensis.*

In all of the above methods, CTLA-4 blockade can be combined with other forms of immunotherapy such as cytokine treatment (e.g., interferons, GM-CSF, G-CSF, IL-2), or bispecific antibody therapy, which provides for enhanced presentation of tumor antigens (see, e.g., Holliger (1993) *Proc. Natl. Acad. Sci. USA* 90:6444-6448; Poljak (1994) *Structure* 2:1121-1123).

Autoimmune Reactions

Anti-CTLA-4 antibodies may provoke and amplify autoimmune responses. Indeed, induction of anti-tumor responses using tumor cell and peptide vaccines reveals that many anti-tumor responses involve anti-self reactivities (depigmentation observed in anti-CTLA-4+GM-CSF-modified B16 melanoma in van Elsas et al. supra; depigmentation in Trp-2 vaccinated mice (Overwijk, W. et al. (1999) *Proc. Natl. Acad. Sci. U.S.A.* 96: 2982-2987); autoimmune prostatitis evoked by TRAMP tumor cell vaccines (Hurwitz, A. (2000) supra), melanoma peptide antigen vaccination and vitilago observed in human clinical trials (Rosenberg, S A and White, D E (1996) *J. Immunother Emphasis Tumor Immunol* 19 (1): 81-4)).

Therefore, it is possible to consider using anti-CTLA-4 blockade in conjunction with various self proteins in order to devise vaccination protocols to efficiently generate immune responses against these self proteins for disease treatment. For example, Alzheimers disease involves inappropriate accumulation of Aβ peptide in amyloid deposits in the brain; antibody responses against amyloid are able to clear these amyloid deposits (Schenk et al., (1999) *Nature* 400: 173-177).

Other self proteins may also be used as targets such as IgE for the treatment of allergy and asthma, and TNFα, for rheumatoid arthritis. Finally, antibody responses to various hormones may be induced by the use of anti-CTLA-4 antibody. Neutralizing antibody responses to reproductive hormones may be used for contraception. Neutralizing antibody response to hormones and other soluble factors that are required for the growth of particular tumors may also be considered as possible vaccination targets.

Analogous methods as described above for the use of anti-CTLA-4 antibody can be used for induction of therapeutic autoimmune responses to treat patients having an inappropriate accumulation of other self-antigens, such as amyloid deposits, including Aβ in Alzheimer's disease, cytokines such as TNFα, and IgE.

Vaccines

Anti-CTLA-4 antibodies may be used to stimulate antigen-specific immune responses by coadministration of an anti-CTLA-4 antibody with an antigen of interest (e.g., a vaccine).

Accordingly, in another aspect the invention provides a method of enhancing an immune response to an antigen in a subject, comprising administering to the subject: (i) the antigen; and (ii) an anti-CTLA-4 antibody, or antigen-binding portion thereof, as disclosed herein, such that an immune response to the antigen in the subject is enhanced. Preferably, the antibody is a human anti-human CTLA-4 antibody (such as any of the human anti-CTLA-4 antibodies described herein). Additionally or alternatively, the antibody can be a chimeric or humanized antibody. The antigen can be, for example, a tumor antigen, a viral antigen, a bacterial antigen or an antigen from a pathogen. Non-limiting examples of such antigens include those discussed in the sections above, such as the tumor antigens (or tumor vaccines) discussed above, or antigens from the viruses, bacteria or other pathogens described above.

Suitable routes of administering the antibody compositions (e.g., human monoclonal antibodies, multispecific and bispecific molecules and immunoconjugates) of the invention in vivo and in vitro are well known in the art and can be selected by those of ordinary skill. For example, the antibody compositions can be administered by injection (e.g., intravenous or subcutaneous). Suitable dosages of the molecules used will depend on the age and weight of the subject and the concentration and/or formulation of the antibody composition.

As previously described, human anti-CTLA-4 antibodies of the invention can be co-administered with one or other more therapeutic agents, e.g., a cytotoxic agent, a radiotoxic agent or an immunosuppressive agent. The antibody can be linked to the agent (as an immunocomplex) or can be administered separate from the agent. In the latter case (separate administration), the antibody can be administered before, after or concurrently with the agent or can be co-administered with other known therapies, e.g., an anti-cancer therapy, e.g., radiation. Such therapeutic agents include, among others, anti-neoplastic agents such as doxorubicin (adriamycin), cisplatin bleomycin sulfate, carmustine, chlorambucil, decarbazine and cyclophosphamide hydroxyurea which, by themselves, are only effective at levels which are toxic or subtoxic to a patient. Cisplatin is intravenously administered as a 100 mg/dose once every four weeks and adriamycin is intravenously administered as a 60-75 mg/ml dose once every 21 days. Co-administration of the human anti-CTLA-4 antibodies, or antigen binding fragments thereof, of the present invention with chemotherapeutic agents provides two anti-cancer agents which operate via different mechanisms which yield a cytotoxic effect to human tumor cells. Such co-administration can solve problems due to development of resistance to drugs or a change in the antigenicity of the tumor cells which would render them unreactive with the antibody.

Combination Therapy with Anti-PD-1 Antibodies

The anti-CTLA-4 antibodies, and antigen binding fragments thereof, as disclosed herein, can be used in combination with, for example, antibodies against PD-1. Thus, in one embodiment, the present invention provides a method for treating a hyperproliferative disease, comprising administering (i) an anti-CTLA-4 antibody, or antigen binding fragment thereof, as disclosed herein and (ii) an anti-PD-1 antibody, or antigen binding fragment thereof, to a subject. In further embodiments, the anti-CTLA-4 antibody is administered at a subtherapeutic dose, the anti-PD-1 antibody is administered at a subtherapeutic dose, or both are administered at a subtherapeutic dose. In another embodiment, the present invention provides a method for altering an adverse event associated with treatment of a hyperproliferative disease with an immunostimulatory agent, comprising administering an anti- PD-1 antibody and a subtherapeutic dose of anti-CTLA-4 antibody to a subject. In certain embodiments, the subject is human. Examples of suitable anti-PD-1 antibodies that can be used in the above-described combination methods are described in U.S. Provisional Patent No. 60/679,466.

Blockade of CTLA-4 and PD-1 by antibodies can enhance the immune response to cancerous cells in the patient. Cancers whose growth may be inhibited using the antibodies of the instant disclosure include cancers typically responsive to immunotherapy. Representative examples of cancers for treatment with the combination therapy of the instant disclosure include melanoma (e.g., metastatic malignant melanoma), renal cancer, prostate cancer, breast cancer, colon cancer and lung cancer. Examples of other cancers that may be treated using the methods of the instant disclosure include bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, and combinations of said cancers. The present invention is also useful for treatment of metastatic cancers.

In certain embodiments, the combination of therapeutic antibodies discussed herein may be administered concurrently as a single composition in a pharmaceutically acceptable carrier, or concurrently as separate compositions with each antibody in a pharmaceutically acceptable carrier. In another embodiment, the combination of therapeutic antibodies can be administered sequentially. For example, an anti-CTLA-4 antibody and an anti-PD-1 antibody can be administered sequentially, such as anti-CTLA-4 being administered first and anti-PD-1 second, or anti-PD-1 being administered first and anti-CTLA-4 second. Furthermore, if more than one dose of the combination therapy is administered sequentially, the order of the sequential administration can be reversed or kept in the same order at each time point of administration, sequential administrations may be combined with concurrent administrations, or any combination thereof. For example, the first administration of a combination anti-CTLA-4 antibody and anti-PD-1 antibody may be concurrent, the second administration may be sequential with anti-CTLA-4 first and anti-PD-1 second, and the third administration may be sequential with anti-PD-1 first and anti-CTLA-4 second, etc. Another representative dosing scheme may involve a first administration that is sequential with anti-CTLA-4 first and anti-PD-1 second, and subsequent administrations may be concurrent.

Optionally, the combination of anti-CTLA-4 and anti-PD-1 antibodies can be further combined with an immunogenic agent, such as cancerous cells, purified tumor antigens (including recombinant proteins, peptides, and carbohydrate molecules), cells, and cells transfected with genes encoding immune stimulating cytokines (He et al. (2004) *J. Immunol.* 173:4919-28). Non-limiting examples of tumor vaccines that can be used include peptides of melanoma antigens, such as peptides of gp100, MAGE antigens, Trp-2, MART1 and/or tyrosinase, or tumor cells transfected to express the cytokine GM-CSF (discussed further below). A combined CTLA-4 and PD-1 blockade can be further combined with a vaccination protocol. Many experimental strategies for vaccination against tumors have been devised (see Rosenberg, S. (2000) Development of Cancer Vaccines, ASCO Educational Book Spring: 60-62; Logothetis, C., 2000, ASCO Educational Book Spring: 300-302; Khayat, D. (2000) ASCO Educational Book Spring: 414-428; Foon, K. (2000) ASCO Educational Book Spring: 730-738; see also Restifo and Sznol, Cancer Vaccines, Ch. 61, pp. 3023-3043 in DeVita et al. (eds.), 1997, Cancer: Principles and Practice of Oncology. Fifth Edition). In one of these strategies, a vaccine is prepared using autologous or allogeneic tumor cells. These cellular vaccines have been shown to be most effective when the tumor cells are transduced to express GM-CSF. GM-CSF has been shown to be a potent activator of antigen presentation for tumor vaccination (Dranoff et al. (1993) *Proc. Natl. Acad. Sci. U.S.A.* 90: 3539-43).

The study of gene expression and large scale gene expression patterns in various tumors has led to the definition of so called tumor specific antigens (Rosenberg (1999) *Immunity* 10:281-7). In many cases, these tumor specific antigens are differentiation antigens expressed in the tumors and in the cell from which the tumor arose, for example melanocyte antigens gp 100, MAGE antigens, and Trp-2. More importantly, many of these antigens can be shown to be the targets of tumor specific T cells found in the host. In certain embodiments, a combined CTLA-4 and PD-1 blockade using the antibody compositions described herein may be used in conjunction with a collection of recombinant proteins and/or peptides expressed in a tumor in order to generate an immune response to these proteins. These proteins are normally viewed by the immune system as self-antigens and are, therefore, tolerant to them. The tumor antigen may also include the protein telomerase, which is required for the synthesis of telomeres of chromosomes and which is expressed in more than 85% of human cancers and in only a limited number of somatic tissues (Kim et al. (1994) *Science* 266: 2011-2013). (These somatic tissues may be protected from immune attack by various means). Tumor antigen may also be "neo-antigens" expressed in cancer cells because of somatic mutations that alter protein sequence or create fusion proteins between two unrelated sequences (i.e., bcr-abl in the Philadelphia chromosome), or idiotype from B cell tumors.

Other tumor vaccines may include the proteins from viruses implicated in human cancers such a Human Papilloma Viruses (HPV), Hepatitis Viruses (HBV and HCV) and Kaposi's Herpes Sarcoma Virus (KHSV). Another form of tumor specific antigen which may be used in conjunction with CTLA-4 blockade is purified heat shock proteins (HSP) isolated from the tumor tissue itself. These heat shock proteins contain fragments of proteins from the tumor cells and these HSPs are highly efficient at delivery to antigen presenting cells for eliciting tumor immunity (Suot & Srivastava (1995) *Science* 269:1585-1588; Tamura et al. (1997) *Science* 278: 117-120).

Dendritic cells (DC) are potent antigen presenting cells that can be used to prime antigen-specific responses. DC's can be produced ex vivo and loaded with various protein and peptide antigens as well as tumor cell extracts (Nestle et al.

(1998) *Nature Medicine* 4: 328-332). DCs may also be transduced by genetic means to express these tumor antigens as well. DCs have also been fused directly to tumor cells for the purposes of immunization (Kugler et al. (2000) *Nature Medicine* 6:332-336). As a method of vaccination, DC immunization may be effectively further combined with a combined CTLA-4 and PD-1 blockade to activate more potent anti-tumor responses.

A combined CTLA-4 and PD-1 blockade may also be further combined with standard cancer treatments. For example, a combined CTLA-4 and PD-1 blockade may be effectively combined with chemotherapeutic regimes. In these instances, as is observed with the combination of anti-CTLA-4 and anti-PD-1 antibodies, it may be possible to reduce the dose of other chemotherapeutic reagent administered with the combination of the instant disclosure (Mokyr et al. (1998) *Cancer Research* 58: 5301-5304). An example of such a combination is a combination of anti-CTLA-4 and anti-PD-1 antibodies further in combination with decarbazine for the treatment of melanoma. Another example is a combination of anti-CTLA-4 and anti-PD-1 antibodies further in combination with interleukin-2 (IL-2) for the treatment of melanoma. The scientific rationale behind the combined use of CTLA-4 and PD-1 blockade with chemotherapy is that cell death, which is a consequence of the cytotoxic action of most chemotherapeutic compounds, should result in increased levels of tumor antigen in the antigen presentation pathway. Other combination therapies that may result in synergy with a combined CTLA-4 and PD-1 blockade through cell death include radiation, surgery, or hormone deprivation. Each of these protocols creates a source of tumor antigen in the host. Angiogenesis inhibitors may also be combined with a combined CTLA-4 and PD-1 blockade. Inhibition of angiogenesis leads to tumor cell death, which may also be a source of tumor antigen to be fed into host antigen presentation pathways.

A combination of CTLA-4 and PD-1 blocking antibodies can also be used in combination with bispecific antibodies that target Fcα or Fcγ receptor-expressing effector cells to tumor cells (see, e.g., U.S. Pat. Nos. 5,922,845 and 5,837,243). Bispecific antibodies can be used to target two separate antigens. For example anti-Fc receptor/anti tumor antigen (e.g., Her-2/neu) bispecific antibodies have been used to target macrophages to sites of tumor. This targeting may more effectively activate tumor specific responses. The T cell arm of these responses would by augmented by the use of a combined CTLA-4 and PD-1 blockade. Alternatively, antigen may be delivered directly to DCs by the use of bispecific antibodies which bind to tumor antigen and a dendritic cell specific cell surface marker.

In another example, a combination of anti-CTLA-4 and anti-PD-1 antibodies can be used in conjunction with antineoplastic antibodies, such as Rituxan® (rituximab), Herceptin® (trastuzumab), Bexxar® (tositumomab), Zevalin® (ibritumomab), Campath® (alemtuzumab), Lymphocide® (eprtuzumab), Avastin® (bevacizumab), and Tarceva® (erlotinib), and the like. By way of example and not wishing to be bound by theory, treatment with an anti-cancer antibody or an anti-cancer antibody conjugated to a toxin can lead to cancer cell death (e.g., tumor cells) which would potentiate an immune response mediated by CTLA-4 or PD-1. In an exemplary embodiment, a treatment of a hyperproliferative disease (e.g., a cancer tumor) may include an anti-cancer antibody in combination with anti-CTLA-4 and anti-PD-1 antibodies, concurrently or sequentially or any combination thereof, which may potentiate an anti-tumor immune responses by the host.

Tumors evade host immune surveillance by a large variety of mechanisms. Many of these mechanisms may be overcome by the inactivation of proteins, which are expressed by the tumors and which are immunosuppressive. These include, among others, TGF-β (Kehrl, J. et al. (1986) *J. Exp. Med.* 163: 1037-1050), IL-10 (Howard, M. & O'Garra, A. (1992) *Immunology Today* 13: 198-200), and Fas ligand (Hahne, M. et al. (1996) *Science* 274: 1363-1365). In another example, antibodies to each of these entities may be further combined with an anti-CTLA-4 and anti-PD-1 combination to counteract the effects of immunosuppressive agents and favor anti-tumor immune responses by the host.

Other antibodies that may be used to activate host immune responsiveness can be further used in combination with an anti-CTLA-4 and anti-PD-1 combination. These include molecules on the surface of dendritic cells that activate DC function and antigen presentation. Anti-CD40 antibodies are able to substitute effectively for T cell helper activity (Ridge, J. et al. (1998) Nature 393: 474-478) and can be used in conjunction with an anti-CTLA-4 and anti-PD-1 combination (Ito, N. et al. (2000) *Immunobiology* 201 (5) 527-40). Activating antibodies to T cell costimulatory molecules, such as OX-40 (Weinberg, A. et al. (2000) *Immunol* 164: 2160-2169), 4-1BB (Melero, I. et al. (1997) *Nature Medicine* 3: 682-685 (1997), and ICOS (Hutloff, A. et al. (1999) *Nature* 397: 262-266) may also provide for increased levels of T cell activation.

Bone marrow transplantation is currently being used to treat a variety of tumors of hematopoietic origin. While graft versus host disease is a consequence of this treatment, therapeutic benefit may be obtained from graft vs. tumor responses. A combined CTLA-4 and PD-1 blockade can be used to increase the effectiveness of the donor engrafted tumor specific T cells.

There are also several experimental treatment protocols that involve ex vivo activation and expansion of antigen specific T cells and adoptive transfer of these cells into recipients in order to antigen-specific T cells against tumor (Greenberg, R. & Riddell, S. (1999) *Science* 285: 546-51). These methods may also be used to activate T cell responses to infectious agents such as CMV. Ex vivo activation in the presence of anti-CTLA-4 and anti-PD-1 antibodies may be expected to increase the frequency and activity of the adoptively transferred T cells.

Organs can exhibit immune-related adverse events following immunostimulatory therapeutic antibody therapy, such as the GI tract (diarrhea and colitis) and the skin (rash and pruritis) after treatment with anti-CTLA-4 antibody. For example, non-colonic gastrointestinal immune-related adverse events have also been observed in the esophagus (esophagitis), duodenum (duodenitis), and ileum (ileitis) after anti-CTLA-4 antibody treatment.

In certain embodiments, the present invention provides a method for altering an adverse event associated with treatment of a hyperproliferative disease with an immunostimulatory agent, comprising administering an anti-PD-1 antibody and a subtherapeutic dose of anti-CTLA-4 antibody to a subject. For example, the methods of the present invention provide for a method of reducing the incidence of immunostimulatory therapeutic antibody-induced colitis or diarrhea by administering a non-absorbable steroid to the patient. Because any patient who will receive an immunostimulatory therapeutic antibody is at risk for developing colitis or diarrhea induced by such an antibody, this entire patient population is suitable for therapy according to the methods of the present invention. Although steroids have been administered to treat inflammatory bowel disease (IBD) and prevent exacerbations of IBD, they have not been used to prevent (decrease the incidence of) IBD in patients who have not been diagnosed with IBD. The significant side effects associated with steroids, even non-absorbable steroids, have discouraged prophylactic use.

In further embodiments, a combination CTLA-4 and PD-1 blockade (i.e., immunostimulatory therapeutic antibodies anti-CTLA-4 and anti-PD-1) can be further combined with the use of any non-absorbable steroid. As used herein, a "non-absorbable steroid" is a glucocorticoid that exhibits extensive first pass metabolism such that, following metabolism in the liver, the bioavailability of the steroid is low, i.e., less than about 20%. In one embodiment of the invention, the non-absorbable steroid is budesonide. Budesonide is a locally-acting glucocorticosteroid, which is extensively metabolized, primarily by the liver, following oral administration. ENTOCORT EC® (Astra-Zeneca) is a pH- and time-dependent oral formulation of budesonide developed to optimize drug delivery to the ileum and throughout the colon. ENTOCORT EC® is approved in the U.S. for the treatment of mild to moderate Crohn's disease involving the ileum and/or ascending colon. The usual oral dosage of ENTOCORT EC® for the treatment of Crohn's disease is 6 to 9 mg/day. ENTOCORT EC® is released in the intestines before being absorbed and retained in the gut mucosa. Once it passes through the gut mucosa target tissue, ENTOCORT EC® is extensively metabolized by the cytochrome P450 system in the liver to metabolites with negligible glucocorticoid activity. Therefore, the bioavailability is low (about 10%). The low bioavailability of budesonide results in an improved therapeutic ratio compared to other glucocorticoids with less extensive first-pass metabolism. Budesonide results in fewer adverse effects, including less hypothalamic-pituitary suppression, than systemically-acting corticosteroids. However, chronic administration of ENTOCORT EC® can result in systemic glucocorticoid effects such as hypercorticism and adrenal suppression. See PDR 58$^{th}$ ed. 2004; 608-610.

In still further embodiments, a combination CTLA-4 and PD-1 blockade (i.e., immunostimulatory therapeutic antibodies anti-CTLA-4 and anti-PD-1) in conjunction with a non-absorbable steroid can be further combined with a salicylate. Salicylates include 5-ASA agents such as, for example: sulfasalazine (AZULFIDINE®, Pharmacia & UpJohn); olsalazine (DIPENTUM®, Pharmacia & UpJohn); balsalazide (COLAZAL®, *Salix* Pharmaceuticals, Inc.); and mesalamine (ASACOL®, Procter & Gamble Pharmaceuticals; PENTASA®, Shire US; CANASA®, Axcan Scandipharm, Inc.; ROWASA®, Solvay).

In accordance with the methods of the present invention, a salicylate administered in combination with anti-CTLA-4 and anti-PD-1 antibodies and a non-absorbable steroid can includes any overlapping or sequential administration of the salicylate and the non-absorbable steroid for the purpose of decreasing the incidence of colitis induced by the immunostimulatory antibodies. Thus, for example, methods for reducing the incidence of colitis induced by the immunostimulatory antibodies according to the present invention encompass administering a salicylate and a non-absorbable concurrently or sequentially (e.g., a salicylate is administered 6 hours after a non-absorbable steroid), or any combination thereof. Further, according to the present invention, a salicylate and a non-absorbable steroid can be administered by the same route (e.g., both are administered orally) or by different routes (e.g., a salicylate is administered orally and a non-absorbable steroid is administered rectally), which may differ from the route(s) used to administer the anti-CTLA-4 and anti-PD-1 antibodies.

The present invention is further illustrated by the following examples which should not be construed as further limiting. The contents of all figures and all references, patents and published patent applications cited throughout this application are expressly incorporated herein by reference.

Example 1

Generation of Human Anti-CTLA-4 Monoclonal Antibodies

Antigen Preparation

Soluble or cell-surface membrane-bound recombinant human CTLA-4 (prepared as described in PCT Publication WO 01/14424) were used as the antigens for immunization. For immunization of KM strain mice, a transfected cell that expresses a chimeric CTLA-4 molecule, comprising the extracelluar and transmembrane domains of human CTLA-4 linked to the intracellular domain of CD3 was used as the antigen (described further in Example 8 of U.S. Patent Publication No. 20020199213).

Transgenic and Transchromosomal Mice

Two different strains of transgenic HuMab mice were used to generate CTLA-4 reactive monoclonal antibodies, strain ((CMD)++; (JKD)++; (HCo7)11952+/++; (KCo5) 9272+/++), and strain ((CMD)++; (JKD)++; (HCo12) 15087+/++; (KCo5)9272+/++). Each of these strains is homozygous for disruptions of the endogenous heavy chain (CMD) and kappa light chain (JKD) loci. Both strains also comprise a human kappa light chain transgene (KCo5), with individual animals either hemizygous or homozygous for insertion of the transgene. The two strains differ in the human heavy chain transgene used. Mice were hemizygous or homozygous for either the HCo7 or the HCo12 heavy chain transgene. Generation of the CMD mutation is described in Example 1 of PCT Publication WO 01/14424. Generation of the (HCo12)15087 mice carrying the HCo12 human heavy chain transgene is described in Example 2 of WO 01/14424. Generation of the JKD mutation is described in Chen et al. (1993) *EMBO J.* 12: 811-820. Generation of the (KCo5)9272 strain of mice carrying the kappa transgene is described in Fishwild et al. (1996) *Nature Biotechnology* 14: 845-851. Generation of the (HCo7)11952 strain of mice carrying the HCo7 human heavy chain transgene is described in U.S. Pat. No. 5,770,429.

Anti-CTLA-4 antibodies also were generated using the transgenic, transchromosomic KM mouse strain. In this mouse strain, the endogenous mouse kappa light chain gene has been homozygously disrupted as described in Chen et al. (1993) *EMBO J.* 12:811-820 and the endogenous mouse heavy chain gene has been homozygously disrupted as described in Example 1 of PCT Publication WO 01/09187. Additionally, this mouse strain carries a human kappa light chain transgene, KCo5 (as described in Fishwild et al. (1996) *Nature Biotechnology* 14:845-851) and also contains the SC20 transchromosome, which carries the human Ig heavy chain locus, as described in PCT Publication WO 02/43478. KM strain mice are also described in detail in U.S. Patent Publication No. 20020199213.

Immunization

Transgenic mice were initially immunized intraperitoneally (i.p.) with 1-3×10$^7$ CTLA-4 expressing cells in PBS, or with 10-50 µg soluble fusion protein in adjuvant (either complete Freund's or Ribi). Immunized mice were subsequently boosted every 2 to 4 weeks i.p. with 1-3×10$^7$ cells in PBS. Animals were kept on protocol for 2 to 5 months. Prior to fusion, animals were boosted intravenously (i.v.) on days -3 and -2 with approximately 10⁶ cells, or with 10-20 µg soluble antigen. Some animals also received soluble protein i.v. on day -4. Successful fusions resulting in CTLA-4 reactive IgG kappa monoclonal antibodies were obtained from mice immunized by a variety of different protocols, including cells only, soluble antigen only, and cell immunizations followed by soluble antigen given i.v. prior to fusion.

KM strain mice were immunized as described in Example 8 of U.S. Patent Publication 20020199213.

Fusions

Spleen cells were fused to mouse myeloma cells (line P3X63 Ag8.6.53, ATCC CRL 1580, or SP2/0-Ag14, ATCC CRL 1581) by standard procedures (Harlow and Lane, 1988, *Antibodies, A Laboratory Manual*, Cold Spring Harbor Laboratory Press, Cold Spring Harbor N.Y.; Kennett et al. 1980, *Monoclonal Antibodies, Hybridomas: A New Dimension in Biological Analysis*. Plenum, N.Y.; Oi and Hertzenberg, 1980, *Immunoglobulin Producing Hybrid Cell Lines*, in *Selected Methods In Cellular Immunology*, ed. Mishell and Shiigi, pp. 357-372, Freeman, San Francisco; Halk, 1984, *Methods in Enzymology: Plant Molecular Biology*, ed. Weissbach and Weissbach, pp. 766-780, Academic Press, Orlando, Fla.). Cells were cultured in DMEM, 10% FBS, OPI (Sigma 0-5003), BME (Gibco 21985-023), 3% Origen Hybridoma Cloning Factor (Igen IG50-0615), and 5% P388d1 (ATCC TIB 63) conditioned media. HAT or HT supplement was added to the medium during initial growth and selection.

Hybridoma Screening

To identify hybridomas secreting human IgG kappa antibodies, ELISA plates (Nunc MaxiSorp) were coated overnight at 4° C. with 100 µg/well goat anti-human Fcγ specific antibody (Jackson Immuno Research #109-006-098) at 1 µg/ml in PBS. Plates were washed and blocked with 100 µl/well PBS-Tween containing 1% BSA. Fifty µl cell culture supernatant was added followed by a 1-2 hour incubation. Plates were washed and then incubated for one hour with 100 µl/well goat anti-Kappa light chain conjugated to alkaline phosphatase or horseradish peroxidase (Sigma #A-3813, or #A-7164). Plates were washed three times in PBS-Tween between each step. An analogous assay was used to identify hybridomas that secrete human antibodies reactive with human CTLA-4. This assay was identical except that the ELISA plates were coated with recombinant CTLA-4 fusion protein instead of goat anti-human Fcγ antibody.

Three hybridomas, secreting monoclonal antibodies 1H5 (obtained from a KM strain mouse), 3A4 (obtained from a HuMab mouse) and 6C10 (obtained from a HuMab mouse), respectively, were selected for further analysis.

Example 2

Structural Characterization of Human Monoclonal Antibodies

The cDNA sequences encoding the heavy and light chain variable regions of the 1H5, 3A4 and 6C10 monoclonal antibodies were obtained from their respective hybridomas using standard PCR techniques and were sequence using standard DNA sequencing techniques.

The nucleotide and amino acid sequences of the heavy chain variable region of 1H5 are shown in FIG. 1 and in SEQ ID NO: 37 and 28, respectively.

The nucleotide and amino acid sequences of the light chain variable region of 1H5 are shown in FIGS. 2A-2D and in SEQ ID NO: 40-43 and 31-34, respectively.

Comparison of the 1H5 heavy chain immunoglobulin sequence to the known human germline immunoglobulin heavy chain sequences demonstrated that the 1H5 heavy chain utilizes a $V_H$ segment from human germline $V_H$ 4-39, a D segment from human germline D 6-13 and a $J_H$ segment from human germline $J_H$ 6b. The alignment of the 1H5 $V_H$ sequence to the germline $V_H$ 4-39 sequence is shown in FIG. 7. Further analysis of the 1H5 VH sequence using the Kabat system of CDR region determination led to the delineation of the heavy chain CDR1, CDR2 and CD3 regions as shown in FIGS. 1 and 7, and in SEQ ID NOs: 1, 4 and 7, respectively.

Comparison of the 1H5 light chain immunoglobulin sequence to the known human germline immunoglobulin light chain sequences demonstrated that the 1H5 light chain utilizes a $V_k$ segment from human germline $V_k$ L-18 and a $J_k$ segment from human germline $J_k$ 4. The alignment of the 1H5 $V_k$ sequence to the germline $V_k$ L-18 sequence is shown in FIG. 7. Further analysis of the 1H5 Vk sequence using the Kabat system of CDR region determination led to the delineation of the light chain CDR1, CDR2 and CD3 regions as shown in FIGS. 2A-2D and 10, and in SEQ ID NOs: 10-15, 16-21 and 22-27, respectively.

The nucleotide and amino acid sequences of the heavy chain variable region of 3A4 are shown in FIG. 3 and in SEQ ID NO: 38 and 29, respectively.

The nucleotide and amino acid sequences of the light chain variable region of 3A4 are shown in FIG. 4 and in SEQ ID NO: 44 and 35, respectively.

Comparison of the 3A4 heavy chain immunoglobulin sequence to the known human germline immunoglobulin heavy chain sequences demonstrated that the 3A4 heavy chain utilizes a $V_H$ segment from human germline $V_H$ 3-33, a D segment from human germline D 6-13 and a $J_H$ segment from human germline $J_H$ 4b. The alignment of the 3A4 $V_H$ sequence to the germline $V_H$ 3-33 sequence is shown in FIG. 8. Further analysis of the 3A4 VH sequence using the Kabat system of CDR region determination led to the delineation of the heavy chain CDR1, CDR2 and CD3 regions as shown in FIGS. 3 and 8, and in SEQ ID NOs: 2, 5 and 8, respectively.

Comparison of the 3A4 light chain immunoglobulin sequence to the known human germline immunoglobulin light chain sequences demonstrated that the 3A4 light chain utilizes a $V_k$ segment from human germline $V_k$ L-15 and a $J_k$ segment from human germline $J_k$ 4. The alignment of the 3A4 $V_k$ sequence to the germline $V_k$ L-15 sequence is shown in FIG. 11. Further analysis of the 3A4 Vk sequence using the Kabat system of CDR region determination led to the delineation of the light chain CDR1, CDR2 and CD3 regions as shown in FIGS. 4 and 11, and in SEQ ID NOs: 14, 20 and 26, respectively.

The nucleotide and amino acid sequences of the heavy chain variable region of 6C10 are shown in FIG. 5 and in SEQ ID NO: 39 and 30, respectively.

The nucleotide and amino acid sequences of the light chain variable region of 6C10 are shown in FIG. 6 and in SEQ ID NO: 45 and 36, respectively.

Comparison of the 6C10 heavy chain immunoglobulin sequence to the known human immunoglobulin heavy chain sequences demonstrated that the 6C10 heavy chain utilizes a $V_H$ segment from human germline $V_H$ 3-33, a D segment from human germline D 6-19 and a $J_H$ segment from human germline $J_H$ 4b. The alignment of the 6C10 $V_H$ sequence to the germline $V_H$ 3-33 sequence is shown in FIG. 11. Further analysis of the 6C10 VH sequence using the Kabat system of CDR region determination led to the delineation of the heavy chain CDR1, CDR2 and CD3 regions as shown in FIGS. 5 and 9, and in SEQ ID NOs: 3, 6 and 9, respectively.

Comparison of the 6C10 light chain immunoglobulin sequence to the known human germline immunoglobulin light chain sequences demonstrated that the 6C10 light chain utilizes a $V_k$ segment from human germline $V_k$ L-15 and a $J_k$ segment from human germline $J_k$ 4. The alignment of the 6C10 $V_k$ sequence to the germline $V_k$ L-15 sequence is shown in FIG. 12. Further analysis of the 6C10 Vk sequence using the Kabat system of CDR region determination led to the delineation of the light chain CDR1, CDR2 and CD3 regions as shown in FIGS. 6 and 12, and in SEQ ID NOs: 15, 21 and 27, respectively.

Example 3

In Vitro Binding Characteristics of Anti-CTLA-4 Human Antibodies

Binding of Anti-CTLA-4 mAbs to Cell-Surface CTLA-4 Protein

A panel of anti-CTLA-4 monoclonal antibodies, including 1H5, 3A4 and 6C10 described in Example 2, was tested for binding to a transformed cell line that expresses the extracellular domain of human CTLA-4 on its cell surface. More specifically, the cell line expresses a chimeric CTLA-4 protein, comprising the extracellular and transmembrane domains of human CTLA-4 linked to the intracellular domain of CD3ζ (the cell line is described in, for example, Keler et al. (2003) *J. Immunol.* 171:6251-6259). Binding of the anti-CTLA-4 antibodies to the cells was evaluated in standard flow cytometry assays, as follows:

A three-fold dilution series of purified antibody ranging from 10 μg/ml (66.6 nM) to 4.6 ng/ml (0.03 nM) was incubated for one hour with $10^5$ cells in a volume of 100 μl of antibody dilution in PBS+1% BSA+0.05% sodium azide (FACS buffer). Cells were washed two times by centrifugation and resuspension in 200 μA of FACS buffer and then stained for 30-60 minutes in FACS buffer plus a 1:400 dilution of R-phycoerythrin (PE) labeled F(ab')$_2$ goat anti-human IgG antibody (Jackson ImmunoResearch). Cells were washed two times in FACS buffer and then analyzed by flow cytometry in a Guava PCA (Guava Technologies, Inc., Hayward, Calif.) or a FACSCalibur or FACSArray flow cytometer (Beckton, Dickinson and Co., San Jose, Calif.). A plot of the mean fluorescent intensity (MFI) versus log antibody concentration is shown in FIG. 13. The antibody TT shown in FIG. 13 is a human IgG1 k mAb specific for tetanus toxoid (TT), which was used as a negative control. The anti-CTLA4 antibody 10D1, previously described in WO 01/14424 and having VH and VK sequences as shown in SEQ ID NOs: 50 and 51 respectively, was used as a positive control.

The effective concentration ($EC_{50}$) to reach half maximal binding of antibody to cell expressed CTLA-4 was determined graphically using GraphPad Prizm (GraphPad Software, San Diego, Calif.). The $EC_{50}$ results, reported in nM, are shown below in Table 1.

TABLE 1

Binding of Anti-CTLA4 mAbs to Cell Surface CTLA4

| | 10D1 | 3A4 | 1H5 | 6C10 |
|---|---|---|---|---|
| $EC_{50}$ (nM) | 0.4147 | 0.6607 | 0.4374 | 0.2475 |

This in vitro binding assay confirmed that all of the anti-CTLA-4 human monoclonal antibodies examined bound well to human CTLA-4 expressed on the cell surface, as determined by FACS. In particular, mAbs 1H5, 3A4 and 6C10 all exhibited good binding to hCTLA4$^+$ cells in vitro, comparable to the 10D1 antibody.

Blocking of Binding of a Soluble Human CTLA-4 Fusion Protein to B7$^+$ Cells by Anti-CTLA-4 mAbs The panel of anti-CTLA-4 human monoclonal antibodies was tested for the ability of the antibodies to inhibit the binding of a soluble human CTLA-4 fusion protein to B7-1$^+$ cells. In particular, the 1H5, 3A4 and 6C10 antibodies, as well as the 10D1 antibody (as a positive control) and the anti-TT antibody (as a negative control) were used in an in vitro binding assay in which each antibody was mixed with a CTLA-4-Ig fusion protein (comprising the extracellular domain of CTLA-4 fused to the Fc region of human immunoglobulin; e.g., commercially obtained from R&D Systems) and the mixture was applied to cells transformed to express mouse B7-1 on the cell surface. Binding of CTLA-4-Ig to the B7-1 expressing cells was detected by incubation with a phycoerythrin-labeled goat anti-human Ig Fc-specific antibody, followed by flow cytometry.

Figure 14:
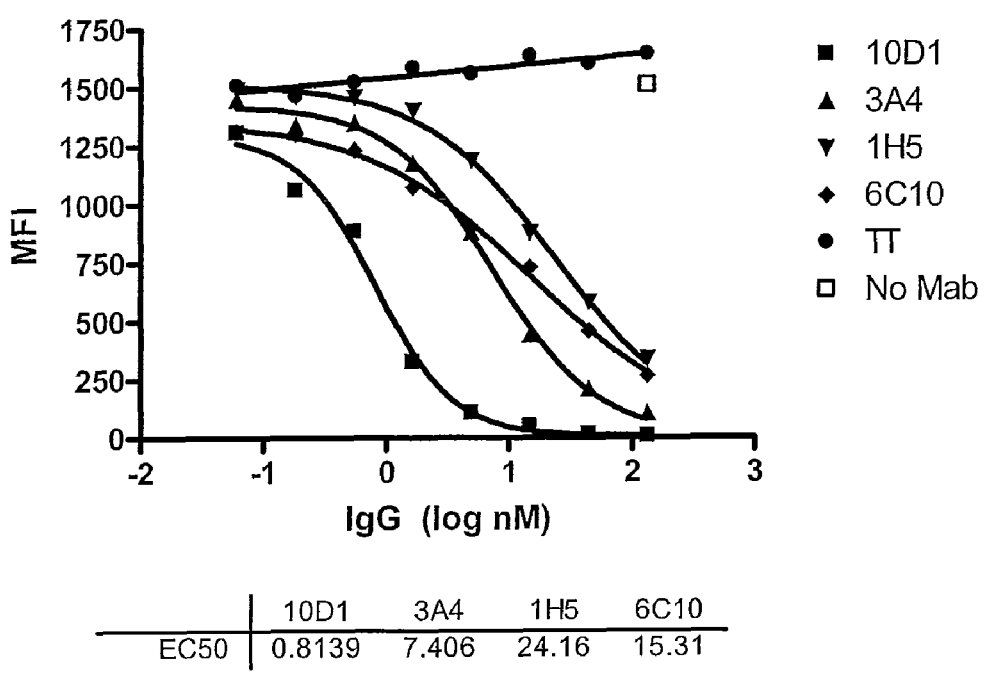
FIG. 14 is a graph showing the inhibition of binding of CTLA-4-Ig fusion protein to cells expressing mouse B7-1 by a panel of anti-CTLA-4 antibodies, as assessed by flow cytometry.

CTLA-4 Hu Ig (R & D Systems) was incubated with dilutions of antibody for 30-60 minutes. The antibody CTLA-4 Ig mix was then added to $10^5$ B7.1 4D3 cells in 100 μl of FACS buffer. The cells, CTLA-4 Ig, and antibody mix was incubated for 1 hour at 4° C., and then washed two times by centrifugation of the cells, aspiration of the supernatant, and resuspension of the cells in FACS buffer. CTLA-4 Ig binding to B7.1 on the cell surface was detected by staining the cells for 30-60 minutes in 100 μl of FACS buffer containing a 1:400 dilution of R-phycoerythrin (PE) labeled F(ab')$_2$ goat anti-human IgG antibody (Jackson ImmunoResearch). Cells were then washed and analyzed by flow cytometry. A plot of the mean fluorescent intensity (MFI) versus log antibody concentration is shown in FIG. 14.

The $EC_{50}$ values for antibodies blocking binding of CTLA-4 Ig to B7.1 were determined graphically (GraphPad Prizm) from a plot of MFI versus Log IgG concentrations. The $EC_{50}$ results, expressed in nM, are shown below in Table 2.

TABLE 2

Inhibition of CTLA4-Ig Binding to B7-1 Expressing Cells by Anti-CTLA4 mAb

| | 10D1 | 3A4 | 1H5 | 6C10 |
|---|---|---|---|---|
| $EC_{50}$ (nM) | 0.8139 | 7.406 | 24.16 | 15.31 |

This in vitro antibody blocking assay demonstrated that human mAbs 1H5, 3A4 and 6C10 all exhibited a greatly reduced ability to inhibit the binding of soluble human CTLA-4-Ig protein to B7-1 expressing cells, as compared to the control anti-CTLA4 antibody 10D1. In particular, each antibody exhibited at least a 9-fold greater $EC_{50}$ (in nM) as compared to the control 10D1 antibody. For example, the 3A4 antibody exhibited approximately a 9.09 fold greater $EC_{50}$ than 10D1, the 1H5 antibody exhibited approximately a 29.68 fold greater $EC_{50}$ than 10D1 and the 6C10 antibody exhibited approximately a 18.81 fold greater $EC_{50}$ than 10D1.

Example 4

In Vivo Immunostimulatory Activity of Anti-CTLA-4 Human Antibodies

In this example, a multi-dose study was conducted in cynomolgus monkeys to evaluate the ability of anti-CTLA-4 human antibodies to enhance the immune response to co-administered immunostimulants.

Eighteen animals were divided into three test groups of six animals each, referred to as Groups 1, 2 and 3. Each group received one of three test agents intravenously, as follows: Group 1: saline (as a negative control), Group 2: 10D1 antibody (10 mg/kg) and Group 3: 1H5 antibody (10 mg/kg). The test agent was administered on Days 1, 29 and 57 of the experiment. Two immunostimulants were used in each animal, SKMel-3 (a malignant melanoma cell line; available from American Type Culture Collection, Rockville, Md.; Catalog #HTB-69; $5 \times 10^6$ cells administered subcutaneously) and hepatitis B surface antigen (HbsAg; available from Aldevron, Fago, N D, Catalog #201-1000; 10 µg administered intramuscularly). The SKMel-3 cells and HbsAg were administered on Days 1, 29 and 57.

Plasma samples were taken from each test animal on Days 14, 30, 43, 58, 71, 85 and 100 and examined for specific antibodies to SKMel-3 or HbsAg. Peripheral blood samples also were taken from each test animal on Days 14, 30, 43, 58, 71, 85 and 100 and examined for the presence of various subsets of lymphocytes.

Humoral Immune Responses

The antibody response to the SKMel-3 cells was evaluated by flow cytometry as follows. Freshly prepared SKMel-3 cells were incubated in suspension with plasma samples at 4° C. to allow antibody binding to surface molecules. After washing the cells, antibodies bound to the cells were detected with a phycoerythrin-conjugated F(ab')$_2$ goat anti-human IgG, Fcγ-specific reagent. The cell-associated fluorescence was measured using a FACScaliber flow cytometer (Becton Dickinson) and the geometric mean fluorescence intensity (GMFI) of the samples was calculated using FlowJo analysis software (Treestar, Inc.). The results of the FACS analysis are summarized below in Table 3:

TABLE 3

Mean Fluorescence Intensity (GMFI) Anti-SKMel-13 Antibody Response

| | Pre-dose | Day 14 | Day 30 | Day 43 | Day 58 | Day 71 | Day 85 | Day 100 |
|---|---|---|---|---|---|---|---|---|
| Group 1 Saline Animal # | | | | | | | | |
| 1 | 4.23 | 13.50 | 9.94 | 37.50 | 27.00 | 34.40 | 26.80 | 19.00 |
| 2 | 3.93 | 21.00 | 11.30 | 168.00 | 81.80 | 64.30 | 44.20 | 33.20 |
| 3 | 3.87 | 33.80 | 22.10 | 92.40 | 64.80 | 64.90 | 43.30 | 30.80 |
| 4 | 4.36 | 4.97 | 5.36 | 11.60 | 15.60 | 53.90 | 31.90 | 19.10 |
| 5 | 3.98 | 46.90 | 20.50 | 34.90 | 38.50 | 80.10 | 55.90 | 36.80 |
| 6 | 3.89 | 5.01 | 5.02 | 8.81 | 8.43 | 25.50 | 15.70 | 13.70 |
| Mean[2] | 4.04 | 20.86 | 12.37 | 58.87 | 39.36 | 53.85 | 36.30 | 25.43 |
| S.D.[2] | 0.20 | 16.75 | 7.36 | 61.33 | 28.72 | 20.51 | 14.35 | 9.35 |
| Median[2] | 3.96 | 17.25 | 10.62 | 36.20 | 32.75 | 59.10 | 37.60 | 24.95 |
| Group 2 10D1 Animal # | | | | | | | | |
| 1 | 3.14 | 33.90 | 116.00 | 565.00 | 475.00 | 493.00 | 322.00 | 188.00 |
| 2 | 3.55 | 6.50 | 6.51 | 51.70 | 40.00 | 55.80 | 32.80 | 26.20 |
| 3 | 2.83 | 8.25 | 7.81 | 229.00 | 219.00 | 317.00 | 244.00 | 146.00 |
| 4 | 2.47 | 27.00 | 24.60 | 322.00 | 179.00 | 281.00 | 159.00 | 107.00 |
| 5 | 2.77 | 7.46 | 7.03 | 87.80 | 59.20 | 81.10 | 50.80 | 34.40 |
| 6[1] | 3.83 | 6.40 | 7.81 | NSC | NSC | NSC | NSC | NSC |
| Mean[2] | 3.10 | 14.92 | 28.29 | 251.10 | 194.44 | 245.58 | 161.72 | 100.32 |
| S.D.[2] | 0.51 | 12.25 | 43.52 | 206.44 | 174.43 | 180.72 | 123.89 | 70.10 |
| Median[2] | 2.99 | 7.86 | 7.81 | 229.00 | 179.00 | 281.00 | 159.00 | 107.00 |
| Group 3 1H5 Animal # | | | | | | | | |
| 1 | 4.26 | 9.55 | 7.31 | 20.40 | 18.90 | 46.70 | 29.20 | 21.50 |
| 2 | 4.10 | 16.40 | 13.90 | 314.00 | 218.00 | 416.00 | 243.00 | 173.00 |
| 3 | 3.36 | 32.20 | 17.10 | 92.80 | 72.70 | 105.00 | 61.70 | 43.80 |
| 4 | 3.22 | 25.60 | 20.40 | 208.00 | 159.00 | 353.00 | 178.00 | 107.00 |
| 5 | 2.99 | 3.77 | 3.19 | 9.03 | 16.00 | 35.90 | 16.40 | 7.59 |
| 6 | 2.72 | 42.00 | 31.20 | 284.00 | 217.00 | 371.00 | 189.00 | 120.00 |
| Mean[2] | 3.44 | 21.59 | 15.52 | 154.71 | 116.93 | 221.27 | 119.55 | 78.82 |
| S.D.[2] | 0.61 | 14.39 | 9.94 | 132.68 | 93.54 | 176.66 | 95.53 | 64.72 |
| Median[2] | 3.29 | 21.00 | 15.50 | 150.40 | 115.85 | 229.00 | 119.85 | 75.40 |

[1]Day 43 sample collected on Day 42 prior to unscheduled necroscopy of animal.
NSC = no sample collected
[2]Mean, Median and standard deviation values calculated from numerical values only The antibody response to the MHC Class I Subtype A2404 present on the SKMel-3 cells also was evaluated, as follows. The plasma samples were analyzed in an ELISA based format for reactivity to purified recombinant MHC Class I, subtype A2404 monomer. 96-well microtiter plates were coated overnight with a 2 µg/ml solution of bacterially-expressed A2404 monomer in PBS and blocked with 1% chicken serum in a PBS/Tween-20 buffer. Plasma samples were incubated on the plates and the antibodies detected with goat anti-human IgG-Fc-specific F(ab')$_2$ conjugated to alkaline phosphatase. The assay was developed with a p-NPP substrate and the absorbance at 405-490 nm was determined on a Spectramax-PC340 spectrophotometer (Molecular Dynamics, Inc.). The OD$_{405}$ for the samples is presented in Table 4.

TABLE 4

OD$_{405}$ Values for Anti-MHC Class I A2404 Antibody Response

| | Pre-dose | Day 14 | Day 30 | Day 43 | Day 58 | Day 71 | Day 85 | Day 100 |
|---|---|---|---|---|---|---|---|---|
| Group 1 Saline Animal # | | | | | | | | |
| 1 | 0.158 | 0.163 | 0.107 | 0.153 | 0.114 | 0.161 | 0.103 | 0.089 |
| 2 | 0.162 | 0.167 | 0.142 | 0.229 | 0.161 | 0.198 | 0.161 | 0.151 |
| 3 | 0.166 | 1.396 | 0.672 | 1.799 | 1.469 | 1.620 | 0.907 | 0.625 |
| 4 | 0.383 | 0.336 | 0.415 | 0.277 | 0.252 | 0.601 | 0.379 | 0.301 |
| 5 | 0.356 | 0.373 | 0.262 | 0.355 | 0.235 | 0.288 | 0.198 | 0.234 |
| 6 | 0.219 | 0.213 | 0.187 | 0.226 | 0.163 | 0.238 | 0.267 | 0.296 |
| Mean[2] | 0.241 | 0.442 | 0.297 | 0.507 | 0.399 | 0.518 | 0.336 | 0.283 |
| S.D.[2] | 0.103 | 0.476 | 0.214 | 0.637 | 0.527 | 0.563 | 0.296 | 0.187 |
| Median[2] | 0.192 | 0.274 | 0.225 | 0.253 | 0.199 | 0.263 | 0.232 | 0.265 |
| Group 2 10D1 Animal # | | | | | | | | |
| 1 | 0.116 | 0.366 | 2.505 | 3.638 | 3.040 | 3.316 | 2.674 | 1.962 |
| 2 | 0.165 | 0.191 | 0.175 | 0.223 | 0.342 | 0.217 | 2.637 | 0.131 |
| 3 | 0.144 | 0.166 | 0.155 | 0.342 | 0.522 | 1.545 | 0.158 | 0.821 |
| 4 | 0.380 | 0.511 | 0.382 | 1.834 | 0.797 | 1.425 | 0.967 | 0.716 |
| 5 | 0.255 | 0.276 | 0.269 | 1.334 | 0.854 | 1.633 | 0.994 | 0.630 |
| 6[1] | 0.287 | 0.733 | 0.489 | NSC | NSC | NSC | NSC | NSC |
| Mean[2] | 0.224 | 0.374 | 0.62 | 1.474 | 1.111 | 1.627 | 1.486 | 0.852 |
| S.D.[2] | 0.101 | 0.216 | 0.911 | 1.385 | 1.098 | 1.105 | 1.119 | 0.675 |
| Median[2] | 0.210 | 0.321 | 0.326 | 1.334 | 0.797 | 1.545 | 0.994 | 0.716 |
| Group 3 1H5 Animal # | | | | | | | | |
| 1 | 0.131 | 0.305 | 0.193 | 1.057 | 0.666 | 2.293 | 1.296 | 1.117 |
| 2 | 0.160 | 0.357 | 0.270 | 2.642 | 1.209 | 3.458 | 2.359 | 1.695 |
| 3 | 0.241 | 0.305 | 0.168 | 0.628 | 0.405 | 0.672 | 0.415 | 0.305 |
| 4 | 0.274 | 0.652 | 0.429 | 2.909 | 2.386 | 3.576 | 3.064 | 1.982 |
| 5 | 0.154 | 0.274 | 0.149 | 0.261 | 0.274 | 0.280 | 0.149 | 0.141 |
| 6 | 0.197 | 0.477 | 0.353 | 1.268 | 0.725 | 1.525 | 0.854 | 0.567 |
| Mean[2] | 0.193 | 0.395 | 0.260 | 1.461 | 0.944 | 1.968 | 1.356 | 0.968 |
| S.D.[2] | 0.055 | 0.145 | 0.112 | 1.079 | 0.776 | 1.388 | 1.142 | 0.757 |
| Median[2] | 0.178 | 0.331 | 0.231 | 1.162 | 0.695 | 1.909 | 1.075 | 0.842 |

[1]Day 43 sample collected on Day 42 prior to unscheduled necroscopy of animal.
NSC = no sample collected
[2]Mean, Median and standard deviation values calculated from numerical values only The results of the SKMel-3 flow cytometry assay and the MHC Class I A2404 ELISA assay demonstrated that the antibody response to the SKMel-3 cellular vaccine as a whole, and to the MHC Class I antigen expressed on the SKMel-3 cells, was stronger in Groups 2 and 3, treated with the 10D1 and 1H5 antibodies, respectively, as compared to Group 1 treated with saline. These results indicate that the 10D1 and 1H5 antibodies were capable of enhancing the humoral immune response to the SKMel-3 cells.

The antibody response to HBsAg was quantitated using a commercially available kit (DiaSorin, Inc., Catalog #P001931). The antibody responses to HBsAg were extremely variable among the animals, with the strongest responses being observed for animals dosed with the 10D1 antibody. The average response of all three test groups was well above the protective immune threshold of 10 mIU/ml, indicating that all groups were immunized by the adjuvanted HBsAg vaccine. No enhancement in the antibody response to HbsAg was observed in the animals dosed with the 1H5 antibody Cellular Immune Responses FACS analysis of peripheral blood was performed to determine whether there were alterations in the numbers and/or percentages of various cell subsets in the treated animals. Cell surface markers were selected to measure the following subsets: lymphocytes (T and B cells), monocytes and dendritic cells. T cell subsets were further analyzed to determine whether there were changes in the activation status of the T cells. Additional analysis was directed at T cell subsets (CD4 and CD8) as well as memory T cell subsets using the markers CD45RO and CD45RA, CD28 and CD95 (which can be used to differentiate naïve T, central memory T and effector memory T cells). Lastly, potential alterations in the number of T regulatory cells (CD4$^+$, CD25hi) were determined.

Memory T cell population in monkey blood was initially evaluated according to the expression of different CD45 molecules (CD45RO$^+$ or CD45RA$^-$) on the cell surface. However, due to polymorphism of CD45RO molecules, the anti-CD45RO antibody used in the assay did not react with all of the monkey samples. Thus, only monkeys whose CD45RO molecules were recognized by the antibody used were analyzed. It was observed that CD3$^+$ CD45RO$^+$ or CD3$^+$ CD45RA$^-$ memory T cell populations were increased following each treatment with the 10D1 or 1H5 antibody as compared to the saline treated animals. To better understand the effect of 10D1 or 1H5 treatment on memory T cell responses, the memory subset of both CD4$^+$ T cells and CD8$^+$ T cells in the monkeys was further characterized. Expression of CD28 and CD95 was evaluated to distinguish different memory subsets of CD4$^+$ and CD8$^+$ T cells. Antigen-experienced T cells were divided into central memory cells, expressing both CD28 and CD95 molecules, and effector memory cells, which express CD95 and lack expression of CD28. Naïve T cells express CD28 but not CD95. Results of this analysis indicated that the number of CD4 central memory T cells was increased in the blood of monkeys following 10D1 or 1H5 treatment. In the meantime, numbers of CD4 effector memory T cells were decreased in monkeys from these two groups. The number of naïve CD4 T cells remained stable among all monkey groups. Moreover, there was no substantial change observed in memory or naïve CD8 T cell subsets.

No substantial changes were observed in any of the following cell populations in any of the treatment groups: $CD20^+$ B cells, $CD11c^{Hi}$ dendritic cells, $CD14^+$ monocytes, activated T or B lymphocytes and regulatory T cells.

In summary, the observed increase in the number of CD4 central memory T cells in the blood of monkeys following 10D1 or 1H5 treatment provides further evidence that treatment with either of these antibodies can result in increased responses of T cells to antigen in vivo.

SUMMARY OF SEQUENCE LISTING

| SEQ ID NO: | SEQUENCE |
|---|---|
| 1 | $V_H$ CDR1 a.a. 1H5 |
| 2 | $V_H$ CDR1 a.a. 3A4 |
| 3 | $V_H$ CDR1 a.a. 6C10 |
| 4 | $V_H$ CDR2 a.a. 1H5 |
| 5 | $V_H$ CDR2 a.a. 3A4 |
| 6 | $V_H$ CDR2 a.a. 6C10 |
| 7 | $V_H$ CDR3 a.a. 1H5 |
| 8 | $V_H$ CDR3 a.a. 3A4 |
| 9 | $V_H$ CDR3 a.a. 6C10 |
| 10 | $V_K1$ CDR1 a.a. 1H5 |
| 11 | $V_K2$ CDR1 a.a. 1H5 |
| 12 | $V_K3$ CDR1 a.a. 1H5 |
| 13 | $V_K4$ CDR1 a.a. 1H5 |
| 14 | $V_K$ CDR1 a.a. 3A4 |
| 15 | $V_K$ CDR1 a.a. 6C10 |
| 16 | $V_K1$ CDR2 a.a. 1H5 |
| 17 | $V_K2$ CDR2 a.a. 1H5 |
| 18 | $V_K3$ CDR2 a.a. 1H5 |
| 19 | $V_K4$ CDR2 a.a. 1H5 |
| 20 | $V_K$ CDR2 a.a. 3A4 |
| 21 | $V_K$ CDR2 a.a. 6C10 |
| 22 | $V_K1$ CDR3 a.a. 1H5 |
| 23 | $V_K2$ CDR3 a.a. 1H5 |
| 24 | $V_K3$ CDR3 a.a. 1H5 |
| 25 | $V_K4$ CDR3 a.a. 1H5 |
| 26 | $V_K$ CDR3 a.a. 3A4 |
| 27 | $V_K$ CDR3 a.a. 6C10 |
| 28 | $V_H$ a.a. 1H5 |
| 29 | $V_H$ a.a. 3A4 |
| 30 | $V_H$ a.a. 6C10 |
| 31 | $V_K1$ a.a. 1H5 |
| 32 | $V_K2$ a.a. 1H5 |
| 33 | $V_K3$ a.a. 1H5 |
| 34 | $V_K4$ a.a. 1H5 |
| 35 | $V_K$ a.a. 3A4 |
| 36 | $V_K$ a.a. 6C10 |
| 37 | $V_H$ n.t. 1H5 |
| 38 | $V_H$ n.t. 3A4 |
| 39 | $V_H$ n.t. 6C10 |
| 40 | $V_K1$ n.t. 1H5 |
| 41 | $V_K2$ n.t. 1H5 |
| 42 | $V_K3$ n.t. 1H5 |
| 43 | $V_K4$ n.t. 1H5 |
| 44 | $V_K$ n.t. 3A4 |
| 45 | $V_K$ n.t. 6C10 |
| 46 | $V_H$ 4-39 germline a.a. |
| 47 | $V_H$ 3-33 germline a.a. |
| 48 | $V_k$ L18 germline a.a. |
| 49 | $V_k$ L15 germline a.a. |
| 50 | $V_H$ a.a. 10D1 |
| 51 | $V_K$ a.a. 10D1 |

SEQUENCE LISTING

```
<160> NUMBER OF SEQ ID NOS: 51

<210> SEQ ID NO 1
<211> LENGTH: 7
<212> TYPE: PRT
<213> ORGANISM: Homo sapiens

<400> SEQUENCE: 1

Asn Ser Asn Tyr Tyr Trp Gly
1               5

<210> SEQ ID NO 2
<211> LENGTH: 5
<212> TYPE: PRT
<213> ORGANISM: Homo sapiens

<400> SEQUENCE: 2

Ser Tyr Gly Met His
1               5

<210> SEQ ID NO 3
<211> LENGTH: 5
<212> TYPE: PRT
<213> ORGANISM: Homo sapiens

<400> SEQUENCE: 3
```

```
Ser His Gly Met His
1               5

<210> SEQ ID NO 4
<211> LENGTH: 16
<212> TYPE: PRT
<213> ORGANISM: Homo sapiens

<400> SEQUENCE: 4

Ser Ile Tyr Tyr Thr Gly Asn Thr Tyr Tyr Asn Pro Ser Leu Lys Ser
1               5                   10                  15

<210> SEQ ID NO 5
<211> LENGTH: 17
<212> TYPE: PRT
<213> ORGANISM: Homo sapiens

<400> SEQUENCE: 5

Val Ile Trp Tyr Asp Gly Ser Asn Lys Tyr Tyr Val Asp Ser Val Lys
1               5                   10                  15

Gly

<210> SEQ ID NO 6
<211> LENGTH: 17
<212> TYPE: PRT
<213> ORGANISM: Homo sapiens

<400> SEQUENCE: 6

Val Val Trp Phe Asp Gly Ser Asn Lys Tyr Tyr Val Asp Ser Val Lys
1               5                   10                  15

Gly

<210> SEQ ID NO 7
<211> LENGTH: 11
<212> TYPE: PRT
<213> ORGANISM: Homo sapiens

<400> SEQUENCE: 7

His Gly Phe Thr Ile Ser Trp Ser Leu Asp Val
1               5                   10

<210> SEQ ID NO 8
<211> LENGTH: 10
<212> TYPE: PRT
<213> ORGANISM: Homo sapiens

<400> SEQUENCE: 8

Gly Pro Gly Tyr Ser Ser Ser Phe Asp Tyr
1               5                   10

<210> SEQ ID NO 9
<211> LENGTH: 10
<212> TYPE: PRT
<213> ORGANISM: Homo sapiens

<400> SEQUENCE: 9

Gly Ser Gly Tyr Ser Ser Gly Phe Asp Tyr
1               5                   10

<210> SEQ ID NO 10
<211> LENGTH: 11
<212> TYPE: PRT
<213> ORGANISM: Homo sapiens
```

```
<400> SEQUENCE: 10

Arg Ala Ser Gln Gly Ile Ser Ser Ala Leu Ala
1               5                   10

<210> SEQ ID NO 11
<211> LENGTH: 11
<212> TYPE: PRT
<213> ORGANISM: Homo sapiens

<400> SEQUENCE: 11

Arg Ala Ser Gln Gly Ile Ser Ser Trp Leu Ala
1               5                   10

<210> SEQ ID NO 12
<211> LENGTH: 11
<212> TYPE: PRT
<213> ORGANISM: Homo sapiens

<400> SEQUENCE: 12

Arg Ala Ser Gln Gly Ile Ser Ser Trp Leu Ala
1               5                   10

<210> SEQ ID NO 13
<211> LENGTH: 11
<212> TYPE: PRT
<213> ORGANISM: Homo sapiens

<400> SEQUENCE: 13

Arg Ala Ser Gln Gly Ile Ser Ser Trp Leu Ala
1               5                   10

<210> SEQ ID NO 14
<211> LENGTH: 11
<212> TYPE: PRT
<213> ORGANISM: Homo sapiens

<400> SEQUENCE: 14

Arg Ala Ser Gln Gly Ile Ser Ser Trp Leu Ala
1               5                   10

<210> SEQ ID NO 15
<211> LENGTH: 11
<212> TYPE: PRT
<213> ORGANISM: Homo sapiens

<400> SEQUENCE: 15

Arg Ala Ser Gln Gly Ile Ser Ser Trp Leu Ala
1               5                   10

<210> SEQ ID NO 16
<211> LENGTH: 7
<212> TYPE: PRT
<213> ORGANISM: Homo sapiens

<400> SEQUENCE: 16

Asp Ala Ser Ser Leu Glu Ser
1               5

<210> SEQ ID NO 17
<211> LENGTH: 7
<212> TYPE: PRT
<213> ORGANISM: Homo sapiens

<400> SEQUENCE: 17

Ala Ala Ser Ser Leu Gln Ser
```

-continued

<210> SEQ ID NO 18
<211> LENGTH: 7
<212> TYPE: PRT
<213> ORGANISM: Homo sapiens

<400> SEQUENCE: 18

Ala Ala Ser Ser Leu Gln Ser
1               5

<210> SEQ ID NO 19
<211> LENGTH: 7
<212> TYPE: PRT
<213> ORGANISM: Homo sapiens

<400> SEQUENCE: 19

Ala Ala Ser Ser Leu Gln Ser
1               5

<210> SEQ ID NO 20
<211> LENGTH: 7
<212> TYPE: PRT
<213> ORGANISM: Homo sapiens

<400> SEQUENCE: 20

Ala Ala Ser Ser Leu Gln Ser
1               5

<210> SEQ ID NO 21
<211> LENGTH: 7
<212> TYPE: PRT
<213> ORGANISM: Homo sapiens

<400> SEQUENCE: 21

Ala Ala Ser Ser Leu Gln Ser
1               5

<210> SEQ ID NO 22
<211> LENGTH: 9
<212> TYPE: PRT
<213> ORGANISM: Homo sapiens

<400> SEQUENCE: 22

Gln Gln Phe Asn Ser Tyr Leu Leu Thr
1               5

<210> SEQ ID NO 23
<211> LENGTH: 10
<212> TYPE: PRT
<213> ORGANISM: Homo sapiens

<400> SEQUENCE: 23

Gln Gln Tyr Asn Ser Tyr Pro Leu Phe Thr
1               5                   10

<210> SEQ ID NO 24
<211> LENGTH: 9
<212> TYPE: PRT
<213> ORGANISM: Homo sapiens

<400> SEQUENCE: 24

Gln Gln Tyr Asn Ser Tyr Pro Leu Thr
1               5

<210> SEQ ID NO 25
<211> LENGTH: 9
<212> TYPE: PRT
<213> ORGANISM: Homo sapiens

<400> SEQUENCE: 25

Gln Gln Phe Asn Ser Tyr Leu Leu Thr
1               5

<210> SEQ ID NO 26
<211> LENGTH: 9
<212> TYPE: PRT
<213> ORGANISM: Homo sapiens

<400> SEQUENCE: 26

Gln Gln Tyr Asn Ser Tyr Pro Leu Thr
1               5

<210> SEQ ID NO 27
<211> LENGTH: 9
<212> TYPE: PRT
<213> ORGANISM: Homo sapiens

<400> SEQUENCE: 27

Gln Gln Tyr Asn Ser Tyr Pro Leu Thr
1               5

<210> SEQ ID NO 28
<211> LENGTH: 121
<212> TYPE: PRT
<213> ORGANISM: Homo sapiens

<400> SEQUENCE: 28

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Asn Ser
                20                  25                  30

Asn Tyr Tyr Trp Gly Trp Ile Arg Gln Pro Pro Gly Lys Glu Leu Glu
            35                  40                  45

Trp Ile Gly Ser Ile Tyr Tyr Thr Gly Asn Thr Tyr Tyr Asn Pro Ser
    50                  55                  60

Leu Lys Ser Arg Val Thr Val Ser Val Asp Thr Ser Arg Asn Gln Phe
65                  70                  75                  80

Ser Leu Asn Leu Asn Ser Val Ile Ala Ala Asp Thr Ala Val Tyr Ser
                85                  90                  95

Cys Ala Arg His Gly Phe Thr Ile Ser Trp Ser Leu Asp Val Trp Gly
            100                 105                 110

Gln Gly Thr Thr Val Thr Val Ser Ser
        115                 120

<210> SEQ ID NO 29
<211> LENGTH: 119
<212> TYPE: PRT
<213> ORGANISM: Homo sapiens

<400> SEQUENCE: 29

Gln Val Gln Val Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

```
Ala Val Ile Trp Tyr Asp Gly Ser Asn Lys Tyr Tyr Val Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg Gly Pro Gly Tyr Ser Ser Phe Asp Tyr Trp Gly Gln Gly
                100                 105                 110
Thr Leu Val Thr Val Ser Ser
            115

<210> SEQ ID NO 30
<211> LENGTH: 119
<212> TYPE: PRT
<213> ORGANISM: Homo sapiens

<400> SEQUENCE: 30

Gln Val Gln Leu Val Glu Ser Gly Gly Gly Val Val Gln Pro Gly Arg
1               5                   10                  15
Ser Leu Arg Leu Ser Cys Thr Ala Ser Gly Phe Thr Phe Ser Ser His
                20                  25                  30
Gly Met His Trp Val Arg Gln Ala Pro Gly Lys Gly Leu Glu Trp Val
            35                  40                  45
Ala Val Val Trp Phe Asp Gly Ser Asn Lys Tyr Tyr Val Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg Gly Ser Gly Tyr Ser Ser Gly Phe Asp Tyr Trp Gly Gln Gly
                100                 105                 110
Thr Leu Val Thr Val Ser Ser
            115

<210> SEQ ID NO 31
<211> LENGTH: 107
<212> TYPE: PRT
<213> ORGANISM: Homo sapiens

<400> SEQUENCE: 31

Ala Ile Gln Leu Thr Gln Ser Pro Ser Ser Leu Ser Ala Ser Val Gly
1               5                   10                  15
Asp Arg Val Thr Ile Thr Cys Arg Ala Ser Gln Gly Ile Ser Ser Ala
                20                  25                  30
Leu Ala Trp Tyr Gln Gln Lys Pro Gly Lys Ala Pro Lys Leu Leu Ile
            35                  40                  45
Tyr Asp Ala Ser Ser Leu Glu Ser Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Phe Asn Ser Tyr Leu Leu
                85                  90                  95
Thr Phe Gly Gly Gly Thr Lys Val Glu Ile Lys
                100                 105

<210> SEQ ID NO 32
<211> LENGTH: 108
```

```
<212> TYPE: PRT
<213> ORGANISM: Homo sapiens

<400> SEQUENCE: 32

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Leu
                85                  90                  95

Phe Thr Phe Gly Pro Gly Thr Lys Val Asp Ile Lys
            100                 105

<210> SEQ ID NO 33
<211> LENGTH: 107
<212> TYPE: PRT
<213> ORGANISM: Homo sapiens

<400> SEQUENCE: 33

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Leu
                85                  90                  95

Thr Phe Gly Gly Gly Thr Lys Val Glu Ile Lys
            100                 105

<210> SEQ ID NO 34
<211> LENGTH: 107
<212> TYPE: PRT
<213> ORGANISM: Homo sapiens

<400> SEQUENCE: 34

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Leu Leu
                85                  90                  95
```

Thr Phe Gly Gly Gly Thr Lys Val Glu Ile Lys
            100                 105

<210> SEQ ID NO 35
<211> LENGTH: 107
<212> TYPE: PRT
<213> ORGANISM: Homo sapiens

<400> SEQUENCE: 35

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Leu
                85                  90                  95

Thr Phe Gly Gly Gly Thr Lys Val Glu Ile Lys
            100                 105

<210> SEQ ID NO 36
<211> LENGTH: 107
<212> TYPE: PRT
<213> ORGANISM: Homo sapiens

<400> SEQUENCE: 36

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Leu
                85                  90                  95

Thr Phe Gly Gly Gly Thr Lys Val Glu Ile Lys
            100                 105

<210> SEQ ID NO 37
<211> LENGTH: 363
<212> TYPE: DNA
<213> ORGANISM: Homo sapiens

<400> SEQUENCE: 37
cagttgcagc tgcaggagtc gggcccagga ctggtgaagc cttcggagac cctgtccctc      60
acctgcactg tctctggtgg ctccatcagc aatagtaatt actactgggg ctggatccgc     120
cagcccccag ggaaggaact ggagtggatt gggagtatct attatactgg gaacacctac     180
tacaacccgt ccctcaagag tcgagtcacc gtgtccgtag acacgtccag gaaccagttc     240
tccctgaacc tgaattctgt tatcgccgca gacacggctg tgtattcctg tgcgagacat     300

```
gggtttacca tcagctggtc tttggacgtc tggggccaag ggaccacggt caccgtctcc    360
tca                                                                  363

<210> SEQ ID NO 38
<211> LENGTH: 357
<212> TYPE: DNA
<213> ORGANISM: Homo sapiens

<400> SEQUENCE: 38
caggtgcagg tggtggagtc tgggggaggc gtggtccagc ctggagggtc cctgagactc    60
tcctgtgcag cgtctggatt caccttcagt agctatggca tgcactgggt ccgccaggct   120
ccaggcaagg ggctggagtg ggtggcagtt atatggtatg atggaagtaa taaatattat   180
gtagactccg tgaagggccg attcaccatc tccagagaca attccaagaa cacgctgtat   240
ctgcaaatga acagcctgag agccgaggac acggctgtgt attactgtgc gagaggtccc   300
gggtatagca gcagctttga ctactggggc cagggaaccc tggtcaccgt ctcctca      357

<210> SEQ ID NO 39
<211> LENGTH: 357
<212> TYPE: DNA
<213> ORGANISM: Homo sapiens

<400> SEQUENCE: 39
caggtgcaac tggtggaatc tgggggaggc gtggtccagc ctggagggtc cctgagactc    60
tcctgtacag cgtctggatt caccttcagt agccatggca tgcactgggt ccgccaggct   120
ccaggcaagg ggctggagtg ggtggcagtt gtatggtttg atggaagtaa taaatactat   180
gtagactccg tgaagggccg attcaccatc tccagagaca attccaagaa cacgctgtat   240
ctacaaatga acagcctgag agccgaggac acggctgtgt attactgtgc gagaggctcc   300
gggtatagca gtggctttga ctactggggc cagggaaccc tggtcaccgt ctcctca      357

<210> SEQ ID NO 40
<211> LENGTH: 321
<212> TYPE: DNA
<213> ORGANISM: Homo sapiens

<400> SEQUENCE: 40
gccatccagt tgacccagtc tccatcctcc ctgtctgcat ctgtaggaga cagagtcacc    60
atcacttgcc gggcaagtca gggcattagc agtgctttag cctggtatca gcagaaacca   120
gggaaagctc ctaagctcct gatctatgat gcctccagtt tggaaagtgg ggtcccatca   180
aggttcagcg gcagtggatc tgggacagat ttcactctca ccatcagcag cctgcagcct   240
gaagattttg caacttatta ctgtcaacag tttaatagtt acctgctcac tttcggcgga   300
gggaccaagg tggagatcaa a                                              321

<210> SEQ ID NO 41
<211> LENGTH: 324
<212> TYPE: DNA
<213> ORGANISM: Homo sapiens

<400> SEQUENCE: 41
gacatccaga tgacccagtc tccatcctca ctgtctgcat ctgtaggaga cagagtcacc    60
atcacttgtc gggcgagtca gggtattagc agctggttag cctggtatca gcagaaacca   120
gagaaagccc ctaagtccct gatctatgct gcatccagtt tgcaaagtgg ggtcccatca   180
aggttcagcg gcagtggatc tgggacagat ttcactctca ccatcagcag cctgcagcct   240
```

```
gaagattttg caacttatta ctgccaacag tataatagtt acccttatt cactttcggc      300 cctgggacca aagtggatat caaa                                            324

<210> SEQ ID NO 42
<211> LENGTH: 321
<212> TYPE: DNA
<213> ORGANISM: Homo sapiens

<400> SEQUENCE: 42
gacatccaga tgacccagtc tccatcctca ctgtctgcat ctgtaggaga cagagtcacc      60
atcacttgtc gggcgagtca gggtattagc agctggttag cctggtatca gcagaaacca     120
gagaaagccc ctaagtccct gatctatgct gcatccagtt tgcaaagtgg ggtcccatca     180
aggttcagcg gcagtggatc tgggacagat ttcactctca ccatcagcag cctgcagcct     240
gaagattttg caacttatta ctgccaacag tataatagtt acccgctcac tttcggcgga     300
gggaccaagg tggagatcaa a                                               321

<210> SEQ ID NO 43
<211> LENGTH: 321
<212> TYPE: DNA
<213> ORGANISM: Homo sapiens

<400> SEQUENCE: 43
gacatccaga tgacccagtc tccatcctca ctgtctgcat ctgtaggaga cagagtcacc      60
atcacttgtc gggcgagtca gggtattagc agctggttag cctggtatca gcagaaacca     120
gagaaagccc ctaagtccct gatctatgct gcatccagtt tgcaaagtgg ggtcccatca     180
aggttcagcg gcagtggatc tgggacagat ttcactctca ccatcagcag cctgcagcct     240
gaagattttg caacttatta ctgtcaacag tttaatagtt acctgctcac tttcggcgga     300
gggaccaagg tggagatcaa a                                               321

<210> SEQ ID NO 44
<211> LENGTH: 321
<212> TYPE: DNA
<213> ORGANISM: Homo sapiens

<400> SEQUENCE: 44
gacatccaga tgacccagtc tccatcctca ctgtctgcat ctgtaggaga cagagtcacc      60
atcacttgtc gggcgagtca gggtattagc agctggttag cctggtatca gcagaaacca     120
gagaaagccc ctaagtccct gatctatgct gcatccagtt tgcaaagtgg ggtcccatca     180
aggttcagcg gcagtggatc tgggacagat ttcactctca ccatcagcag cctgcagcct     240
gaagattttg caacttatta ctgccaacag tataatagtt accctctcac tttcggcgga     300
gggaccaagg tggagatcaa a                                               321

<210> SEQ ID NO 45
<211> LENGTH: 321
<212> TYPE: DNA
<213> ORGANISM: Homo sapiens

<400> SEQUENCE: 45
gacatccaga tgacccagtc tccatcctca ctgtctgcat ctgtaggaga cagagtcacc      60
atcacttgtc gggcgagtca gggtattagc agctggttag cctggtatca gcagaaacca     120
gagaaagccc ctaagtccct gatctatgct gcatccagtt tgcaaagtgg ggtcccatca     180
aggttcagcg gcagtggatc tgggacagat ttcactctca ccatcagcag cctgcagcct     240
```

```
gaagattttg caacttatta ctgccaacag tataatagtt acccgctcac tttcggcgga    300
gggaccaagg tggagatcaa a                                              321
```

<210> SEQ ID NO 46
<211> LENGTH: 99
<212> TYPE: PRT
<213> ORGANISM: Homo sapiens

<400> SEQUENCE: 46

```
Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg
```

<210> SEQ ID NO 47
<211> LENGTH: 98
<212> TYPE: PRT
<213> ORGANISM: Homo sapiens

<400> SEQUENCE: 47

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg
```

<210> SEQ ID NO 48
<211> LENGTH: 94
<212> TYPE: PRT
<213> ORGANISM: Homo sapiens

<400> SEQUENCE: 48

```
Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60
```

```
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Phe Asn Ser Tyr
                 85                  90
```

<210> SEQ ID NO 49
<211> LENGTH: 95
<212> TYPE: PRT
<213> ORGANISM: Homo sapiens

<400> SEQUENCE: 49

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Ser Ser Trp
                20                  25                  30

Leu Ala Trp Tyr Gln Gln Lys Pro Glu Lys Ala Pro Lys Ser Leu Ile
             35                  40                  45

Tyr Ala Ala Ser Ser Leu Gln Ser Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Asn Ser Tyr Pro
                 85                  90                  95
```

<210> SEQ ID NO 50
<211> LENGTH: 118
<212> TYPE: PRT
<213> ORGANISM: Homo sapiens

<400> SEQUENCE: 50

```
Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
                20                  25                  30

Thr Met His Trp Val Arg Gln Ala Pro Gly Lys Gly Leu Glu Trp Val
             35                  40                  45

Thr Phe Ile Ser Tyr Asp Gly Asn Asn Lys Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Ile Tyr Tyr Cys
                 85                  90                  95

Ala Arg Thr Gly Trp Leu Gly Pro Phe Asp Tyr Trp Gly Gln Gly Thr
            100                 105                 110

Leu Val Thr Val Ser Ser
        115
```

<210> SEQ ID NO 51
<211> LENGTH: 108
<212> TYPE: PRT
<213> ORGANISM: Homo sapiens

<400> SEQUENCE: 51

```
Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Gly Ser Ser
                20                  25                  30

Tyr Leu Ala Trp Tyr Gln Gln Lys Pro Gly Gln Ala Pro Arg Leu Leu
             35                  40                  45
```

-continued

```
Ile Tyr Gly Ala Phe Ser Arg Ala Thr Gly Ile Pro Asp Arg Phe Ser
    50                  55                  60
Gly Ser Gly Ser Gly Thr Asp Phe Thr Leu Thr Ile Ser Arg Leu Glu
65                  70                  75                  80
Pro Glu Asp Phe Ala Val Tyr Tyr Cys Gln Gln Tyr Gly Ser Ser Pro
                85                  90                  95
Trp Thr Phe Gly Gln Gly Thr Lys Val Glu Ile Lys
                100                 105
```

We claim:

1. A pharmaceutical composition comprising an isolated monoclonal antibody, or an antigen-binding portion thereof, wherein the antibody comprises a heavy chain variable region CDR1 comprising SEQ ID NO: 3, a heavy chain variable region CDR2 comprising SEQ ID NO: 6, a heavy chain variable region CDR3 comprising SEQ ID NO: 9, a light chain variable region CDR1 comprising SEQ ID NO: 15, a light chain variable region CDR2 comprising SEQ ID NO: 21, and a light chain variable region CDR3 comprising SEQ ID NO: 27.

2. The pharmaceutical composition of claim 1, wherein the heavy chain variable region comprises SEQ ID NO: 30 and the light chain variable region comprises SEQ ID NO: 36.

3. An isolated human monoclonal antibody, or antigen binding portion thereof, wherein the antibody comprises: a heavy chain variable region CDR1 comprising SEQ ID NO: 3, a heavy chain variable region CDR2 comprising SEQ ID NO: 6, a heavy chain variable region CDR3 comprising SEQ ID NO: 9, a light chain variable region CDR1 comprising SEQ ID NO: 15, a light chain variable region CDR2 comprising SEQ ID NO: 21, and a light chain variable region CDR3 comprising SEQ ID NO: 27.

4. The isolated monoclonal antibody, or the antigen-binding portion thereof, of claim 3, wherein the heavy chain variable region comprises SEQ ID NO: 30 and the light chain variable region comprises SEQ ID NO: 36.

* * * * *